United States Patent [19]

Braford-Goldberg et al.

[11] Patent Number: 5,501,962
[45] Date of Patent: Mar. 26, 1996

[54] INTERLEUKEN-3 (IL-3) HUMAN/MURINE HYBRID POLYPEPTIDES AND RECOMBINANT PRODUCTION OF THE SAME

[75] Inventors: Sarah R. Braford-Goldberg, St. Louis; Alan M. Easton, Maryland Heights; Barbara K. Klein, St. Louis; John P. McKearn, Pacific; Peter O. Olins, Glencoe, all of Mo.

[73] Assignee: G. D. Searle & Co., Chicago, Ill.

[21] Appl. No.: 81,539

[22] Filed: Jun. 21, 1993

[51] Int. Cl.$^6$ .......................... C12N 15/24; C12N 15/27; C07K 14/54; A61K 38/20

[52] U.S. Cl. .................... 435/69.52; 435/172.3; 435/240.2; 435/252.3; 435/254.11; 435/320.1; 536/23.4; 536/23.5; 536/24.1; 530/351; 424/85.2

[58] Field of Search .......................... 530/351; 435/69.52, 435/172.3, 240.1, 252.3, 320.1, 254.11, 240.2; 536/23.5, 23.4, 24.1; 930/141; 424/85.2

[56] References Cited

U.S. PATENT DOCUMENTS

| 4,877,729 | 10/1989 | Clark et al. | 435/68 |
| 4,959,455 | 9/1990 | Clark et al. | 530/351 |
| 5,032,395 | 7/1991 | Clark et al. | 424/85.1 |

FOREIGN PATENT DOCUMENTS

0413383A1 2/1991 European Pat. Off. ........ C12N 15/27

(List continued on next page.)

OTHER PUBLICATIONS

Ian Clark–Lewis et al, *Proc. Nat'l Acad. Sci.* 85, 7897–7901 (1988).
Ian Clark–Lewis et al, *Science*, 231, 134–139 (1986).
T. Yokota et al, *Proc. Nat'l Acad. Sci.*, 81, 1070–1074.
M. C. Fung, *Nature*, 307, 233–237 (1984).
L. Dorssers et al, *Gene*, 55, 115–124 (1987) Netherlands.

J. A. Phillips et al, *Gene*, 84, 501–507, (1989) Netherlands.
Ian Clark–Lewis et al, "Struct.–Function Studies of Interleukin–3 Using an Automated Peptide Syn. Approach", 323–334, Alan R. Liss Inc. (1987) USA.
N. A. Lokker et al, *The Journal of Biological Chemistry*, 266 10624–10631 (1991).
James N. Ihle et al, *The Journal of Immunology*, 126, No. 6, 2184–2189 (1981).
Lambert Dorssers et al, *The Journal of Biological Chemistry* 266, No. 31, 21310–21317 (1991).
Yu–Chung Yang et al, "Human IL–3: Identif. by Expression Cloning of a Novel Hematopoietic Growth Factor Related to Murine IL–3", *Cell*, 47, 3–10 (1986).
K. Kaushansky et al, *J. Clin. Invest.*, 90, 1879–1888 (1992).
A. F. Lopez et al, *Proc. Nat'l Acad. Sci.*, 89, 11842–11846 (1992).

(List continued on next page.)

Primary Examiner—Garnette D. Draper
Assistant Examiner—David L. Fitzgerald
Attorney, Agent, or Firm—Dennis A. Bennett

[57] ABSTRACT

The present invention relates to recombinant human interleukin-3 (hIL-3) variant or mutant proteins (muteins) in which segments of the polypeptide sequence of the human IL-3 polypeptide have been replaced by segments of the murine (mouse) interleukin-3 (mIL-3) polypeptide to form human/murine chimeric hybrid polypeptides. The human/mouse hybrid IL-3 may have amino acid deletions at the N-terminus or the C-terminus or at both the N- and C-termini and in some cases may also contain additional amino acid substitutions or deletions. The human/murine IL-3 muteins retain at least one biological activity of native hIL-3 and may also exhibit an improved side effects profile such as a reduction in the stimulation of leukotriene release or histamine release. The invention also relates to pharmaceutical compositions containing the h/m IL-3 hybrids and methods for using them. Additionally, the present invention relates to recombinant expression vectors comprising nucleotide sequences encoding the IL-3 hybrid muteins, related microbial expression systems, and processes for making the IL-3 hybrids using the microbial expression systems.

17 Claims, 20 Drawing Sheets

Mouse - Human Chimeric Hybrid Mutants

```
                  20         30         40         50         60
                   |          |          |          |          |
Human   15-NCS NMIDEIITHLK QPPLPLL   DFNNL NGEDQD ILMENN LRRPNLEAFNR AVKSLQ
               ||| .:::.|||..|.       :  .  .::::. |.:..  :||.||.|    .  .::
Mouse      NCS SIVKEIIGKLP ^^^^^^^   EPELK TDDEGP SLRNKS FRRVNLSKFVE SQGEVD
                   M1         M2       M3    M4     M5       M6        M7

70         80         90        100        110        120
                   |          |          |          |          |          |
Human    NAS..AI ESILKNLLP CLPLATAA PTRH  PIHIK DGDWN EFRRKLTFYLKTLENAQAQQ-125
         .. .|  .| |..| .  |||   .... .. .: |:      |::  :||:|| ||   |:: :.
Mouse    PEDRYVI KSNLQKLNS CLPTSAND SALP  GVFIR ^^DLD DFRKKLRFYMVHLNDLETVL
            M8       M9       M10     M11   M12   M13
```

^^^ Denotes deletions
| Denotes conserved residues

FOREIGN PATENT DOCUMENTS

| | | | |
|---|---|---|---|
| 2-482 | 1/1990 | Japan | C12P 21/02 |
| 3-236400 | 10/1991 | Japan | C07K 13/00 |
| 4-63595 | 2/1992 | Japan | C12N 15/24 |
| 2210883 | 6/1989 | United Kingdom | C12N 15/00 |
| 88/00598 | 1/1988 | WIPO | C07K 13/00 |
| 88/04691 | 6/1988 | WIPO | C12N 15/00 |
| 88/05469 | 7/1988 | WIPO | C12P 21/00 |
| 88/06161 | 8/1988 | WIPO | C07K 13/00 |
| 90/10705 | 9/1990 | WIPO | C12P 21/02 |
| 90/12874 | 11/1990 | WIPO | C12N 15/27 |
| 91/00350 | 1/1991 | WIPO | C12N 15/27 |
| 91/02754 | 3/1991 | WIPO | C07K 13/00 |
| 9204455 | 3/1992 | WIPO | |
| 9206116 | 4/1992 | WIPO | |
| 9310229 | 5/1993 | WIPO | |

OTHER PUBLICATIONS

Lokker et al, *EMBO* 10(8) 1991, pp. 2125–2131.
Jakuboniski Cancer Invest 11 (Suppl. 1993) 30–31.
Lokker et al, *JBC* 266(16) 1991, pp. 10624–10631.
Dorssers et al. *JBC* 266(3) 1991, pp. 21310–21317.
Kaushansky et al. *J. Clin. Invest.* 90, 1992, pp. 1879–1888.
Kaushansky et al. J. Cell. Biochem. Suppl 15F, 1991, p. 114 (p. 428).

```
      1                          5                              10
ATG  GCT  CCA  ATG  ACT  CAG  ACT  ACT  TCT  CTT  AAG  ACT  TCT
Met  Ala  Pro  Met  Thr  Gln  Thr  Thr  Ser  Leu  Lys  Thr  Ser 15                         20                         25
TGG  GTT  AAC  TGC  TCT  AAC  ATG  ATC  GAT  GAA  ATT  ATA  ACA
Trp  Val  Asn  Cys  Ser  Asn  Met  Ile  Asp  Glu  Ile  Ile  Thr 30                    35
CAC  TTA  AAG  CAG  CCA  CCT  TTG  CCT  TTG  CTG  GAC  TTC  AAC
His  Leu  Lys  Gln  Pro  Pro  Leu  Pro  Leu  Leu  Asp  Phe  Asn 40                         45                         50
AAC  CTC  AAT  GGG  GAA  GAC  CAA  GAC  ATT  CTG  ATG  GAA  AAT
Asn  Leu  Asn  Gly  Glu  Asp  Gln  Asp  Ile  Leu  Met  Glu  Asn 55                         60
AAC  CTT  CGA  AGG  CCA  AAC  CTG  GAG  GCA  TTC  AAC  AGG  GCT
Asn  Leu  Arg  Arg  Pro  Asn  Leu  Glu  Ala  Phe  Asn  Arg  Ala 65                         70                         75
GTC  AAG  AGT  TTA  CAG  AAT  GCA  TCA  GCA  ATT  GAG  AGC  ATT
Val  Lys  Ser  Leu  Gln  Asn  Ala  Ser  Ala  Ile  Glu  Ser  Ile 80                         85                         90
CTT  AAA  AAT  CTC  CTG  CCA  TGT  CTG  CCC  CTG  GCC  ACG  GCC
Leu  Lys  Asn  Leu  Leu  Pro  Cys  Leu  Pro  Leu  Ala  Thr  Ala 95                         100
GCA  CCC  ACG  CGA  CAT  CCA  ATC  CAT  ATC  AAG  GAC  GGT  GAC
Ala  Pro  Thr  Arg  His  Pro  Ile  His  Ile  Lys  Asp  Gly  Asp 105                        110                        115
TGG  AAT  GAA  TTC  CGT  CGT  AAA  CTG  ACC  TTC  TAT  CTG  AAA
Trp  Asn  Glu  Phe  Arg  Arg  Lys  Leu  Thr  Phe  Tyr  Leu  Lys 120                        125
ACC  TTG  GAG  AAC  GCG  CAG  GCT  CAA  CAG  ACC  ACT  CTG  TCG
Thr  Leu  Glu  Asn  Ala  Gln  Ala  Gln  Gln  Thr  Thr  Leu  Ser

130
CTA  GCG  ATC  TTT  TAA  TAA    [SEQ ID NO:104]
Leu  Ala  Ile  Phe  END  END    [SEQ ID NO:13]
```

FIG. 1

```
                                                       EcoRV
aa20                                                                                          XhoI
     ATCGATGAAATCATCACCCACCTGAAGCAGCCACCGCTGCCGCTGCTGGACTTCAACAAC
   1 ------+---------+---------+---------+---------+---------+  60
     IleAspGluIleIleThrHisLeuLysGlnProProLeuProLeuLeuAspPheAsnAsn

PstI
                                                        NsiI
     CTCAATGGTGAAGACCAAGATATCCTGATGGAAAATAACCTTCGTCGTCCAAACCTCGAG
  61 ------+---------+---------+---------+---------+---------+ 120
     LeuAsnGlyGluAspGlnAspIleLeuMetGluAsnAsnLeuArgArgProAsnLeuGlu

GCATTCAACCGTGCTGCTGTCAAGTCTCTGCAGAATGCAT  [SEQ ID NO:26]  aa70
 121 ------+---------+---------+---------+--- 157
     AlaPheAsnArgAlaAlaValLysSerLeuGlnAsnAla  [SEQ ID NO:27]
```

ClaI to NsiI Replacement Fragment

FIG. 2

```
          N                                      H
          C                                      p
          O                                      a
          I                                      I
      CCATGGCTCCAATGACTCAGACTACTTCTCTTAAGACTTCTTGGGTTAACTGCTCTAACA
  1   ---------+---------+---------+---------+---------+---------+
                                60
      GGTACCGAGGTTACTGAGTCTGATGAAGAGAATTCTGAAGAACCCAATTGACGAGATTGT

MetAlaProMetThrGlnThrThrSerLeuLysThrSerTrpValAsnCysSerAsnMet -

C
                  1
                  a
                  I
      TGATCGATGAAATTATAACACACTTAAAGCAGCCACCTTTGCCTTTGCTGGACTTCAACA
 61   ---------+---------+---------+---------+---------+---------+
                               120
      ACTAGCTACTTTAATATTGTGTGAATTTCGTCGGTGGAAACGGAAACGACCTGAAGTTGT

IleAspGluIleIleThrHisLeuLysGlnProProLeuProLeuLeuAspPheAsnAsn -

ACCTCAATGGGGAAGACCAAGACATTCTGATGGAAAATAACCTTCGAAGGCCAAACCTGG
121   ---------+---------+---------+---------+---------+---------+ 180
      TGGAGTTACCCCTTCTGGTTCTGTAAGACTACCTTTTATTGGAAGCTTCCGGTTTGGACC

LeuAsnGlyGluAspGlnAspIleLeuMetGluAsnAsnLeuArgArgProAsnLeuGlu -

N
                                       s
                                       i
                                       I
      AGGCATTCAACAGGGCTGTCAAGAGTTTACAGAATGCATCAGCAATTGAGAGCATTCTTA
181   ---------+---------+---------+---------+---------+---------+
                               240
      TCCGTAAGTTGTCCCGACAGTTCTCAAATGTCTTACGTAGTCGTTAACTCTCGTAAGAAT

AlaPheAsnArgAlaValLysSerLeuGlnAsnAlaSerAlaIleGluSerIleLeuLys -

AAAATCTCCTGCCATGTCTGCCCCTGGCCACGGCCGCACCCACGCGACATCCAATCCATA
241   ---------+---------+---------+---------+---------+---------+
                               300
      TTTTAGAGGACGGTACAGACGGGGACCGGTGCCGGCGTGGGTGCGCTGTAGGTTAGGTAT

AsnLeuLeuProCysLeuProLeuAlaThrAlaAlaProThrArgHisProIleHisIle -

E
                           c
                           o
                           R
                           I
      TCAAGGACGGTGACTGGAATGAATTCCGTCGTAAACTGACCTTCTATCTGAAAACCTTGG
301   ---------+---------+---------+---------+---------+---------+
                               360
      AGTTCCTGCCACTGACCTTACTTAAGGCAGCATTTGACTGGAAGATAGACTTTTGGAACC

LysAspGlyAspTrpAsnGluPheArgArgLysLeuThrPheTyrLeuLysThrLeuGlu -
```

FIG. 3a

```
                                            H
                                            i
                                            n
                              N             d
                              h             I
                              e             I
                              I             I
     AGAACGCGCAGGCTCAACAGACCACTCTGTCGCTAGCGATCTTTTAATAAGCTT [SEQ ID
     NO:121]
361  ----------+----------+----------+----------+----------+---- 414
     TCTTGCGCGTCCGAGTTGTCTGGTGAGACAGCGATCGCTAGAAAATTATTCGAA [SEQ ID
     NO:120]

AsnAlaGlnAlaGlnGlnThrThrLeuSerLeuAlaIlePheEndEnd [SEQ ID NO:13]
```

FIG. 3b

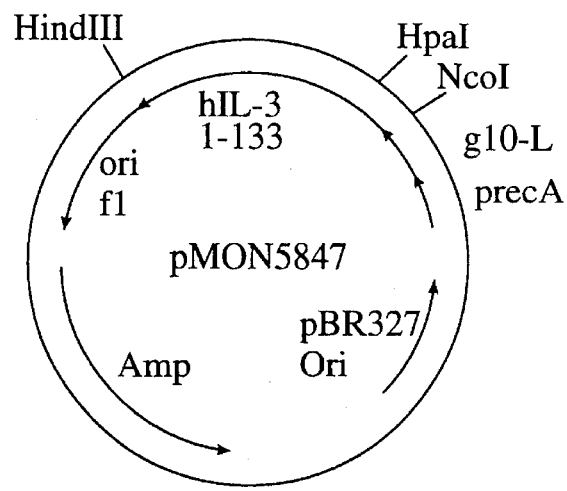
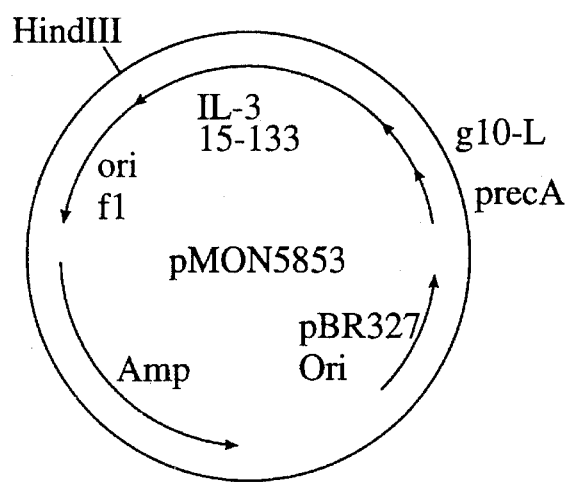
Cleave with NcoI and HpaI.
Klenow fill the NcoI end to render it blunt.
Ligate the blunt ends.
Transform E. coli JM101 to ampicillin resistance
FIG. 6

```
                         5                    10                   15
    Ala Ser Ile Ser Gly Arg Asp Thr His Arg Leu Thr Arg Thr Leu
                        20                    25                   30
    Asn Cys Ser Ser Ile Val Lys Glu Ile Ile Gly Lys Leu Pro Glu
                        35                    40                   45
    Pro Glu Leu Lys Thr Asp Asp Glu Gly Pro Ser Leu Arg Asn Lys
                        50                    55                   60
    Ser Phe Arg Arg Val Asn Leu Ser Lys Phe Val Glu Ser Gln Gly
                        65                    70                   75
    Glu Val Asp Pro Glu Asp Arg Tyr Val Ile Lys Ser Asn Leu Gln
                        80                    85                   90
    Lys Leu Asn Cys Cys Leu Pro Thr Ser Ala Asn Asp Ser Ala Leu
                        95                   100                  105
    Pro Gly Val Phe Ile Arg Asp Leu Asp Asp Phe Arg Lys Lys Leu
                       110                   115                  120
    Arg Phe Tyr Met Val His Leu Asn Asp Leu Glu Thr Val Leu Thr
                       125                   130                  135
    Ser Arg Pro Pro Gln Pro Ala Ser Gly Ser Val Ser Pro Asn Arg
                       140
    Gly Thr Val Glu Cys   [SEQ ID NO:118]
```

MURINE IL-3

Mouse — Human Chimeric Hybrid Mutants

```
                 20              30              40              50              60
                  |               |               |               |               |
Human  15-NCS NMIDEIITHLK QPPLPLL DFNNL NGEDQD ILMENN LRRPNLEAFNR AVKSLQ
          |||  ::.:.|||..|.  |||     :...    ..:::.  :...:  |::.||.|.|  .  .::
Mouse     NCS SIVKEIIGKLP         ^^^^^^  EPELK TDDEGP SLRNKS FRRVNLSKFVE SQGEVD
               └────M1────┘       └─M2─┘ └─M3─┘ └─M4─┘ └─M5─┘ └────M6────┘ └─M7─┘

70              80              90             100             110             120
                  |               |               |               |               |               |
Human    NAS..AI ESILKNLLP CLPLATAA PTRH PIHIK DGDWN EFRRKLTFYLKTLENAQAQQ-125
          |.|    :|..:|..|  |||      :|.   ::..  :..   :||.||.|:|.||..  ..
Mouse   PEDRYVI KSNLQKLNS CLPTSAND SALP GVFIR ^^DLD DFRKKLRFYMVHLNDLETVL
        └──M8──┘ └──M9──┘ └──M10──┘ └M11┘ └M12┘ └M13┘
```

^^^ Denotes deletions
| Denotes conserved residues 5,501,962

INTERLEUKIN-3 (IL-3) HUMAN/MURINE HYBRID POLYPEPTIDES AND RECOMBINANT PRODUCTION OF THE SAME

FIELD OF THE INVENTION

The present invention relates to mutants or variants of human interleukin-3 (hIL-3) which are hybrids of hIL-3 and murine (mouse) interleukin-3 (mIL-3) in which segments of the native murine IL-3 polypeptide have been substituted for segments of native human IL-3 and which may also have other amino acid substitutions in the polypeptide. These hybrids may have portions of the N- and/or C- terminus amino acids of native hIL-3 deleted. These hybrid polypeptides retain one or more activities of human IL-3 and may also exhibit an improved side effects profile.

BACKGROUND OF THE INVENTION

Colony stimulating factors (CSFs) which stimulate the differentiation and/or proliferation of bone marrow cells have generated much interest because of their therapeutic potential for restoring depressed levels of hematopoietic stem cell-derived cells. CSFs in both human and murine systems have been identified and distinguished according to their activities. For example, granulocyte-CSF (G-CSF) and macrophage-CSF (M-CSF) stimulate the in vitro formation of neutrophilic, granulocyte and macrophage colonies, respectively while GM-CSF and interleukin-3 (IL-3) have broader activities and stimulate the formation of both macrophage, neutrophilic and eosinophilic granulocyte colonies. IL-3 also stimulates the formation of mast, megakaryocyte and pure and mixed erythroid colonies.

Because of its ability to stimulate the proliferation of a number of different cell types and to support the growth and proliferation of progenitor cells, IL-3 has potential for therapeutic use in restoring hematopoietic cells to normal amounts in those cases where the number of cells has been reduced due to diseases or to therapeutic treatments such as radiation and chemotherapy.

Interleukin-3 (IL-3) is a hematopoietic growth factor which has the property of being able to promote the survival, growth and differentiation of hematopoietic cells. Among the biological properties of IL-3 are the ability (a) to support the growth and differentiation of progenitor cells committed to all, or virtually all, blood cell lineages; (b) to interact with early multipotential stem cells; (c) to sustain the growth of pluripotent precursor cells; (d) to stimulate proliferation of chronic myelogenous leukemia (CML) cells; (e) to stimulate proliferation of mast cells, eosinophils and basophils; (f) to stimulate DNA synthesis by human acute myelogenous leukemia (AML) blasts; (g) to prime granulocytic cells for production of leukotrienes and histamines; (h) to induce leukocyte chemotaxis; and (i) to induce cell surface molecules needed for leukocyte adhesion.

Mature human interleukin-3 (hIL-3) consists of 133 amino acids. It has one disulfide bridge and two potential glycosylation sites (Yang, et al., CELL 47:3 (1986)).

Murine IL-3 (mIL-3) was first identified by Ihle, et al., J. IMMUNOL. 126:2184 (1981) as a factor which induced expression of a T cell associated enzyme, 20α-hydroxysteroid dehydrogenase. The factor was purified to homogeneity and shown to regulate the growth and differentiation of numerous subclasses of early hematopoietic and lymphoid progenitor cells.

In 1984, cDNA clones coding for murine IL-3 were isolated (Fung, et al., NATURE 307:233 (1984) and Yokota, et al., PROC. NATL. ACAD. SCI. USA 81:1070 (1984)). The murine DNA sequence coded for a polypeptide of 166 amino acids including a putative signal peptide.

The gibbon IL-3 sequence was obtained using a gibbon cDNA expression library. The gibbon IL-3 sequence was then used as a probe against a human genomic library to obtain a human IL-3 sequence.

Gibbon and human genomic DNA homologues of the murine IL-3 sequence were disclosed by Yang, et al., CELL 47:3 (1986). The human sequence reported by Yang, et al. included a serine residue at position 8 of the mature protein sequence. Following this finding, others reported isolation of $Pro^8$ hIL-3 cDNAs having proline at position 8 of the protein sequence. Thus it appears that there may be two allelic forms of hIL-3.

Dorssers, et al., GENE 55:115 (1987), found a clone from a human cDNA library which hybridized with mIL-3. This hybridization was the result of the high degree of homology between the 3' noncoding regions of mIL-3 and hIL-3. This cDNA coded for an hIL-3 ($Pro^8$) sequence.

U.S. Pat. No. 4,877,729 and U.S. Pat. No. 4,959,454 disclose human IL-3 and gibbon IL-3 cDNAs and the protein sequences for which they code. The hIL-3 disclosed has serine rather than proline at position 8 in the protein sequence.

Clark-Lewis, et al., SCIENCE 231: 134 (1986) performed a functional analysis of murine IL-3 analogues synthesized with an automated peptide synthesizer. The authors concluded that the stable tertiary structure of the complete molecule was required for full activity. A study on the role of the disulfide bridges showed that replacement of all four cysteines by alanine gave a molecule with 1/500th the activity as the native molecule. Replacement of two of the four Cys residues by Ala($Cys^{79}$, $Cys^{140} \rightarrow Ala^{79}$, $Ala^{140}$) resulted in an increased activity. The authors concluded that in murine IL-3 a single disulfide bridge is required between cysteines 17 and 80 to get biological activity that approximates physiological levels and that this structure probably stabilizes the tertiary structure of the protein to give a conformation that is optimal for function. (Clark-Lewis, et al., PROC. NATL. ACAD. SCI. USA 85: 7897 (1988)).

International Patent Application (PCT) WO 88/00598 discloses gibbon- and human-like IL-3. The hIL-3 contains a $Ser^8 \rightarrow Pro^8$ replacement. Suggestions are made to replace Cys by Ser, thereby breaking the disulfide bridge, and to replace one or more amino acids at the glycosylation sites.

EP-A-0275598 (WO 88/04691) illustrates that $Ala^1$ can be deleted while retaining biological activity. Some mutant hIL-3 sequences are provided, e.g., two double mutants, $Ala^1 \rightarrow Asp^1$, $Trp^{13} \rightarrow Arg^{13}$ (pGB/IL-302) and $Ala^1 \rightarrow Asp^1$, $Met^3 \rightarrow Thr^3$ (pGB/IL-304) and one triple mutant $Ala^1 \rightarrow Asp^1$, $Leu^9 \rightarrow Pro^9$, $Trp^{13} \rightarrow Arg^{13}$ (pGB/IL-303).

WO 88/05469 describes how deglycosylation mutants can be obtained and suggests mutants of $Arg^{54}Arg^{55}$ and $Arg^{108}Arg^{109}Lys^{110}$ might avoid proteolysis upon expression in Saccharomyces cerevisiae by KEX2 protease. No mutated proteins are disclosed. Glycosylation and the KEX2 protease activity are only important, in this context, upon expression in yeast.

WO 88/06161 mentions various mutants which theoretically may be conformationally and antigenically neutral. The only actually performed mutations are $Met^2 \rightarrow Ile^2$ and $Ile^{131} \rightarrow Leu^{131}$. It is not disclosed whether the contemplated neutralities were obtained for these two mutations.

WO 91/00350 discloses nonglycosylated hIL-3 analog proteins, for example, hIL-3 (Pro$^8$Asp$^{15}$Asp$^{70}$), Met$^3$ rhuIL-3 (Pro$^8$Asp$^{15}$Asp$^{70}$); Thr$^4$ rhuIL-3 (Pro$^8$Asp$^{15}$Asp$^{70}$) and Thr$^6$ rhuIL-3 (Pro$^8$Asp$^{15}$Asp$^{70}$). It is said that these protein compositions do not exhibit certain adverse side effects associated with native hIL-3 such as urticaria resulting from infiltration of mast cells and lymphocytes into the dermis. The disclosed analog hIL-3 proteins may have N termini at Met$^3$, Thr$^4$, or Thr$^6$.

WO 91/12874 discloses cysteine added variants (CAVs) of IL-3 which have at least one Cys residue substituted for a naturally occurring amino acid residue.

SUMMARY OF THE INVENTION

The present invention relates to recombinant human interleukin-3 (hIL-3) variant or mutant proteins (muteins) in which segments of the polypeptide sequence of the human IL-3 polypeptide have been replaced by segments of the murine (mouse) interleukin-3 (mIL-3) polypeptide to form human/murine chimeric hybrid polypeptides. The human/mouse hybrid IL-3 may have amino acid deletions at the N-terminus or the C-terminus or at both the N- and C-termini and in some cases may also contain additional amino acid substitutions and/or deletions. The human/murine IL-3 muteins retain at least one biological activity of native hIL-3 and may also exhibit an improved side effects profile such as a reduction in the stimulation of leukotriene release or histamine release. The invention also relates to pharmaceutical compositions containing the h/m IL-3 hybrids and methods for using them. Additionally, the present invention relates to recombinant expression vectors comprising nucleotide sequences encoding the IL-3 hybrid muteins, related microbial expression systems, and processes for making the IL-3 hybrids using the microbial expression systems.

The present invention provides human/mouse IL-3 hybrid polypeptides comprising hIL-3 which contains murine IL-3 oligopeptide substitutions, and may have biological activities similar to or better than those of hIL-3. The present invention includes IL-3 deletion mutants in which from 1 to 14 amino acids have been deleted from the N-terminus and from 1 to 14 amino acids have been deleted from the C-terminus of native human interleukin-3 and which also contain substitutions of murine IL-3 oligopeptides in the polypeptide sequence. Preferred h/m IL-3 hybrids of the present invention are (15-125) hIL-3 deletion mutants which have deletions of amino acids 1 to 14 at the N-terminus and 126 to 133 at the C-terminus and which also contain substitutions of murine amino acids or oligopeptides in the polypeptide sequence, and h/m IL-3 hybrid polypeptides having substantially the same structure and substantially the same activity.

As used herein, human interleukin-3 corresponds to the amino acid sequence (1-133) as depicted in FIG. 1 and (15-125) hIL-3 corresponds to the 15 to 125 amino acid sequence of the hIL-3 polypeptide.

The present invention also includes the DNA sequences which code for the IL-3 hybrid polypeptides of the present invention, DNAs which are substantially similar and perform substantially the same function and DNAs which differ from the DNAs encoding the IL-3 hybrids of the present invention only due to the degeneracy of the genetic code.

Included in the present invention are hIL-3 deletion mutant hybrids having murine amino acid substitutions which may function as IL-3 antagonists or as discreet antigenic fragments for the production of antibodies useful in immunoassay and immunotherapy protocols.

In addition to the use of IL-3 in vivo, it is envisioned that in vitro uses would include its ability to stimulate bone marrow and blood cell activation and growth before infusion into patients.

Antagonists of hIL-3 would be particularly useful in blocking the growth of certain cancer cells like AML, CML and certain types of B lymphoid cancers. Other conditions where antagonists would be useful include those in which certain blood cells are produced at abnormally high numbers or are being activated by endogenous ligands. Antagonists would effectively compete for ligands, presumably naturally occurring hematopoietins including and not limited to IL-3, GM CSF and IL-5, which would trigger or augment the growth of cancer cells by virtue of their ability to bind to the IL-3 receptor complex while intrinsic activation properties of the ligand are diminished.

BRIEF DESCRIPTION OF THE DRAWINGS

FIG. 1 is the human IL-3 gene for *E. coli* expression (pMON5873), encoding the polypeptide sequence shown of natural (wild type) human IL-3, plus an initiator methionine, as expressed in *E. coli*, with the amino acids numbered from the N-terminus of the natural hIL-3.

FIG. 2: ClaI to NsiI Replacement Fragment. FIG. 2 shows the nucleotide sequence of the replacement fragment used between the ClaI and NsiI sites of the hIL-3 gene. The codon choice used in the fragment corresponds to that found in highly expressed *E. coli* genes. Three new unique restriction sites, EcoRV, XhoI and PstI were introduced for the purpose of inserting synthetic gene fragments. The portion of the coding sequence shown encodes hIL-3 amino acids 20–70.

FIG. 3a and 3b shows the nucleotide and amino acid sequence of the gene in pMON5873 with the sequence extending from NcoI through HindIII. The codon choices used to encode amino acids 1–14 correspond to that found in highly expressed *E. coli* genes.

FIG. 6 shows the construction of plasmid vector pMON5853 which encodes [Met-(15–133) hIL-3 (Arg$^{129}$)].

FIG. 11 shows the sequence of (1–140) murine IL-3 (mIL-3).

FIG. 19 shows the location and relationship between the segment of hIL-3 deleted and the segment of mIL-3 inserted to form the human/murine IL-3 hybrid polypeptides of the present invention. The various murine substitutions which were used at different places on the hIL-3 polypeptide to make the h/m IL-3 hybrids are designated M1 through M13. In FIG. 19 the following segments of murine IL-3 (FIG. 11) are depicted as M1 through M13:

M1=(19–28)mIL-3=Ser Ile Val Lys Glu Ile Ile Gly Lys Leu Pro [SEQ ID NO:106]

Figure 4:
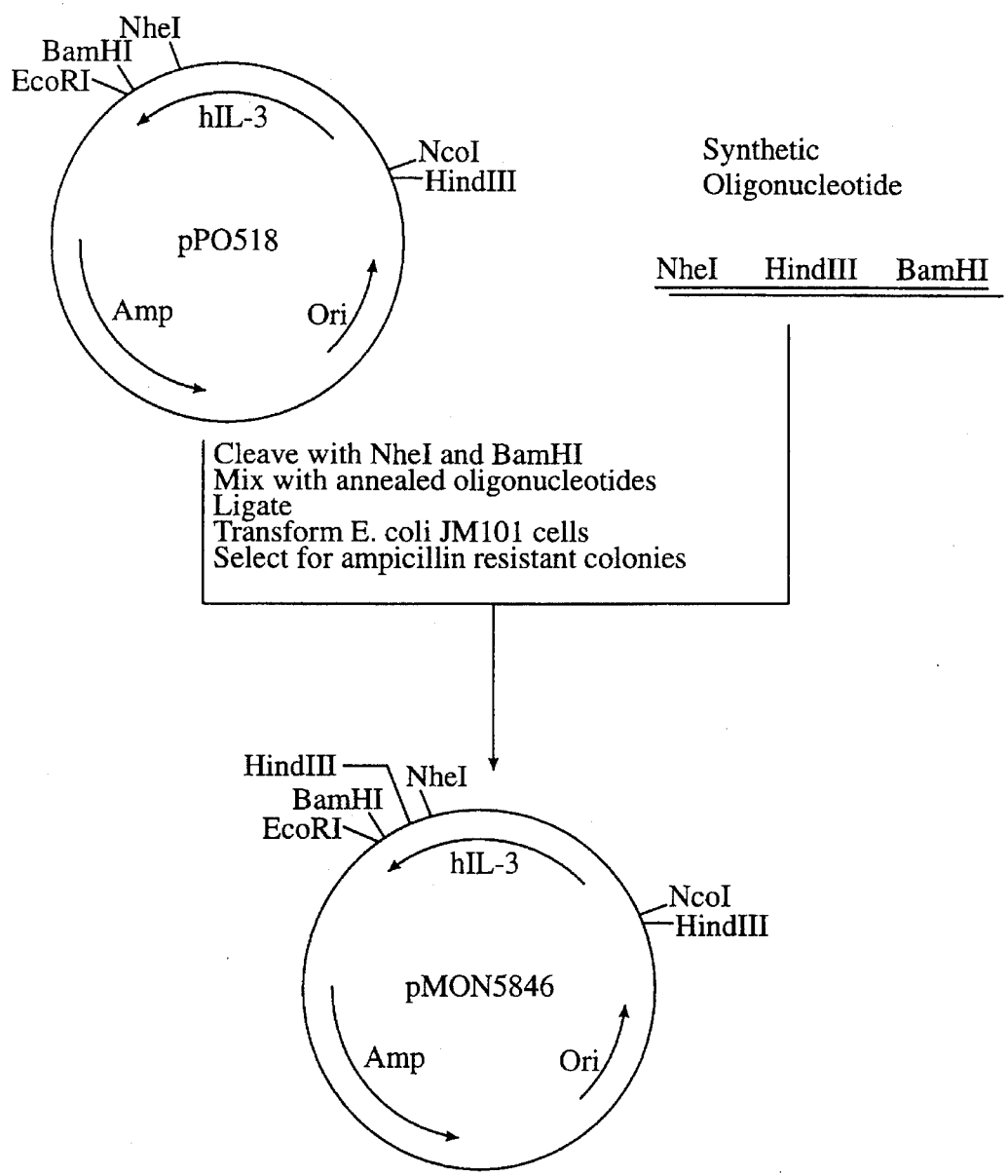
FIG. 4 shows the construction of the plasmid vector pMON5846 which encodes [Met-(1–133) hIL-3 (Arg$^{129}$)].

M2=deletion of "Gln Pro Pro Lev Pro Lev Lev" not found in mouse.

M3=(30–34)mIL-3=Glu Pro Glu Leu Lys [SEQ ID NO:115]

M4=(35–40)mIL-3=Thr Asp Asp Glu Gly Pro [SEQ ID NO:114]

M5=(41–46)mIL-3=Ser Leu Arg Ash Lys Ser [SEQ ID NO:110]

M6=(47–57)mIL-3=Phe Arg Arg Val Asn Leu Ser Lys Phe Val Glu [SEQ ID NO:111]

M7=(58–63)mIL-3=Ser Gln Gly Glu Val Asp [SEQ ID NO:112]

M8=(64–70)mIL-3=Pro Glu Asp Arg Tyr Val Ile [SEQ ID NO:116]

M9=(71–78)mIL-3 $Ser^{79}$=Lys Ser Asn Leu Gln Lys Leu Asn Ser [SEQ ID NO: 109]

M10=(80–87)mIL-3=Cys Leu Pro Thr Ser Ala Asn Asp [SEQ ID NO:108]

M11=(88–91)mIL-3=Ser Ala Leu Pro [SEQ ID NO:105]

M12=(92–96)mIL-3=Gly Val Phe Ile Arg [SEQ ID NO:107]

M13=(97–99)mIL-3=Asp Leu Asp [SEQ ID NO:117]

DETAILED DESCRIPTION OF THE INVENTION

The present invention relates to muteins of human interleukin-3 (hIL-3) in which oligopeptide segments of murine IL-3 have been substituted for segments of the human IL-3 polypeptide to form human/murine IL-3 (h/m IL-3) hybrids and to muteins which have substantially the same structure and substantially the same biological activity. Included in the invention are human/murine IL-3 hybrid polypeptides which have deletions of from 1 to 14 amino acids at the N-terminus, the C-terminus or at both the N-terminus and the C-terminus and which optionally may also have one or more additional amino acid substitutions in the polypeptide. Preferred muteins of the present invention are (15–125)hIL-3 deletion muteins which have deletions of amino acids 1 to 15 at the N-terminus and amino acids 126 to 133 at the C-terminus and which also contain substitutions of murine IL-3 amino acid segments in the (15–125)hIL-3 polypeptide sequence; and muteins having substantially the same structure and substantially the same biological activity.

As used herein human interleukin-3 corresponds to the amino acid sequence (1–133) as depicted in FIG. 1 and murine interleukin-3 corresponds to the amino acid sequence (1–140) as depicted in FIG. 11. Naturally occurring variants of hIL-3 polypeptide amino acids are also included in the present invention (e.g. proline rather than serine at position 8) as are variant hIL-3 molecules which are modified post-translationally (e.g. glycosylation).

The present invention also includes the DNA sequences which code for the human/murine IL-3 hybrid polypeptides as well as DNA sequences which are substantially similar and perform substantially the same function, and DNA sequences which differ from the DNAs encoding the h/m IL-3 hybrid polypeptides of the present invention only due to the degeneracy of the genetic code.

The present invention includes the DNA sequences coding for the human/mouse IL-3 hybrid muteins of the present invention; the oligonucleotide intermediates used to construct the mutant hybrid DNAs, and the polypeptides coded for by these oligonucleotides. These polypeptides may be useful as antagonists or as antigenic fragments for the production of antibodies useful in immunoassay and immunotherapy protocols.

The mutant h/m IL-3 hybrid polypeptides of the present invention may also have methionine, alanine, or methionine-alanine residues inserted at the N-terminus.

"Mutant amino acid sequence," "mutant protein" or "mutant polypeptide" refers to a polypeptide having an amino acid sequence which varies from a native sequence or is encoded by a nucleotide sequence intentionally made variant from a native sequence. "Mutant protein," "variant protein" or "mutein" means a protein comprising a mutant amino acid sequence and includes polypeptides which differ from the amino acid sequence of native hIL-3 due to amino acid deletions, substitutions, or both. "Native sequence" or "natural sequence" refers to an amino acid or nucleic acid sequence which is identical to a wild-type or native form of a gene or protein.

"Hybrid" refers to a molecule comprised of both human IL-3 and murine IL-3 components. "Hybrid sequence" refers to an amino acid or nucleic acid sequence which is comprised of both human IL-3 and murine IL-3 segments. "Hybrid polypeptide" or "hybrid protein" refers to a polypeptide comprising segments of both human IL-3 and murine IL-3 amino acid sequences.

Human IL-3 can be characterized by its ability to stimulate colony formation by human hematopoietic progenitor cells. The colonies formed include erythroid, granulocyte, megakaryocyte, granulocytic macrophages and mixtures thereof. Human IL-3 has demonstrated an ability to restore bone marrow function and peripheral blood cell populations to therapeutically beneficial levels in studies performed initially in primates and subsequently in humans (Gillio, A. P., et al. (1990); Ganser, A. A., et al. (1990); Falk, S., et al. (1991). Additional activities of hIL-3 include the ability to stimulate leukocyte migration and chemotaxis; the ability to prime human leukocytes to produce high levels of inflammatory mediators like leukotrienes and histamine; the ability to induce cell surface expression of molecules needed for leukocyte adhesion; and the ability to trigger dermal inflammatory responses and fever. Additional biological activities of hIL-3 include signal transduction and receptor binding. Hybrid IL-3 proteins of the present invention may exhibit useful properties such as having similar or greater biological activity when compared to native hIL-3 or by having improved half-life or decreased adverse side effects or a combination of these properties. They may also be useful as antagonists. IL-3 hybrid polypeptides which have little or no activity when compared to native hIL-3 may still be useful as antagonists, as antigens for the production of antibodies for use in immunology or immunotherapy, as genetic probes or as intermediates used to construct other useful hIL-3 muteins. Since hIL-3 functions by binding to its receptor(s) and triggering second messengers resulting in competent signal transduction, IL-3 hybrid proteins may be useful in helping to determine which specific amino acid sequences are responsible for these activities.

The novel IL-3 hybrid polypeptides of the present invention will preferably have at least one biological property of human IL-3 or of an IL-3 like growth factor and may have more than one IL-3 like biological property or an improved property. Such hIL-3 or IL-3 like biological properties may include one or more of the following biological characteristics and in vivo and in vitro activities.

One such property is the support of the growth and differentiation of progenitor cells committed to erythroid, lymphoid, and myeloid lineages. For example, in a standard human bone marrow assay, an IL-3 like biological property is the stimulation of granulocytic type colonies, megakaryocytic type colonies; monocyte/macrophage type colonies, and erythroid bursts. Other such properties are the interaction with early multipotential stem cells, the sustaining of the growth of pluripotent precursor cells; the property is the ability to stimulate chronic myelogenous leukemia (CML) cell proliferation, the stimulation of proliferation of mast cells, the ability to support the growth of various factor-dependent cell lines and/or the ability to stimulate colony formation and/or to stimulate increased histamine synthesis in spleen and bone marrow cultures. Other biological properties of IL-3 have been disclosed in the art.

Biological activity of hIL-3 and IL-3 hybrid proteins of the present invention is determined by DNA synthesis by human acute myelogenous leukemia blasts (AML).

One object of the present invention is to provide human/murine IL-3 hybrid polypeptides having similar or improved biological activity in relation to native hIL-3.

The human/murine IL-3 hybrid proteins of the present invention can have one or more consecutive amino acids deleted from the native hIL-3 amino acid sequence along with a substitution of a segment of murine IL-3 amino acids for some of the human IL-3 amino acids in the polypeptide sequence. Typically four or more amino acids are deleted from the N-terminus and/or the C-terminus of hIL-3. The more preferred h/m IL-3 hybrid muteins have deletions at the C-terminus or at both the N- and the C-terminus.

IL-3 hybrids of the present invention include mutant polypeptides comprising minimally amino acids residues 15 to 118 of hIL-3 with or without additional amino acid extensions to the N-terminus and/or C-terminus; having substitutions of murine IL-3 oligopeptide segments for segments of the hIL-3 polypeptide; retaining one or more biological activities of human IL-3; and, in addition, having improved side effect profile in comparison to native hIL-3 or native (15–125)hIL-3. Preferred h/m IL-3 hybrid proteins of the present invention comprise (15–125)hIL-3, in which amino acids 1–14 and 126–133 have been deleted from native hIL-3 and a segment of murine IL-3 has been substituted for a segment of the hIL-3 polypeptide. It has been found that the (15–125)hIL-3 mutant is more soluble than is (1–133)hIL-3 when expressed in the cytoplasm of E. coli and is better for secretion expression in E. coli.

When expressed in E. coli the above-mentioned IL-3 hybrid polypeptides may have Met inserted at the N-terminus. The above polypeptides which begin with amino acids (aa) 1 or aa 15 of hIL-3 may also be constructed with Met-Ala- at the N-terminus so that upon production of the protein in the cytoplasm the Met is cleaved off by methionine aminopeptidase leaving Ala at the N-terminus. These IL-3 hybrid polypeptides may also be expressed in E. coli by fusing a signal peptide to the N-terminus. This signal peptide is cleaved from the polypeptide as part of the secretion process. Secretion in E. coli can be used to obtain the correct amino acid at the N-terminus (e.g., $Asn_{15}$ in the (15–125) hIL-3 polypeptide) due to the precise nature of the signal peptidase. This is in contrast to the heterogeneity often observed at the N-terminus of proteins expressed intracellularly in E. coli.

The IL-3 hybrid polypeptides of the present invention may have hIL-3 or hIL-3 like activity. For example, they may possess one or more of the biological activities of native hIL-3 and may be useful in stimulating the production of hematopoietic cells by human or primate progenitor cells. The IL-3 hybrid proteins of the present invention and pharmaceutical compositions containing them may be useful in the treatment of conditions in which hematopoietic cell populations have been reduced or destroyed due to disease or to treatments such as radiation or chemotherapy.

hIL-3 muteins of the present invention may also be useful as antagonists which block the hIL-3 receptor by binding specifically to it and prevent binding of the agonist.

One potential advantage of h/m IL-3 hybrid deletion muteins of the present invention, particularly those which retain activity similar to or better than that of native hIL-3, is that a smaller amount may be used to produce the desired therapeutic effect. Pharmaceutical compositions containing h/m IL-3 hybrids of the present invention can be administered parenterally, intravenously, or subcutaneously. By using a truncated h/m IL-3 hybrid polypeptide, such as a (15–125)IL-3 hybrid, more of the active protein can be administered in a smaller dosage. This may reduce the number of treatments necessary to produce the desired therapeutic effect. The use of smaller amounts may also reduce the possibility of any potential antigenic effects or other possible undesirable side effects. The IL-3 hybrid proteins of the present invention may also be useful in the activation of stem cells or progenitors which have low receptor numbers.

As another aspect of the present invention, there is provided a novel method for producing the novel family of human/murine IL-3 hybrid proteins. The method of the present invention involves culturing a suitable cell or cell line, which has been transformed with a vector containing a DNA sequence coding for expression of a novel IL-3 hybrid polypeptide. Suitable cells or cell lines may be bacterial cells. For example, the various strains of E. coli are well-known as host cells in the field of biotechnology. One example of such cells are E. coli JM101 cells. Various strains of B. subtilis may also be employed in this method. Many strains of yeast cells known to those skilled in the art are also available as host cells for expression of the polypeptides of the present invention.

Also suitable for use in the present invention are mammalian cells, such as Chinese hamster ovary cells (CHO). General methods for expression of foreign genes in mammalian cells are reviewed in: Kaufman, R. J. (1987) High level production of proteins in mammalian cells, in *Genetic Engineering, Principles and Methods*, Vol. 9, J. K. Setlow, editor, Plenum Press, New York. An expression vector is constructed in which a strong promoter capable of functioning in mammalian cells drives transcription of a eukaryotic secretion signal peptide coding region, which is translationally fused to the coding region for the hIL-3 variant. For example, plasmids such as pcDNA I/Neo, pRc/RSV, and pRc/CMV (obtained from Invitrogen Corp., San Diego, Calif.) can be used. The eukaryotic secretion signal peptide coding region can be from the hIL-3 gene itself or it can be from another secreted mammalian protein (Bayne, M. L. et al. (1987) *Proc. Natl. Acad. Sci. USA* 84, 2638–2642. After construction of the vector containing the hIL-3 variant gene, the vector DNA is transfected into mammalian cells. Such cells can be, for example, the COS7, HeLa, BHK, CHO, or mouse L lines. The cells can be cultured, for example, in DMEM media (JRH Scientific). The hIL-3 variant secreted into the media can be recovered by standard biochemical approaches following transient expression 24–72 hours after transfection of the cells or after establishment of stable cell lines following selection for neomycin resistance. The selection of suitable mammalian host cells and methods for transformation, culture, amplification, screening and product production and purification are known in the art. See, e.g., Gething and Sambrook, *Nature*, 293:620–625 (1981), or alternatively, Kaufman et al, *Mol. Cell. Biol.*, 5(7):1750–1759 (1985) or Howley et al., U.S. Pat. No. 4,419,446. Another suitable mammalian cell line is the monkey COS-1 cell line. A similarly useful mammalian cell line is the CV-1 cell line.

Where desired, insect cells may be utilized as host cells in the method of the present invention. See, e.g. Miller et al, *Genetic Engineering*, 8:277–298 (Plenum Press 1986) and references cited therein. In addition, general methods for expression of foreign genes in insect cells using Baculovirus vectors are described in: Summers, M. D. and Smith, G. E. (1987)—A manual of methods for Baculovirus vectors and insect cell culture procedures, Texas Agricultural Experiment Station Bulletin No. 1555. An expression vector is constructed comprising a Baculovirus transfer vector, in which a strong Baculovirus promoter (such as the polyhedron promoter) drives transcription of a eukaryotic secretion signal peptide coding region, which is translationally fused to the coding region for the hIL-3 variant polypeptide. For example, the plasmid pVL-1392 (obtained from Invitrogen Corp., San Diego, Calif.) can be used. After construction of the vector carrying the hIL-3 variant gene, two micrograms of this DNA is cotransfected with one microgram of Baculovirus DNA (see Summers & Smith, 1987) into insect cells, strain SF9. Pure recombinant Baculovirus carrying the hIL-3 variant is used to infect cells cultured, for example, in Excell 401 serum-free medium (JRH Biosciences, Lenexa, Kans.). The hIL-3 variant secreted into the medium can be recovered by standard biochemical approaches.

Another aspect of the present invention provides plasmid DNA vectors for use in the method of expression of these novel human/murine IL-3 hybrid proteins. These vectors contain the novel DNA sequences described above which code for the novel polypeptides of the invention. Appropriate vectors which can transform microorganisms capable of expressing the IL-3 hybrid proteins include expression vectors comprising nucleotide sequences coding for the IL-3 hybrids joined to transcriptional and translational regulatory sequences which are selected according to the host cells used.

Vectors incorporating modified sequences as described above are included in the present invention and are useful in the production of the IL-3 hybrid polypeptides. The vector employed in the method also contains selected regulatory sequences in operative association with the DNA coding sequences of the invention and capable of directing the replication and expression thereof in selected host cells.

The human/mouse IL-3 hybrid proteins of the present invention may include IL-3 hybrid polypeptides having Met-, Ala- or Met-Ala- attached to the N-terminus. When the hybrid proteins are expressed in *E. coli*, polypeptides with and without Met attached to the N-terminus are obtained. The methionine can in some cases be removed by methionine aminopeptidase.

Amino terminal sequences of h/m IL-3 hybrid proteins made in *E. coli* were determined using the method described by Hunkapillar et al., (1983). It was found that IL-3 hybrid proteins made in *E. coli* from genes encoding Met-(1–133) hIL-3 were composed of three species: Met-Ala(1)-Pro(2)-, Ala(1)-Pro(2), Pro(2) found in a ratio of 5:4:1. Proteins produced from genes encoding Met-(15–125) hIL-3 were isolated as Met-(15–125) hIL-3. Proteins produced from genes encoding Met-Ala-(15–125) hIL-3 were produced as Ala-(15–125) hIL-3. The N-termini of proteins made in the cytoplasm of *E. coli* are affected by post-translational processing by methionine aminopeptidase (Ben-Bassat et al., 1987) and possibly by other peptidases.

One method of creating truncated hIL-3 mutein genes is to replace the portion of the coding sequence of hIL-3 in a plasmid with synthetic oligonucleotides that encode a shorter portion of the gene.

Pairs of complementary synthetic oligonucleotides encoding portions of the amino terminus of the hIL-3 gene can be made and annealed to each other. Such pairs would have protruding ends compatible with ligation to NcoI at one end. The NcoI site would include the codon for the initiator methionine. At the other end of oligonucleotide pairs, the protruding (or blunt) ends would be compatible with a restriction site that occurs within the amino terminal portion of the coding sequence of the hIL-3 gene. The DNA sequence of the oligonucleotide would encode sequence for amino acids of hIL-3 with the exception of those deleted from the sequence.

The NcoI site and the other restriction enzymes chosen should have recognition sites that occur only once in the DNA of the plasmid chosen. Plasmid DNA can be treated with the chosen restriction endonucleases then ligated to the annealed oligonucleotides. The ligated mixtures can be used to transform competent JM101 cells to resistance to an appropriate antibiotic. Single colonies can be picked and the plasmid DNA examined by restriction analysis and/or DNA sequencing to identify plasmids with truncated hIL-3 genes.

One example of a restriction enzyme which cleaves within the coding sequence of the hIL-3 gene is ClaI whose recognition site is at codons 20 and 21. The use of ClaI to cleave the sequence of hIL-3 requires that the plasmid DNA be isolated from an *E. coli* strain that fails to methylate adenines in the DNA at GATC recognition sites. This is because the recognition site for ClaI, ATCGAT, occurs within the sequence GATCGAT which occurs at codons 19, 20 and 21 in the hIL-3 gene. The A in the GATC sequence is methylated in most *E. coli* host cells. This methylation prevents ClaI from cleaving at that particular sequence. An example of a strain that does not methylate adenines is GM48 (Marinus, 1973).

The h/m IL-3 hybrids of the present invention may be useful in the treatment of diseases characterized by a decreased level of either myeloid, erythroid, lymphoid, or megakaryocyte cells of the hematopoietic system or combinations thereof. In addition, they may be used to activate mature myeloid and/or lymphoid cells. Among conditions susceptible to treatment with the polypeptides of the present invention is leukopenia, a reduction in the number of circulating leukocytes (white cells) in the peripheral blood. Leukopenia may be induced by exposure to certain viruses or to radiation. It is often a side effect of various forms of cancer therapy, e.g., exposure to chemotherapeutic drugs, and of infection or hemmorrhage. Therapeutic treatment of leukopenia with these hIL-3 mutant polypeptides of the present invention may avoid undesirable side effects caused by treatment with presently available drugs.

The h/m IL-3 hybrids of the present invention may be useful in the treatment of neutropenia and, for example, in the treatment of such conditions as aplastic anemia, cyclic neutropenia, idiopathic neutropenia, Chédiak-Higashi syndrome, systemic lupus erythematosus (SLE), leukemia, myelodysplastic syndrome and myelofibrosis.

Many drugs may cause bone marrow suppression or hematopoietic insufficiency. Examples of such drugs are AZT, DDI, alkylating agents and anti-metabolites used in chemotherapy, antibiotics such as chloramphenicol, penicillin and sulfa drugs, phenothiazones, tranquilizers such as meprobamate, and diuretics. The IL-3 hybrid proteins of the present invention may be useful in preventing or treating the bone marrow suppression or hematopoietic insufficiencies which often occur in patients treated with these drugs.

Hematopoietic insufficiencies may also occur as a result of viral, microbial or parasitic infections and as a result of treatment for renal disease or renal failure, e.g., dialysis. The h/m IL-3 hybrid polypeptides of the present invention may be useful in treating such hematopoietic insufficiencies.

The treatment of hematopoietic insufficiencies may include administration of the IL-3 hybrid or a pharmaceutical composition containing the IL-3 hybrid to a patient. The IL-3 hybrids of the present invention may also be useful for the activation and amplification of hematopoietic precursor cells by treating these cells in vitro with the muteins of the present invention prior to injecting the cells into a patient.

Various immunodeficiencies e.g., in T and/or B lymphocytes, or immune disorders, e.g., rheumatoid arthritis, may also be beneficially affected by treatment with the IL-3 hybrid polypeptides of the present invention. Immunodeficiencies may be the result of viral infections e.g. HTLVI, HTLVII, HTLVIII, severe exposure to radiation, cancer therapy or the result of other medical treatment. The h/m IL-3 hybrid polypeptides of the present invention may also be employed, alone or in combination with other hematopoietins, in the treatment of other blood cell deficiencies, including thrombocytopenia (platelet deficiency), or anemia. Other uses for these novel polypeptides are in the treatment of patients recovering from bone marrow transplants in vivo and ex vivo, and in the development of monoclonal and polyclonal antibodies generated by standard methods for diagnostic or therapeutic use.

Other aspects of the present invention are methods and therapeutic compositions for treating the conditions referred to above. Such compositions comprise a therapeutically effective amount of one or more of the h/m IL-3 hybrid muteins of the present invention in a mixture with a pharmaceutically acceptable carrier. This composition can be administered either parenterally, intravenously or subcutaneously. When administered, the therapeutic composition for use in this invention is preferably in the form of a pyrogen-free, parenterally acceptable aqueous solution. The preparation of such a parenterally acceptable protein solution, having due regard to pH, isotonicity, stability and the like, is within the skill of the art.

The dosage regimen involved in a method for treating the above-described conditions will be determined by the attending physician considering various factors which modify the action of drugs, e.g. the condition, body weight, sex and diet of the patient, the severity of any infection, time of administration and other clinical factors. Generally, a daily regimen may be in the range of 10–200 micrograms of non-glycosylated IL-3 hybrid protein per kilogram of body weight. This dosage regimen is referenced to a standard level of biological activity which recognizes that native IL-3 generally possesses an $EC_{50}$ at or about 10 picoMolar to 100 picoMolar in the AML proliferation assay described herein. Therefore, dosages would be adjusted relative to the activity of a given mutein vs. the activity of native (reference) IL-3, and it would not be unreasonable to note that dosage regimens may include doses as low as 0.1 microgram and as high as 1 milligram per kilogram of body weight per day. In addition, there may exist specific circumstances where dosages of IL-3 mutein would be adjusted higher or lower than the range of 10–200 micrograms per kilogram of body weight. These include co-administration with other CSF or growth factors; co-administration with chemotherapeutic drugs and/or radiation; the use of glycosylated IL-3 mutein; and various patient-related issues mentioned earlier in this section. As indicated above, the therapeutic method and compositions may also include co-administration with other human factors. A non-exclusive list of other appropriate hematopoietins, CSFs and interleukins for simultaneous or serial co-administration with the polypeptides of the present invention includes GM-CSF, CSF-1, G-CSF, Meg-CSF, M-CSF, erythropoietin (EPO), IL-1, IL-4, IL-2, IL-5, IL-6, IL-7, IL-8, IL-9, IL-10, IL-11, IL-12, IL-13, B-cell growth factor, B-cell differentiation factor and eosinophil differentiation factor, stem cell factor (SCF) also known as steel factor or c-kit ligand, or combinations thereof. The dosage recited above would be adjusted to compensate for such additional components in the therapeutic composition. Progress of the treated patient can be monitored by periodic assessment of the hematological profile, e.g., differential cell count, colony forming unit (CFU) assays, and the like.

Materials and methods for IL-3 Human/Mouse Hybrid Expression in *E. coli*

Unless noted otherwise, all specialty chemicals were obtained from Sigma Co., (St. Louis, Mo.). Restriction endonucleases, T4 poly-nucleotides kinase, *E. coli* DNA polymerase I large fragment (Klenow) and T4 DNA ligase and Mung Bean Nuclease were obtained from New England Biolabs (Beverly, Mass.).

*Escherichia coli* strains.

Strain JM101: delta lac, pro supE, thi, F'(traD36, rpoAB, lacI-Q, lacZdeltaM15) (Messing, 1979). This strain can be obtained from the American Type Culture Collection, accession number 33876. W3110 rpoH358 is a derivative of W3110 (Bachmann, 1972) and has been assigned ATCC accession number 55204. Strain GM48: dam-3, dcm-6, gal, ara, lac, thr, leu, tonA, tsx (Marinus, 1973) was used to make plasmid DNA that is not methylated at the sequence GATC.

Genes and plasmids:

The gene used for hIL-3 production in *E. coli* was obtained from British Biotechnology Incorporated, Cambridge, England, catalogue number BBG14. This gene is carried on a pUC based plasmid designated pP0518.

The plasmids used for production of hIL-3 in *E. coli* contain genetic elements whose use has been described (Olins et al., 1988; Olins and Rangwala, 1990). The replicon used is that of pBR327 which is maintained at a copy number of about 100 in the cell (Soberon et al., 1980). A gene encoding the beta-lactamase protein is present on the plasmids. This protein confers ampicillin resistance on the cell. This resistance serves as a selectable phenotype for the presence of the plasmid in the cell.

The transcription promoter was derived from the recA gene of *E. coli* (Sancar et al., 1980). This promoter, designated precA, includes the RNA polymerase binding site and the lexA repressor binding site (the operator). This segment of DNA provides high level transcription that is regulated even when the recA promoter is on a plasmid with the pBR327 origin of replication (Olins et al., 1988) incorporated herein by reference.

The ribosome binding site used is that from gene 10 of phage T7 (Olins et al., 1988). This is encoded in a 100 base pair (bp) fragment placed adjacent to precA. In the plasmids used herein, the recognition sequence for the enzyme NcoI (CCATGG) follows the g10-L. It is at this NcoI site that the hIL-3 genes are joined to the plasmid. It is expected that the nucleotide sequence at this junction will be recognized in mRNA as a functional start site for translation (Olins et al., 1988). The hIL-3 genes used were engineered to have a HindIII recognition site (AAGCTT) downstream from the coding sequence of the gene. At this HindIII site is a 514 base pair RsaI fragment containing the origin of replication of the single stranded phage f1 (Dente et al., 1983; Olins, et al., 1990) both incorporated herein by reference. A plasmid containing these elements is pMON2341. Another plasmid containing these elements is pMON5847 which has been deposited at the American Type Culture Collection, 12301 Parklawn Drive, Rockville, Md. 20852 under the accession number ATCC 68912.

Oligonucleotides were synthesized on Nucleotide Synthesizer model 380A or 380B from Applied Biosystems, Inc. (Foster City, Calif.). These were purified through a Nensorb column obtained from New England Nuclear (Boston, Mass.) using a PREP Automated Sample Processor obtained from DuPont, Co. (Wilmington, Del.).

Quantitation of synthetic oligonucleotides

Synthetic oligonucleotides were resuspended in water and quantitated by reading the absorbance at 260 nm on a Beckman DU40 Spectrophotometer (Irvine, Calif.) using a one centimeter by one millimeter quartz cuvette (Maniatis, 1982). The concentration was determined using an extinction coefficient of $1 \times 10^4$ (Voet et al., 1963; Mahler and Cordes, 1966). The oligonucleotides were then diluted to a desired concentration.

Quantitation of synthetic DNA fragments can also be achieved by adding 10 to 100 picomoles of DNA to a solution containing kinase buffer (25 mM Tris pH 8.0, 10 mM $MgCl_2$, 10 mM DTT and 2 mM spermidine). To the reaction mix is added ATP to 20 micromolar, ATP radiolabeled at the gamma phosphate (5000–10,0000 dpm/pmol) and 5 units of T4 polynucleotide kinase. Radiolabelled material is obtained from New England Nuclear (Boston, Mass.). The 10 microliter mixture is incubated at 37° C. for one hour. A 1 microliter aliquot of the mixture was chromatographed on DEAE paper (Whatman) in ammonium bicarbonate. The counts that remained at the origin were used to determine the concentration of the synthetic DNA.

Recombinant DNA methods

Isolation of plasmid DNA from *E. coli* cultures was performed as described (Birnboim and Doly, 1979). Some DNAs were purified by Magic™ columns, available from Promega (Madison, Wis.).

Purified plasmid DNA was treated with restriction endonucleases in the presence of 6.6 mM Tris pH 8.0, 6.6 mM $MgCl_2$, 50 mM NaCl and 5 mM dithiothreitol (DTT) for 1 hour at 37° C. or according to manufacturers instructions. Analysis of the DNA fragments produced by treatment with restriction enzymes was done by agarose or polyacrylamide gel electrophoresis. Agarose was used at a concentration of 1.0% in a Tris acetate running buffer (0.04M Tris-acetate, 0.001M EDTA). 8% polyacrylamide gels were run in 0.5 X Tris borate buffer (0.045M Tris, 0.045M boric acid, 1.25 mM EDTA).

DNA polymerase I, large fragment, Klenow enzyme was used according to manufacturers instructions to catalyze the addition of mononucleotides from 5' to 3' of DNA fragments which had been treated with restriction enzymes that leave protruding ends. The reactions were incubated at 65° C. for 10 minutes to heat inactivate the Klenow enzyme.

Mung Bean Nuclease was used according to manufacturer's instructions to remove single-stranded extensions from double-stranded DNA resulting in ligatable blunt ends. The endonuclease removes 5' extensions.

Reference: Kpwalski, D., Kroeker, W. D. and Laskowski, M., Sr. (1976) Biochemistry 15, 4457. McCutchan, T. F., Hansen, J. L., Dame, I. B. and Mullins, J. A. (1984) Science 225, 626–628.

The synthetic oligonucleotides were made without 5' or 3' terminal phosphates. In cases where such oligonucleotides were ligated end to end, the oligonucleotides were treated at a concentration of 10 picomoles per microliter with T4 polynucleotide kinase in the following buffer: 25 mM Tris, pH 8.0, 10 mM MgCl2, 10 mM dithiothreitol, 2 mM spermidine, 1 mM rATP. After incubation for 30 minutes at 37° C., the samples were incubated at 65° C. for five minutes to heat inactivate the kinase.

Synthetic oligonucleotides used were usually designed so that they would anneal in complementary pairs, often with protruding single stranded ends. To anneal the oligonucleotide pairs, both of the two complementary oligonucleotides were resuspended at a concentration of approximately 1 picomole per microliter in the following buffer: 6.6 mM Tris, pH 7.4, 6.6 mM MgCl2, 6.6 mM NaCl, 50 mM dithiothreitol. The samples were heated in a 100 ml beaker of boiling water and permitted to cool slowly to room temperature. The DNA in these annealed mixtures was used in ligation reactions.

Restriction fragments were isolated from agarose gels by inserting a DEAE membrane into the gel in front of the migrating DNA band. The DNA was then eluted from the DEAE membrane in 10 mM Tris, 1 mM EDTA, 1M NaCl at 55° C. To the solution of DNA fragment, two volumes of 95% ethanol were added. Samples were chilled on dry ice, centrifuged to collect the DNA and the pellets were dried in a Speed Vac concentrator from Savant Co. (Farmingdale, N.Y.). Ligations were performed using either purified fragments generated as described above or using plasmid DNA which had been treated with restriction enzymes. Ligation of these fragments was performed in the presence of T4 DNA ligase at 15° C. overnight in ligation buffer (6.6 mM Tris pH 7.5, 6.6 mM $MgCl_2$, 1 mM dithiothreitol, 0.4 mM rATP).

Recovery of recombinant plasmids from ligation mixes

*E. coli* JM101 cells were made competent to take up DNA. Typically, 20 to 100 ml of cells were grown in LB medium to a density of approximately 150 Klett units and then collected by centrifugation. The cells were resuspended in one half culture volume of 50 mM $CaCl_2$ and held at 4° C. for one hour. The cells were again collected by centrifugation and resuspended in one tenth culture volume of 50 mM $CaCl_2$. DNA was added to a 150 microliter volume of these cells, and the samples were held at 4° C. for 30 minutes. The samples were shifted to 42° C. for one minute, one milliliter of LB was added, and the samples were shaken at 37° C. for one hour. Cells from these samples were collected and spread on plates containing ampicillin to select for transformants. The plates were incubated overnight at 37° C. Single colonies were picked, grown in LB supplemented with ampicillin overnight at 37° C. with shaking. From these cultures DNA was isolated for restriction analysis.

Culture media

LB medium (Maniatis et al., 1982) was used for growth of cells for DNA isolation. M9 minimal medium supplemented with 1.0% casamino acids, acid hydrolyzed casein, Difco (Detroit, Mich.) was used for cultures in which recombinant IL-3 hybrid protein was produced. The ingredients in the M9 medium were as follows: 3 g/liter $KH_2PO_4$, 6 g/l $Na_2HOP_4$, 0.5 g/l NaCl, 1 g/l $NH_4Cl$, 1.2 mM $MgSO_4$, 0.025 mM $CaCl_2$, 0.25% glucose, 1% casamino acids, 0.1 ml/l trace minerals containing (per liter 108 g $FeCl_3 6 H_2O$, 4.0 g $ZnSO_4$ 7 $H_2O$, 7.0 g $CoCl_2$ $2H_2O$, 7.0 g $Na_2MoO_4$ $2H_2O$, 8.0 g $CuSO_4$ $5H_2O$, 2.0 g $H_3BO_3$, 5.0 g $MnSO_4$ $H_2O$, 100 ml concentrated HCl). Bacto agar was used for solid media and ampicillin was added to both liquid and solid LB media at 200 micrograms per milliliter.

DNA Sequence analysis

The nucleotide sequencing of plasmid DNA was performed using Sequenase™ polymerase according to the protocol of its supplier, Stratagene (La Jolla, Calif.). Some DNA sequences were determined using a Genesis 2000 sequencer obtained from DuPont (Wilmington, Del.) according to the methods of Prober et al. (1987) and Sanger et al. (1977).

Production of recombinant human/mouse IL-3 hybrids in *E. coli* with vectors employing the recA promoter

*E. coli* strains harboring the plasmids of interest were grown at 37° C. in M9 plus casamino acids medium with shaking in a Gyrotory water bath Model G76 from New Brunswick Scientific (Edison, N.J.). Growth was monitored (green 54 filter) with a Klett Summerson meter, Klett Mfg. Co. (New York, N.Y.). At a Klett value of approximately 150, an aliquot of the culture (usually one milliliter) was removed for protein analysis. To the remaining culture, nalidixic acid in 0.1N NaOH was added to a final concentration of 50 μg/ml. The cultures were shaken at 37° C. for three to four hours after addition of nalidixic acid. A high degree of aeration was maintained throughout the bacterial growth in order to achieve maximal production of the desired gene product. The cells were examined under a light microscope for the presence of refractile bodies (RBs). One milliliter aliquots of the culture were removed for analysis of protein content.

Analysis of protein content of *E. coli* cultures producing IL-3 hybrid polypeptides Bacterial cells from cultures treated as described above were collected from the medium by centrifugation. Aliquots of these cells were resuspended in SDS loading buffer (4X: 6 g SDS, 10 ml beta-mercaptoethanol, 25 ml upper Tris gel stock (0.5M Tris HCl pH 6.8, 0.4% SDS) brought to 50 ml with glycerol, 0.2% bromophenol blue was added) at a concentration of one microliter per Klett unit. These samples were incubated at 85° C. for five minutes and vortexed. Five or ten microliter aliquots of these samples were loaded on 15% polyacrylamide gels prepared according to the method of Laemmli (1970). Protein bands were visualized by staining the gels with a solution of acetic acid, methanol and water at 5:1:5 ratio to which Coomassie blue had been added to a final concentration of 1%. After staining, the gels were washed in the same solution without the Coomassie blue and then washed with a solution of 7% acetic acid, 5% methanol. Gels were dried on a gel drier Model SE1160 obtained from Hoeffer (San Francisco, Calif.). The amount of stained protein was measured using a densitometer obtained from Joyce-Loebl (Gateshead, England). The values obtained were a measure of the amount of the stained IL-3 hybrid protein compared to the total of the stained protein of the bacterial cells.

Fractionation of *E. coli* cells producing IL-3 hybrid proteins

Cells from *E. coli* cultures harboring plasmids that produce IL-3 hybrid proteins were induced with nalidixic acid. After three hours, the IL-3 hybrid proteins accumulated in refractile bodies. The first step in purification of the IL-3 hybrid polypeptides was to sonicate cells. Aliquots of the culture were resuspended from cell pellets in sonication buffer: 10 mM Tris, pH 8.0, 1 mM EDTA, 50 mM NaCl and 0.1 mM PMSF. These resuspended cells were subjected to several repeated sonication bursts using the microtip from a Sonicator cell disrupter, Model W-375 obtained from Heat Systems-Ultrasonics Inc. (Farmingdale, N.Y.). The extent of sonication was monitored by examining the homogenates under a light microscope. When nearly all of the cells had been broken, the homogenates were fractionated by centrifugation. The pellets, which contain most of the refractile bodies, are highly enriched for IL-3 hybrid polypeptides.

Methods: Extraction, Refolding and Purification of Interleukin-3 (IL-3) Human/Mouse Hybrids Expressed as Refractile Bodies in *E. coli*

Extraction of refractile bodies (RB's):

For each gram of RB's (and typically one gram is obtained from a 300 ml *E. Coli* culture), 5 ml of a solution containing 6M guanidine hydrochloride (GnHCl), 50 mM 2-N-cyclohexylaminoethanesulfonic acid (CHES) pH 9.5 and 20 mM dithiothreitol (DTT) was added. The RB's were extracted with a Bio-Homogenizer for 15–30 seconds and gently rocked for 2 hours at 5 degrees centigrade (5° C.) to allow the protein to completely reduce and denature.

Refolding of the IL-3 hybrid polypeptides:

The protein solution was transferred to dialysis tubing (1000 molecular weight cut-off) and dialyzed against at least 100 volumes of 4M GnHCl–50 mM CHES pH 8.0. The dialysis was continued overnight at 5° C. while gently stirring. Subsequently dialysis was continued against at least 100 volumes of 2M GnHCl–50 mM CHES pH 8.0 and dialyzed overnight at 5° C. while gently stirring.

Purification of the IL-3 hybrid polypeptides:

The protein solution was removed from the dialysis tubing and acidified by the addition of 40% acetonitrile ($CH_3CN$)–0.2% trifluoroacetic acid (TFA) to a final concentration of 20% $CH_3CN$–0.1% TFA. This was centrifuged (16,000×g for 5 minutes) to clarify and the supernatant was loaded onto a Vydac C-18 reversed phase column (10×250 mm) available from Vydac (Hesperia, Calif.) previously equilibrated in 20% CH3CN—0.1% TFA. The column was eluted with a linear gradient (0.2% $CH_3CN$/minute) between 40–50% $CH_3CN$–0.1% TFA at a flow rate of 3 ml/minute while collecting 1.5 ml fractions. The fractions were analyzed by polyacrylamide gel electrophoresis (SDS-PAGE) and the appropriate fractions pooled. The pooled material was dried by lyophilization or in a Speed Vac concentrator. The dry powder was reconstituted with 10 mM ammonium bicarbonate pH 7.5, centrifuged (16,000×g for 5 minutes) to clarify and assayed for protein concentration by the method of Bradford (1976) with bovine serum albumin as the standard. Such protein can be further analyzed by additional techniques such as, SDS-PAGE, electrospray mass spectrometry, reverse phase HPLC, capillary zone electrophoresis, amino acid composition analysis, and ELISA (enzyme-linked immunosorbent assay).

In some cases, additional protein purification was performed. The dried powder from the initial HPLC chromatography was reconstituted in 20 mM sodium acetate–50 mM sodium chloride pH 5.5 and centrifuged (15,000×g for five minutes) to clarify. Discard the pellet and charge the supernatant onto Fast-S cation exchange resin (Pharmacia) previously equilibrated in 20 mM sodium acetate-50mM sodium chloride pH 5.5. Wash the resin with five column volumes (C.V.) of 20 mM sodium acetate–50 mM sodium chloride pH 5.5 and five C.V. of 20 mM sodium acetate–100 mM sodium chloride pH 5.5. Elute the variant from the resin with five C.V. of 20 mM sodium acetate–300 mM sodium chloride pH 5.5. Charge the eluate back onto the rpHPLC column and elute the variant with a linear gradient (0.2% $CH_3CN$/minute) between 40–50% $CH_3CN$-0.1% TFA previously described. Analyze the fractions by polyacrylamide gel electrophoresis for purity and pool the appropriate fractions and continue as described above.

AML Proliferation Assay for Bioactive Human Interleukin-3

Cells. The factor-dependent cell line AML 193 was obtained from the American Type Culture Collection (ATCC, Rockville, Md.). This cell line, established from a patient with acute myelogenous leukemia, is a growth factor dependent cell line which displayed enhanced growth in GM/CSF supplemented medium (Lange, B., et al., (1987); Valtieri, M., et al., (1987)). The ability of AML 193 cells to proliferate in the presence of human IL-3 has also been documented. (Santoli, D., et al., (1987)). A cell line variant was used, AML 193 1.3, which was adapted for long term growth in hIL-3 by washing out the factors and starving the cytokine dependent AML 193 cells for growth factors for 24 hours. The cells were then replated at 1×105 cells/well in a 24 well plate in media containing 100 U/ml hIL-3. It took approximately 2 months for the cells to grow rapidly in hIL-3.

AML 193 1.3 cells were washed 6 times in cold Hanks balanced salt solution (HBSS, Gibco, Grand Island, N.Y.) by centrifuging cell suspensions at 250×g for 10 minutes followed by decantation of supernatant. Pelleted cells were resuspended in HBSS and the procedure was repeated until six wash cycles were completed. Cells washed six times by this procedure were resuspended in tissue culture medium at a density ranging from $2 \times 10^5$ to $5 \times 10^5$ viable cells/ml. This medium was prepared by supplementing Iscove's modified Dulbecco's Medium (IMDM, Hazleton, Lenexa, Kans.) with albumin, transferrin, lipids and 2-mercaptoethanol. Bovine albumin (Boehringer-Mannheim, Indianapolis, Ind.) was added at 500 μg/ml; human transferrin (Boehringer-Mannheim, Indianapolis, Ind.) was added at 100 μg/ml; soybean lipid (Boehringer-Mannheim, Indianapolis, Ind.) was added at 50 μg/ml; and 2-mercaptoethanol (Sigma, St. Louis, Mo.) was added at $5 \times 10^{-5}$ M.

Two-fold serial dilutions of human interleukin-3 or interleukin-3 hybrid protein (hIL-3 mutein) were made in triplicate series in tissue culture medium supplemented as stated above in 96 well Costar 3596 tissue culture plates. Each well contained 50 μl of medium containing hIL-3 or IL-3 variant protein once serial dilutions were completed. Control wells contained tissue culture medium alone (negative control). AML 193 1.3 cell suspensions prepared as above were added to each well by pipetting 50 μl (2.5×104 cells) into each well. Tissue culture plates were incubated at 37° C. with 5% $CO_2$ in humidified air for 3 days. On day 3, 0.5 uCi $^3$H-thymidine (2 Ci/mM, New England Nuclear, Boston, Mass.) was added in 50 μl of tissue culture medium. Cultures were incubated at 37° C. with 5% $CO_2$ in humidified air for 18–24 hours. Cellular DNA was harvested onto glass filter mats (Pharmacia LKB, Gaithersburg, Md.) using a TOMTEC cell harvester (TOMTEC, Orange, Conn.) which utilized a water wash cycle followed by a 70% ethanol wash cycle. Filter mats were allowed to air dry and then placed into sample bags to which scintillation fluid (Scintiverse II, Fisher Scientific, St. Louis, Mo. or BetaPlate Scintillation Fluid, Pharmacia LKB, Gaithersburg, Md.) was added. Beta emissions of samples from individual tissue culture wells were counted in a LKB Betaplate model 1205 scintillation counter (Pharmacia LKB, Gaithersburg, Md.) and data was expressed as counts per minute of $^3$H-thymidine incorporated into cells from each tissue culture well. Activity of each human interleukin-3 preparation or interleukin-3 hybrid preparation was quantitated by measuring cell proliferation ($^3$H-thymidine incorporation) induced by graded concentrations of hIL-3 or IL-3 variant. Typically, concentration ranges from 1 pM–$10^5$ pM are quantitated in these assays. Activity is determined by measuring the dose of hIL-3 or IL-3 hybrid which provides 50% of maximal proliferation [$EC_{50}$=0.5×(maximum average counts per minute of $^3$H-thymidine incorporated per well among triplicate cultures of all concentrations of IL-3 tested—background proliferation measured by $^3$H-thymidine incorporation observed in triplicate cultures lacking IL-3]. This $EC_{50}$ value is also equivalent to 1 unit of bioactivity. Every assay was performed with native interleukin-3 as a reference standard so that relative activity levels could be assigned.

Relative biological activities of IL-3 hybrid polypeptides of the present invention are shown in Table 1. The Relative Biological Activity represents the average of replicated assays.

Receptor Binding Assay

The cytokine-dependent human acute myelogenous leukemia cell line AML 193 was obtained from ATCC, subcloned and selected for its ability to proliferate in response to hIL-3. These cells were further selected using biotin conjugated hIL-3 and FITC-avidin for repetitive fluorescence activated cell sorting (FACS) and were designated AML 193 1.3.9. This line was grown in IMDM supplemented with 5% FBS and 40 μM beta-mercaptoethanol and human IL-3 (1 to 4 ng/mL). The HL-60 cell line was obtained from ATCC and grown in RPMI 1640, 10% FBS and 40 μM beta-mercaptoethanol. Ligand for IL-3 receptor assays was derived from an E. coli expression vector encoding full length hIL-3 molecule (amino acids 1 to 133) having a 14 amino acid N-terminal extension. (Met-Ala-Tyr-Pro-Glu-Thr-Asp-Tyr-Lys-Asp-Asp-Asp-Lys-[SEQ ID NO: 119]; designated as pMON 5966, est. MW 16,976). This construct contained two additional tyrosines which were essential for iodination to high-specific radioactivity without loss of biological activity. This ligand was radiolabeled with iodine-125 using an insoluble lactoperoxidase method (®Enzymobeads) and used following HPLC purification. The bioactivity of labelled pMON 5966 was determined in the AML 193 cell proliferation assay and was found to be comparable to the activity of native hIL-3. Ligand for GM-CSF receptor assays was prepared by radiolabelling native GM-CSF with iodine-125 using the IODO-GEN method (Pierce Chemical) according to manufacturer's specifications.

For IL-3 receptor assays, AML 193 1.3.9 cells were incubated overnight in medium without growth factor. On the day of the assay the cells were washed 3 times with Hanks balanced salt solution, resuspended in assay buffer (IMDM, 5% FBS, 40 μM 2-ME and 0.1% BSA) and counted using a hemacytometer. Assay tubes contained the test compounds or inhibitors under study, 0.2% sodium azide, iodinated hIL-3 ligand (pMON 5966), 5–10×$10^6$ cells, and buffer in a total volume of 100 μL. Unlabelled hIL-3 (250 nM) was used to define non-specific binding, and each assay point was set up in triplicate. After incubation with gentle orbital agitation at 200 rpm for two hours at room temperature, 1 mL of ice-cold medium was added and the binding reaction was immediately terminated by centrifugation. The supernatant was removed by aspiration, and the tip of the tube containing the cell pellet was cut off and counted in a Micromedic gamma counter. Receptor Binding results are shown in Table 1.

TABLE 1

BIOLOGICAL ACTIVITY OF IL-3 HYBRID MUTEINS

| Plasmid Code | Polypeptide Sequence | Growth Factor Activity | Leukotriene Stimulating Activity | IL-3 Receptor Binding Activity |
|---|---|---|---|---|
| Reference (1-133)hIL-3 | | 1.00 | 1.00 | 1.00 |
| pMON5979 | SEQ ID NO: 64 | 7.94 | 0.46 | 1.21 |
| pMON5960 | SEQ ID NO: 65 | 0.13 | 0.10 | ≦0.01 |
| pMON5961 | SEQ ID NO: 66 | 0.50 | 3.63 | 1.05 |
| pMON5962 | SEQ ID NO: 67 | 1.26 | 10.72 | 0.81 |
| pMON5963 | SEQ ID NO: 68 | 5.01 | 12.88 | 1.32 |
| pMON5968 | SEO ID NO: 69 | 0.06 | 0.59 | 0.25 |
| pMON5970 | SEQ ID NO: 70 | 0.04 | ≦0.01 | ≦0.01 |
| pMON5972 | SEO ID NO: 71 | 0.20 | 0.15 | 0.08 |
| pMON5973 | SEQ ID NO: 72 | 0.20 | ≦0.01 | N.D. |
| pMON5974 | SEQ ID NO: 73 | 0.08 | ≦0.01 | ≦0.01 |
| pMON5975 | SEQ ID NO: 74 | 0.04 | ≦0.01 | ≦0.01 |
| pMON5977 | SEQ ID NO: 75 | 3.98 | 0.31 | 0.19 |
| pMON5980 | SEQ ID NO: 76 | 0.03 | ≦0.01 | ≦0.01 |

*Growth factor activity, leukotriene stimulating activity, and IL-3 receptor binding activity are relative to the activity of native hIL-3. Activity is expressed as Relative Biological Activity.

The following test is used to measure IL-3 mediated sulfidoleukotriene release from human mononuclear cells.

IL-3 mediated sulfidoleukotriene release from human mononuclear cells

Fifty mls of heparin-containing human blood were collected and layered onto an equal volume of Ficoll-Paque (Pharmacia #17-0840-02) ready to use medium (density 1.077 g/ml.). The Ficoll should be warmed to room temperature prior to use and clear 50 ml polystyrene tubes should be utilized. The Ficoll gradient was spun at 300×g for 35 minutes at room temperature using a H1000B rotor in a Sorvall RT6000B refrigerated centrifuge. The band containing the mononuclear cells was carefully removed, the volume adjusted to 50 mls with Dulbecco's phosphate-buffered saline (Gibco Laboratories cat. #310-4040PK), spun at 350×g for 10 minutes at room temperature and the supernatant was carefully removed. The cell pellet was washed twice, 350×g, 10 min. room temperature with room temperature HACM Buffer [20 mM Hepes (Sigma #H-3375), 125 mM NaCl (Fisher #S271–500), 5 mM KCl (Sigma #P-9541), 0.5 mM glucose (Sigma #G-5000),0.025% Human Serum Albumin (Calbiochem #126654). The cells were resuspended in HACM Buffer, HA buffer supplemented with 5 mM $CaCl_2$ (Fisher #C79–500) and 5 mM $MgCl_2$ (Fisher #M-33), at a concentration of $1 \times 10^6$ cells/ml. and 180 µl were transferred into each well of 96 well tissue culture plates. The cells were primed by adding 10 µls of a 20× stock of various concentrations of cytokine to each well (typically 100000, 20000, 4000, 800, 160, 32, 6.4, 1.28, 0 fM IL3). The cells were incubated for 15 minutes at 37° C. and 5% $CO_2$. Sulfidoleukotriene release was activated by the addition of 10 uls. of 20× (400 nM) fmet-leu-phe (Calbiochem #344252) (final concentration in wells 50 nM) and incubated for 15 minutes at 37° C. and 5% $CO_2$. The plates were spun at 350×g at 4° C. for 20 minutes. The supernatants were removed and assayed for sulfidoleukotrienes using Cayman's Leukotriene $C_4$ EIA kit (Cat. #420211) according to manufacturers' directions. Native (15–125)hIL-3 was run as a standard control in each assay on each plate.

Table 2 lists the sequences of some oligonucleotides used in making the IL-3 hybrids of the present invention.

Table 3 lists the amino acid sequence of native Met-(15–125)hIL-3 (Protein Sequence #9) Met-Ala-(15–125)hIL-3(Protein Sequence #16), Met-(15–125)hIL-3($Ala^{101}$)(Protein Sequence #1), and the amino acid sequences of some human/murine IL-3 polypeptides of the present invention.

Table 4 lists the nucleotide sequences of some DNA sequences which encode mutant polypeptides of the present invention.

TABLE 2

OLIGONUCLEOTIDES

OLIGO #1 Length: 58
GCCGGAAGAC CGTTACGTTA TCGAATCCAT CCTGAAAAAC CTGCTGCCGT
GCCTGCCG [SEQ ID NO:28]
OLIGO #2 Length: 66
CTAGCGGCAG GCACGGCAGC AGGTTTTTCA GGATGGATTC GATAACGTAA
CGGTCTTCCG GCTGCA [SEQ ID NO:29]
OLIGO #3 Length: 58
CTAGCCACGG CCGCATCCGC TCTGCCGCCA ATCCATATCA
AGGACGGTGA CTGGAATG [SEQ ID NO:30]
OLIGO #4 Length: 58
AATTCATTCC AGTCACCGTC CTTGATATGG ATTGGCGGCA
GAGCGGATGC GGCCGTGG [SEQ ID NO:31]
OLIGO #5 Length: 58
CTAGCCACGG CCGCACCGAC GCGTCATGGT GTTTTCATCC
GTGACGGTGA CTGGAATG [SEQ ID NO:32]
OLIGO #6 Length: 58
AATTCATTCC AGTCACCGTC ACGGATGAAA ACACCATGAC
GCGTCGGTGC GGCCGTGG [SEQ ID NO:33]
OLIGO #7 Length: 52
CTAGCCACGG CCGCACCGAC GCGTCATCCA ATCCATATCA
AGGACCTGGA CG [SEQ ID NO:34]
OLIGO #8 Length: 52
AATTCGTCCA. GGTCCTTGAT ATGGATTGGA TGACGCGTCG
GTGCGGCCGT GG [SEQ ID NO:35]
OLIGO #9 Length: 45

TABLE 2-continued

OLIGONUCLEOTIDES

| | | | |
|---|---|---|---|
| TCAGCAATTA | AAAGCAACCT | GCAGAAGCTC | AACTCCTGTC |
| TGCCG [SEQ ID NO:36] | | | |

OLIGO #10 Length: 53
| | | | |
|---|---|---|---|
| CTAGCGGCAG | ACAGGAGTTG | AGCTTCTGCA | GGTTGCTTTT |
| AATTGCTGAT | GCA [SEQ ID NO:37] | | |

OLIGO #11 Length: 58
| | | | |
|---|---|---|---|
| ACCTCCGCTA | ACGATCCGAC | GCGTCATCCA | ATCCATATCA |
| AGGACGGTGA | CTGGAACG [SEQ ID NO:38] | | |

OLIGO #12 Length: 62
| | | | |
|---|---|---|---|
| AATTCGTTCC | AGTCACCGTC | CTTGATATGG | ATTGGATGAC |
| GCGTCGGATC | GTTAGCGGAG | GT [SEQ ID NO:39] | |

OLIGO #13 Length: 34
| | | | |
|---|---|---|---|
| TCCCTGCGTA | ACAAATCCCT | TCGTCGTCCA | AACC [SEQ ID NO:40] |

OLIGO #14 Length: 38
| | | | |
|---|---|---|---|
| TCGAGGTTTG | GACGACGAAG | GGATTTGTTA | CGCAGGGA [SEQ ID NO:41] |

OLIGO #15 Length: 75
| | | | |
|---|---|---|---|
| ATCCTGATGG | AAAATAACTT | CCGTCGTGTT | AACCTCTCCA |
| AATTCGTTGA | AGCTGTCAAG | TCTCTGCAGA | ATGCA [SEQ ID NO:42] |

OLIGO #16 Length: 71
| | | | |
|---|---|---|---|
| TTCTGCAGAG | ACTTGACAGC | TTCAACGAAT | TTGGAGAGGT |
| TAACACGACG | GAAGTTATTT | TCCATCAGGA | T [SEQ ID NO:43] |

OLIGO #17 Length: 41
| | | | |
|---|---|---|---|
| TCGAGGCATT | CAACCGTTCC | CAGGGTGAAG | TTGACAATGC  A [SEQ ID NO:44] |

OLIGO #18 Length: 33
| | | | |
|---|---|---|---|
| TTGTCAACTT | CACCCTGGGA | ACGGTTGAAT | GCC [SEQ ID NO:45] |

OLIGO #19 Length: 58
| | | | |
|---|---|---|---|
| CGATGAAATC | ATCACCCACC | TGAAGGACTT | CAACAACCTC |
| AATGGTGAAG | ACCAAGAT [SEQ ID NO:46] | | |

OLIGO #20 Length: 56
| | | | |
|---|---|---|---|
| ATCTTGGTCT | TCACCATTGA | GGTTGTTGAA | GTCCTTCAGG |
| TGGGTGATGA | TTTCAT [SEQ ID NO:47] | | |

OLIGO #21 Length: 48
| | | | |
|---|---|---|---|
| CCGCTGCCGC | TGCTGGACTT | CAACAACCTC | ACCGACGACG |
| AAGGTCCG [SEQ ID NO:48] | | | |

OLIGO #22 Length: 40
| | | | |
|---|---|---|---|
| CGGACCTTCG | TCGTCGGTGA | GGTTGTTGAA | GTCCAGCAGC [SEQ ID NO:49] |

OLIGO #23 Length: 31
| | | | |
|---|---|---|---|
| CGATCAAATC | ATCACCCACC | TGAAGCAGCC | A [SEQ ID NO:50] |

OLIGO #24 Length: 37
| | | | |
|---|---|---|---|
| GGCTGCGGTG | GCTGCTTCAG | GTGGGTGATG | ATTTCAT [SEQ ID NO:51] |

OLIGO #25 Length: 48
| | | | |
|---|---|---|---|
| CCGCTGCCGC | TGCTGGAACC | GGAACTGAAA | AATGGTGAAG |
| ACCAAGAT [SEQ ID NO:52] | | | |

OLIGO #26 Length: 40
| | | | |
|---|---|---|---|
| ATCTTGGTCT | TCACCATTTT | TCAGTTCCGG | TTCCAGCAGC [SEQ ID NO:53] |

OLIGO #27 Length: 55
| | | | |
|---|---|---|---|
| CATGGCTAAC | TGCTCTTCCA | TCGTTAAAGA | AATCATCGGT |
| AAACTGCCGC | AGCCA [SEQ ID NO:54] | | |

OLIGO #28 Length: 45
| | | | |
|---|---|---|---|
| CGGCAGTTTA | CCGATGATTT | CTTTAACGAT | GGAAGAGCAG |
| TTAGC [SEQ ID NO:55] | | | |

OLIGO #29 Length: 48
| | | | |
|---|---|---|---|
| CCGCTGCCGC | TGCTGGACTT | CAACAACCTC | AATGGTGAAG |
| ACCAAGAT [SEQ ID NO:56] | | | |

OLIGO #30 Length: 54
| | | | |
|---|---|---|---|
| ATCTTGGTCT | TCACCATTGA | GGTTGTTGAA | GTCCAGCAGC |
| GGCAGCGGTG | GCTG [SEQ ID NO:57] | | |

OLIGO #31* Length: 61
| | | | |
|---|---|---|---|
| CGTAGAAATC | ATCACCCACC | TGAAGCAGCC | ACCGCTGCCG |
| CTGCTGGACT | TCAACAACCT | C [SEQ ID NO:58] | |

OLIGO #32* Length: 53
| | | | |
|---|---|---|---|
| GTTGAAGTCC | AGCAGCGGCA | GCGGTGGCTG | CTTCAGGTGG |
| GTGATGATTT | CAT [SEQ ID NO:59] | | |

OLIGO #33* Length: 52
| | | | |
|---|---|---|---|
| AATGGTGAAG | ACCAAGATAT | CCTGATGGAA | AATAACCTTC |
| GTCGTCCAAA | CC [SEQ ID NO:60] | | |

OLIGO #34* Length: 62
| | | | |
|---|---|---|---|
| TCGAGGTTTG | GACGACGAAG | GTTATTTTCC | ATCAGGATAT |
| CTTGGTCTTC | ACCATTGAGG | TT [SEQ ID NO:61] | |

OLIGO #35* Length: 41
| | | | |
|---|---|---|---|
| TCGAGGCATT | CAACCGTGCT | GTCAAGTCTC | TGCAGAATGC |
| A [SEQ ID NO:62] | | | |

OLIGO #36* Length: 33
| | | | |
|---|---|---|---|
| TTCTGCAGAG | ACTTGACAGC | ACGGTTGAAT | GCC [SEQ ID NO:63] |

*Oligonucleotides 31 to 36 were used to make the Cla-Nsi replacement fragment shown in FIG. 2.

TABLE 3

POLYPEPTIDES pMON5976 (Met-15-125hIL-3 ALA 101)
Protein sequence #1

| Met | Asn | Cys | Ser | Asn | Met | Ile | Asp | Glu | Ile | Ile | Thr | His | Leu | Lys |
|---|---|---|---|---|---|---|---|---|---|---|---|---|---|---|
| Gln | Pro | Pro | Leu | Pro | Leu | Leu | Asp | Phe | Asn | Asn | Leu | Asn | Gly | Glu |
| Asp | Gln | Asp | Ile | Leu | Met | Glu | Asn | Asn | Leu | Arg | Arg | Pro | Asn | Leu |
| Glu | Ala | Phe | Asn | Arg | Ala | Val | Lys | Ser | Leu | Gln | Asn | Ala | Ser | Ala |
| Ile | Glu | Ser | Ile | Leu | Lys | Asn | Leu | Leu | Pro | Cys | Leu | Pro | Leu | Ala |
| Thr | Ala | Ala | Pro | Thr | Arg | His | Pro | Ile | His | Ile | Lys | Ala | Gly | Asp |
| Trp | Asn | Glu | Phe | Arg | Arg | Lys | Leu | Thr | Phe | Tyr | Leu | Lys | Thr | Leu |
| Glu | Asn | Ala | Gln | Ala | Gln | Gln | [SEQ ID NO:19] | | | | | | | | pMON5979 (Met-15-125hIL-3 ALA 101) having an M8 substitution.
Protein sequence #2

| Met | Asn | Cys | Ser | Asn | Met | Ile | Asp | Glu | Ile | Ile | Thr | His | Leu | Lys |
|---|---|---|---|---|---|---|---|---|---|---|---|---|---|---|
| Gln | Pro | Pro | Leu | Pro | Leu | Leu | Asp | Phe | Asn | Asn | Leu | Asn | Gly | Glu |
| Asp | Gln | Asp | Ile | Leu | Met | Glu | Asn | Asn | Leu | Arg | Arg | Pro | Asn | Leu |
| Glu | Ala | Phe | Asn | Arg | Ala | Val | Lys | Ser | Leu | Gln | Pro | Glu | Asp | Arg |
| Tyr | Val | Ile | Glu | Ser | Ile | Leu | Lys | Asn | Leu | Leu | Pro | Cys | Leu | Pro |
| Leu | Ala | Thr | Ala | Ala | Pro | Thr | Arg | His | Pro | Ile | His | Ile | Lys | Ala |
| Gly | Asp | Trp | Asn | Glu | Phe | Arg | Arg | Lys | Leu | Thr | Phe | Tyr | Leu | Lys |
| Thr | Leu | Glu | Asn | Ala | Gln | Ala | Gln | Gln | [SEQ ID NO:64] | | | | | | pMON5941 (Met-15-125hIL-3 Ala 101)
Protein sequence #3

| Met | Asn | Cys | Ser | Asn | Met | Ile | Asp | Glu | Ile | Ile | Thr | His | Leu | Lys |
|---|---|---|---|---|---|---|---|---|---|---|---|---|---|---|
| Gln | Pro | Pro | Leu | Pro | Leu | Leu | Asp | Phe | Asn | Asn | Leu | Asn | Gly | Glu |
| Asp | Gln | Asp | Ile | Leu | Met | Glu | Asn | Asn | Leu | Arg | Arg | Pro | Asn | Leu |
| Glu | Ala | Phe | Asn | Arg | Ala | Val | Lys | Ser | Leu | Gln | Asn | Ala | Ser | Ala |
| Ile | Glu | Ser | Ile | Leu | Lys | Asn | Leu | Leu | Pro | Cys | Leu | Pro | Leu | Ala |
| Thr | Ala | Ala | Pro | Thr | Arg | His | Pro | Ile | His | Ile | Lys | Ala | Gly | Asp |
| Trp | Asn | Glu | Phe | Arg | Arg | Lys | Leu | Thr | Phe | Tyr | Leu | Lys | Thr | Leu |
| Glu | Asn | Ala | Gln | Ala | Gln | Gln | [SEQ ID NO:19] | | | | | | | | pMON5960 (Met-15-125hIL-3) having an M11 substitution.
Protein sequence #4

| Met | Asn | Cys | Ser | Asn | Met | Ile | Asp | Glu | Ile | Ile | Thr | His | Leu | Lys |
|---|---|---|---|---|---|---|---|---|---|---|---|---|---|---|
| Gln | Pro | Pro | Leu | Pro | Leu | Leu | Asp | Phe | Asn | Asn | Leu | Asn | Gly | Glu |
| Asp | Gln | Asp | Ile | Leu | Met | Glu | Asn | Asn | Leu | Arg | Arg | Pro | Asn | Leu |
| Glu | Ala | Phe | Asn | Arg | Ala | Val | Lys | Ser | Leu | Gln | Asn | Ala | Ser | Ala |
| Ile | Glu | Ser | Ile | Leu | Lys | Asn | Leu | Leu | Pro | Cys | Leu | Pro | Leu | Ala |
| Thr | Ala | Ala | Ser | Ala | Leu | Pro | Pro | Ile | His | Ile | Lys | Asp | Gly | Asp |
| Trp | Asn | Glu | Phe | Arg | Arg | Lys | Leu | Thr | Phe | Tyr | Leu | Lys | Thr | Leu |
| Glu | Asn | Ala | Gln | Ala | Gln | Gln | [SEQ ID NO:65] | | | | | | | | pMON5961 (Met-15-125hIL-3) having an M12 substitution.
Protein sequence #5

| Met | Asn | Cys | Ser | Asn | Met | Ile | Asp | Glu | Ile | Ile | Thr | His | Leu | Lys |
|---|---|---|---|---|---|---|---|---|---|---|---|---|---|---|
| Gln | Pro | Pro | Leu | Pro | Leu | Leu | Asp | Phe | Asn | Asn | Leu | Asn | Gly | Glu |
| Asp | Gln | Asp | Ile | Leu | Met | Glu | Asn | Asn | Leu | Arg | Arg | Pro | Asn | Leu |
| Glu | Ala | Phe | Asn | Arg | Ala | Val | Lys | Ser | Leu | Gln | Asn | Ala | Ser | Ala |
| Ile | Glu | Ser | Ile | Leu | Lys | Asn | Leu | Leu | Pro | Cys | Leu | Pro | Leu | Ala |
| Thr | Ala | Ala | Pro | Thr | Arg | His | Gly | Val | Phe | Ile | Arg | Asp | Gly | Asp |
| Trp | Asn | Glu | Phe | Arg | Arg | Lys | Leu | Thr | Phe | Tyr | Leu | Lys | Thr | Leu |
| Glu | Asn | Ala | Gln | Ala | Gln | Gln | [SEQ ID NO:66] | | | | | | | | pMON5962 (Met-15-125hIL-3) having an M10 substitution.
Protein sequence #6

| Met | Asn | Cys | Ser | Asn | Met | Ile | Asp | Glu | Ile | Ile | Thr | His | Leu | Lys |
|---|---|---|---|---|---|---|---|---|---|---|---|---|---|---|
| Gln | Pro | Pro | Leu | Pro | Leu | Leu | Asp | Phe | Asn | Asn | Leu | Asn | Gly | Glu |
| Asp | Gln | Asp | Ile | Leu | Met | Glu | Asn | Asn | Leu | Arg | Arg | Pro | Asn | Leu |
| Glu | Ala | Phe | Asn | Arg | Ala | Val | Lys | Ser | Leu | Gln | Asn | Ala | Ser | Ala |
| Ile | Glu | Ser | Ile | Leu | Lys | Asn | Leu | Leu | Pro | Cys | Leu | Pro | Thr | Ser |
| Ala | Asn | Asp | Pro | Thr | Arg | His | Pro | Ile | His | Ile | Lys | Asp | Gly | Asp |
| Trp | Asn | Glu | Phe | Arg | Arg | Lys | Leu | Thr | Phe | Tyr | Leu | Lys | Thr | Leu |
| Glu | Asn | Ala | Gln | Ala | Gln | Gln | [SEQ ID NO:67] | | | | | | | | pMON5963 (Met-15-125hIL-3 Ala 101) having an M9 substitution.
Protein sequence #7

TABLE 3-continued

POLYPEPTIDES

| Met | Asn | Cys | Ser | Asn | Met | Ile | Asp | Glu | Ile | Ile | Thr | His | Leu | Lys |
|---|---|---|---|---|---|---|---|---|---|---|---|---|---|---|
| Gln | Pro | Pro | Leu | Pro | Leu | Leu | Asp | Phe | Asn | Asn | Leu | Asn | Gly | Glu |
| Asp | Gln | Asp | Ile | Leu | Met | Glu | Asn | Asn | Leu | Arg | Arg | Pro | Asn | Leu |
| Glu | Ala | Phe | Asn | Arg | Ala | Val | Lys | Ser | Leu | Gln | Asn | Ala | Ser | Ala |
| Ile | Lys | Ser | Asn | Leu | Gln | Lys | Leu | Asn | Ser | Cys | Leu | Pro | Leu | Ala |
| Thr | Ala | Ala | Pro | Thr | Arg | His | Pro | Ile | His | Ile | Lys | Leu | Gly | Asp |
| Trp | Asn | Glu | Phe | Arg | Arg | Lys | Leu | Thr | Phe | Tyr | Leu | Lys | Thr | Leu |
| Glu | Asn | Ala | Gln | Ala | Gln | Gln | [SEQ ID NO:68] | | | | | | | | pMON5968 (Met-15-125hIL-3) having an M13 substitution.
Protein sequence #8

| Met | Asn | Cys | Ser | Asn | Met | Ile | Asp | Glu | Ile | Ile | Thr | His | Leu | Lys |
|---|---|---|---|---|---|---|---|---|---|---|---|---|---|---|
| Gln | Pro | Pro | Leu | Pro | Leu | Leu | Asp | Phe | Asn | Asn | Leu | Asn | Gly | Glu |
| Asp | Gln | Asp | Ile | Leu | Met | Glu | Asn | Asn | Leu | Arg | Arg | Pro | Asn | Leu |
| Glu | Ala | Phe | Asn | Arg | Ala | Val | Lys | Ser | Leu | Gln | Asn | Ala | Ser | Ala |
| Ile | Glu | Ser | Ile | Leu | Lys | Asn | Leu | Leu | Pro | Cys | Leu | Pro | Leu | Ala |
| Thr | Ala | Ala | Pro | Thr | Arg | His | Pro | Ile | His | Ile | Lys | Asp | Leu | Asp |
| Glu | Phe | Arg | Arg | Lys | Leu | Thr | Phe | Tyr | Leu | Lys | Thr | Leu | Glu | Asn |
| Ala | Gln | Ala | Gln | Gln | [SEQ ID NO:69] | | | | | | | | | | pMON5969 (Met-15-125hIL-3)
Protein sequence #9

| Met | Asn | Cys | Ser | Asn | Met | Ile | Asp | Glu | Ile | Ile | Thr | His | Leu | Lys |
|---|---|---|---|---|---|---|---|---|---|---|---|---|---|---|
| Gln | Pro | Pro | Leu | Pro | Leu | Leu | Asp | Phe | Asn | Asn | Leu | Asn | Gly | Glu |
| Asp | Gln | Asp | Ile | Leu | Met | Glu | Asn | Asn | Leu | Arg | Arg | Pro | Asn | Leu |
| Glu | Ala | Phe | Asn | Arg | Ala | Val | Lys | Ser | Leu | Gln | Asn | Ala | Ser | Ala |
| Ile | Glu | Ser | Ile | Leu | Lys | Asn | Leu | Leu | Pro | Cys | Leu | Pro | Leu | Ala |
| Thr | Ala | Ala | Pro | Thr | Arg | His | Pro | Ile | His | Ile | Lys | Asp | Gly | Asp |
| Trp | Asn | Glu | Phe | Arg | Arg | Lys | Leu | Thr | Phe | Tyr | Leu | Lys | Thr | Leu |
| Glu | Asn | Ala | Gln | Ala | Gln | Gln | [SEQ ID NO:18] | | | | | | | | pMON5970 (Met-15-125hIL-3) having an M5 substitution.
Protein sequence #10

| Met | Asn | Cys | Ser | Asn | Met | Ile | Asp | Glu | Ile | Ile | Thr | His | Leu | Lys |
|---|---|---|---|---|---|---|---|---|---|---|---|---|---|---|
| Gln | Pro | Pro | Leu | Pro | Leu | Leu | Asp | Phe | Asn | Asn | Leu | Asn | Gly | Glu |
| Asp | Gln | Asp | Ser | Leu | Arg | Asn | Lys | Ser | Leu | Arg | Arg | Pro | Asn | Leu |
| Glu | Ala | Phe | Asn | Arg | Ala | Val | Lys | Ser | Leu | Gln | Asn | Ala | Ser | Ala |
| Ile | Glu | Ser | Ile | Leu | Lys | Asn | Leu | Leu | Pro | Cys | Leu | Pro | Leu | Ala |
| Thr | Ala | Ala | Pro | Thr | Arg | His | Pro | Ile | His | Ile | Lys | Asp | Gly | Asp |
| Trp | Asn | Glu | Phe | Arg | Arg | Lys | Leu | Thr | Phe | Tyr | Leu | Lys | Thr | Leu |
| Glu | Asn | Ala | Gln | Ala | Gln | Gln | [SEQ ID NO:70] | | | | | | | | pMON5972 (Met-15-125hIL-3) having an M6 substitution.
Protein sequence #11

| Met | Asn | Cys | Ser | Asn | Met | Ile | Asp | Glu | Ile | Ile | Thr | His | Leu | Lys |
|---|---|---|---|---|---|---|---|---|---|---|---|---|---|---|
| Gln | Pro | Pro | Leu | Pro | Leu | Leu | Asp | Phe | Asn | Asn | Leu | Asn | Gly | Glu |
| Asp | Gln | Asp | Ile | Leu | Met | Glu | Asn | Asn | Phe | Arg | Arg | Val | Asn | Leu |
| Ser | Lys | Phe | Val | Glu | Ala | Val | Lys | Ser | Leu | Gln | Asn | Ala | Ser | Ala |
| Ile | Glu | Ser | Ile | Leu | Lys | Asn | Leu | Leu | Pro | Cys | Leu | Pro | Leu | Ala |
| Thr | Ala | Ala | Pro | Thr | Arg | His | Pro | Ile | His | Ile | Lys | Asp | Gly | Asp |
| Trp | Asn | Glu | Phe | Arg | Arg | Lys | Leu | Thr | Phe | Tyr | Leu | Lys | Thr | Leu |
| Glu | Asn | Ala | Gln | Ala | Gln | Gln | [SEQ ID NO:71] | | | | | | | | pMON5973 (Met-15-125hIL-3) having an M7 substitution.
Protein sequence #12

| Met | Asn | Cys | Ser | Asn | Met | Ile | Asp | Glu | Ile | Ile | Thr | His | Leu | Lys |
|---|---|---|---|---|---|---|---|---|---|---|---|---|---|---|
| Gln | Pro | Pro | Leu | Pro | Leu | Leu | Asp | Phe | Asn | Asn | Leu | Asn | Gly | Glu |
| Asp | Gln | Asp | Ile | Leu | Met | Glu | Asn | Asn | Leu | Arg | Arg | Pro | Asn | Leu |
| Glu | Ala | Phe | Asn | Arg | Ser | Gln | Gly | Glu | Val | Asp | Asn | Ala | Ser | Ala |
| Ile | Glu | Ser | Ile | Leu | Lys | Asn | Leu | Leu | Pro | Cys | Leu | Pro | Leu | Ala |
| Thr | Ala | Ala | Pro | Thr | Arg | His | Pro | Ile | His | Ile | Lys | Asp | Gly | Asp |
| Trp | Asn | Glu | Phe | Arg | Arg | Lys | Leu | Thr | Phe | Tyr | Leu | Lys | Thr | Leu |
| Glu | Asn | Ala | Gln | Ala | Gln | Gln | [SEQ ID NO:72] | | | | | | | | pMON5974 (Not-15-125hIL-3 del aa29-35) having the M2
deletion shown in FIG. 19.
Protein sequence #13

| Met | Asn | Cys | Ser | Asn | Met | Ile | Asp | Glu | Ile | Ile | Thr | His | Leu | Lys |
|---|---|---|---|---|---|---|---|---|---|---|---|---|---|---|
| Asp | Phe | Asn | Asn | Leu | Asn | Gly | Glu | Asp | Gln | Asp | Ile | Leu | Met | Glu |
| Asn | Asn | Leu | Arg | Arg | Pro | Asn | Leu | Glu | Ala | Phe | Asn | Arg | Ala | Val |
| Lys | Ser | Leu | Gln | Asn | Ala | Ser | Ala | Ile | Glu | Ser | Ile | Leu | Lys | Asn |

TABLE 3-continued

POLYPEPTIDES

| Leu | Leu | Pro | Cys | Leu | Pro | Leu | Ala | Thr | Ala | Ala | Pro | Thr | Arg | His |
|---|---|---|---|---|---|---|---|---|---|---|---|---|---|---|
| Pro | Ile | His | Ile | Lys | Asp | Gly | Asp | Trp | Asn | Glu | Phe | Arg | Arg | Lys |
| Leu | Thr | Phe | Tyr | Leu | Lys | Thr | Leu | Glu | Asn | Ala | Gln | Ala | Gln | Gln |

[SEQ ID NO:73]

pMON5975 (Met-15-125hIL-3) having an M4 substitution.
Protein sequence #14

| Met | Asn | Cys | Ser | Asn | Met | Ile | Asp | Glu | Ile | Ile | Thr | His | Leu | Lys |
|---|---|---|---|---|---|---|---|---|---|---|---|---|---|---|
| Gln | Pro | Pro | Leu | Pro | Leu | Leu | Asp | Phe | Asn | Asn | Leu | Thr | Asp | Asp |
| Glu | Gly | Pro | Ile | Leu | Met | Glu | Asn | Asn | Leu | Arg | Arg | Pro | Asn | Leu |
| Glu | Ala | Phe | Asn | Arg | Ala | Val | Lys | Ser | Leu | Gln | Asn | Ala | Ser | Ala |
| Ile | Glu | Ser | Ile | Leu | Lys | Asn | Leu | Leu | Pro | Cys | Leu | Pro | Leu | Ala |
| Thr | Ala | Ala | Pro | Thr | Arg | His | Pro | Ile | His | Ile | Lys | Asp | Gly | Asp |
| Trp | Asn | Glu | Phe | Arg | Arg | Lys | Leu | Thr | Phe | Tyr | Leu | Lys | Thr | Leu |
| Glu | Asn | Ala | Gln | Ala | Gln | Gln | [SEQ ID NO:74] | | | | | | | | pMON5977 (Met-15-125hIL-3) having an M3 substitution.
Protein sequence #15

| Met | Asn | Cys | Ser | Asn | Met | Ile | Asp | Glu | Ile | Ile | Thr | His | Leu | Lys |
|---|---|---|---|---|---|---|---|---|---|---|---|---|---|---|
| Gln | Pro | Pro | Leu | Pro | Leu | Leu | Glu | Pro | Glu | Leu | Lys | Asn | Gly | Glu |
| Asp | Gln | Asp | Ile | Leu | Met | Glu | Asn | Asn | Leu | Arg | Arg | Pro | Asn | Leu |
| Glu | Ala | Phe | Asn | Arg | Ala | Val | Lys | Ser | Leu | Gln | Asn | Ala | Ser | Ala |
| Ile | Glu | Ser | Ile | Leu | Lys | Asn | Leu | Leu | Pro | Cys | Leu | Pro | Leu | Ala |
| Thr | Ala | Ala | Pro | Thr | Arg | His | Pro | Ile | His | Ile | Lys | Asp | Gly | Asp |
| Trp | Asn | Glu | Phe | Arg | Arg | Lys | Leu | Thr | Phe | Tyr | Leu | Lys | Thr | Leu |
| Glu | Asn | Ala | Gln | Ala | Gln | Gln | [SEQ ID NO:75] | | | | | | | | pMON5978 (Met-Ala-15-125hIL-3)
Protein sequence #16

| Met | Ala | Asn | Cys | Ser | Asn | Met | Ile | Asp | Glu | Ile | Ile | Thr | His | Leu |
|---|---|---|---|---|---|---|---|---|---|---|---|---|---|---|
| Lys | Gln | Pro | Pro | Leu | Pro | Leu | Leu | Asp | Phe | Asn | Asn | Leu | Asn | Gly |
| Glu | Asp | Gln | Asp | Ile | Leu | Met | Glu | Asn | Asn | Leu | Arg | Arg | Pro | Asn |
| Leu | Glu | Ala | Phe | Asn | Arg | Ala | Val | Lys | Ser | Leu | Gln | Asn | Ala | Ser |
| Ala | Ile | Glu | Ser | Ile | Leu | Lys | Asn | Leu | Leu | Pro | Cys | Leu | Pro | Leu |
| Ala | Thr | Ala | Ala | Pro | Thr | Arg | His | Pro | Ile | His | Ile | Lys | Asp | Gly |
| Asp | Trp | Asn | Glu | Phe | Arg | Arg | Lys | Leu | Thr | Phe | Tyr | Leu | Lys | Thr |
| Leu | Glu | Asn | Ala | Gln | Ala | Gln | Gln | [SEQ ID NO:20] | | | | | | | pMON5980 (Met-Ala-15-125hIL-3) having an M1
substitution.
Protein sequence #17

| Met | Ala | Asn | Cys | Ser | Ser | Ile | Val | Lys | Glu | Ile | Ile | Gly | Lys | Leu |
|---|---|---|---|---|---|---|---|---|---|---|---|---|---|---|
| Pro | Gln | Pro | Pro | Leu | Pro | Leu | Leu | Asp | Phe | Asn | Asn | Leu | Asn | Gly |
| Glu | Asp | Gln | Asp | Ile | Leu | Met | Glu | Asn | Asn | Leu | Arg | Arg | Pro | Asn |
| Leu | Glu | Ala | Phe | Asn | Arg | Ala | Val | Lys | Ser | Leu | Gln | Asn | Ala | Ser |
| Ala | Ile | Glu | Ser | Ile | Leu | Lys | Asn | Leu | Leu | Pro | Cys | Leu | Pro | Leu |
| Ala | Thr | Ala | Ala | Pro | Thr | Arg | His | Pro | Ile | His | Ile | Lys | Asp | Gly |
| Asp | Trp | Asn | Glu | Phe | Arg | Arg | Lys | Leu | Thr | Phe | Tyr | Leu | Lys | Thr |
| Leu | Glu | Asn | Ala | Gln | Ala | Gln | Gln | [SEQ ID NO:76] | | | | | | |

TABLE 4

DNA SEQUENCES pMON5976 (Met-15-125hIL-3 ALA 101)
DNA sequence #1
ATGAACTGCTCTAACATGATCGATGAAATCATCACCCACCTGAAGCAGCCACCGCTGCCG
CTGCTGGACTTCAACAACCTCAATGGTGAAGACCAAGATATCCTGATGGAAAATAACCTT
CGTCGTCCAAACCTCGAGGCATTCAACCGTGCTGTCAAGTCTCTGCAGAATGCATCAGCA
ATTGAGAGCATTCTTAAAAATCTCCTGCCATGTCTGCCGCTAGCCACGGCCGCACCCACG
CGACATCCAATCCATATCAAGGCTGGTGACTGGAATGAATTCCGTCGTAAACTGACCTTC
TATCTGAAAACCTTGGAGAACGCGCAGGCTCAACAG [SEQ ID NO:77]
pMON5979 (Met-15-125hIL-3 ALA 101) having an M8
substitution.
DNA sequence #2
ATGAACTGCTCTAACATGATCGATGAAATCATCACCCACCTGAAGCAGCCACCGCTGCCG
CTGCTGGACTTCAACAACCTCAATGGTGAAGACCAAGATATCCTGATGGAAAATAACCTT
CGTCGTCCAAACCTCGAGGCATTCAACCGTGCTGTCAAGTCTCTGCAGCCGGAAGACCGT
TACGTTATCGAATCCATCCTGAAAAACCTGTGCCGTGCCTGCCGCTAGCCACGGCCGCA
CCCACGCGACATCCAATCCATATCAAGGCTGGTGACTGGAATGAATTCCGTCGTAAACTG
ACCTTCTATCTGAAAACCTTGGAGAACGCGCAGGCTCAACAG [SEQ ID NO:78]

TABLE 4-continued

DNA SEQUENCES pMON5941 (Met 15-125hIL-3 Ala 101)
DNA sequence #3
ATGAACTGCTCTAACATGATCGATGAAATTATAACACACTTAAAGCAGCCACCTTTGCCT
TTGCTGGACTTCAACAACCTCAATGGGGAAGACCAAGACATTCTGATGGAAAATAACCTT
CGAAGGCCAAACCTGGAGGCATTCAACAGGGCTGTCAAGAGTTTACAGAATGCATCAGCA
ATTGAGAGCATTCTTAAAAATCTCCTGCCATGTCTGCCGCTAGCCACGGCCGCACCCACG
CGACATCCAATCCATATCAAGGCTGGTGACTGGAATGAATTCCGTCGTAAACTGACCTTC
TATCTGAAAACCTTGGAGAACGCGCAGGCTCAACAG [SEQ ID NO:79]
pMON5960 (Met-15-125hIL-3) having an M11
substitution.
DNA sequence #4
ATGAACTGCTCTAACATGATCGATGAAATTATAACACACTTAAAGCAGCCACCTTTGCCT
TTGCTGGACTTCAACAACCTCAATGGGGAAGACCAAGACATTCTGATGGAAAATAACCTT
CGAAGGCCAAACCTGGAGGCATTCAACAGGGCTGTCAAGAGTTTACAGAATGCATCAGCA
ATTGAGAGCATTCTTAAAAATCTCCTGCCATGTCTGCCGCTAGCCACGGCCGCATCCGCT
CTGCCGCCAATCCATATCAAGGACGGTGACTGGAATGAATTCCGTCGTAAACTGACCTTC
TATCTGAAAACCTTGGAGAACGCGCAGGCTCAACAG [SEQ ID NO:80]
pMON5961 (Met-15-125hIL-3) having an M12
substitution.
DNA SEQUENCE #5
ATGAACTGCTCTAACATGATCGATGAAATTATAACACACTTAAAGCAGCCACCTTTGCCT
TTGCTGGACTTCAACAACCTCAATGGGGAAGACCAAGACATTCTGATGGAAAATAACCTT
CGAAGGCCAAACCTGGAGGCATTCAACAGGGCTGTCAAGAGTTTACAGAATGCATCAGCA
ATTGAGAGCATTCTTAAAAATCTCCTGCCATGTCTGCCGCTAGCCACGGCCGCACCGACG
CGTCATGGTGTTTTCATCCGTGACGGTGACTGGAATGAATTCCGTCGTAAACTGACCTTC
TATCTGAAAACCTTGGAGAACGCGCAGGCTCAACAG [SEQ ID NO:81]
pHON5962 (Met-15-125hIL-3) having an M10
substitution.
DNA SEQUENCE #6
ATGAACTGCTCTAACATGATCGATGAAATTATAACACACTTAAAGCAGCCACCTTTGCCT
TTGCTGGACTTCAACAACCTCAATGGGGAAGACCAAGACATTCTGATGGAAAATAACCTT
CGAAGGCCAAACCTGGAGGCATTCAACAGGGCTGTCAAGAGTTTACAGAATGCATCAGCA
ATTGAGAGCATTCTTAAAAATCTCCTGCCATGTCTGCCGACCTCCGCTAACGATCCGACG
CGTCATCCAATCCATATCAAGGACGGTGACTGGAACGAATTCCGTCGTAAACTGACCTTC
TATCTGAAAACCTTGGAGAACGCGCAGGCTCAACAG [SEQ ID NO:82]
pMON5963 (Met-15-125hIL-3 Ala 101) having an M9
substitution.
DNA sequence #7
ATGAACTGCTCTAACATGATCGATGAAATTATAACACACTTAAAGCAGCCACCTTTGCCT
TTGCTGGACTTCAACAACCTCAATGGGGAAGACCAAGACATTCTGATGGAAAATAACCTT
CGAAGGCCAAACCTGGAGGCATTCAACAGGGCTGTCAAGAGTTTACAGAATGCATCAGCA
ATTAAAAGCAACCTGCAGAAGCTCAACTCCTGTCTGCCGCTAGCCACGGCCGCACCCACG
CGACATCCAATCCATATCAAGGCTGGTGACTGGAATGAATTCCGTCGTAAACTGACCTTC
TATCTGAAAACCTTGGAGAACGCGCAGGCTCAACAG [SEQ ID NO:83]
pMON5968 (Met-15-125hIL-3) having an M13
substitution.
DNA sequence #8
ATGAACTGCTCTAACATGATCGATGAAATTATAACACACTTAAAGCAGCCACCTTTGCCT
TTGCTGGACTTCAACAACCTCAATGGGGAAGACCAAGACATTCTGATGGAAAATAACCTT
CGAAGGCCAAACCTGGAGGCATTCAACAGGGCTGTCAAGAGTTTACAGAATGCATCAGCA
ATTGAGAGCATTCTTAAAAATCTCCTGCCATGTCTGCCGCTAGCCACGGCCGCACCGACG
CGTCATCCAATCCATATCAAGGACCTGGACGAATTCCGTCGTAAACTGACCTTCTATCTG
AAAACCTTGGAGAACGCGCAGGCTCAACAG [SEQ ID NO:84]
pMON5969 (Met 15-125hIL-3)
DNA sequence #9
ATGAACTGCTCTAACATGATCGATGAAATCATCACCCACCTGAAGCAGCCACCGCTGCCG
CTGCTGGACTTCAACAACCTCAATGGTGAAGACCAAGATATCCTGATGGAAAATAACCTT
CGTCGTCCAAACCTCGAGGCATTCAACCGTGCTGTCAAGTCTCTGCAGAATGCATCAGCA
ATTGAGAGCATTCTTAAAAATCTCCTGCCATGTCTGCCCCTGGCCACGGCCGCACCCACG
CGACATCCAATCCATATCAAGGACGGTGACTGGAATGAATTCCGTCGTAAACTGACCTTC
TATCTGAAAACCTTGGAGAACGCGCAGGCTCAACAG [SEQ ID NO:85]
pMON5970 (Met-15-125hIL-3) having an M6
substitution.
DNA sequence #10
ATGAACTGCTCTAACATGATCGATGAAATCATCACCCACCTGAAGCAGCCACCGCTGCCG
CTGCTGGACTTCAACAACCTCAATGGTGAAGACCAAGATTCCTGCGTAACAAATCCCTT
CGTCGTCCAAACCTCGAGGCATTCAACCGTGCTGTCAAGTCTCTGCAGAATGCATCAGCA
ATTGAGAGCATTCTTAAAAATCTCCTGCCATGTCTGCCCCTGGCCACGGCCGCACCCACG
CGACATCCAATCCATATCAAGGACGGTGACTGGAATGAATTCCGTCGTAAACTGACCTTC
TATCTGAAAACCTTGGAGAACGCGCAGGCTCAACAG [SEQ ID NO:86]
pMON5972 (Met-15-125hIL-3) having an M6
substitution.
DNA sequence #11
ATGAACTGCTCTAACATGATCGATGAAATCATCACCCACCTGAAGCAGCCACCGCTGCCG
CTGCTGGACTTCAACAACCTCAATGGTGAAGACCAAGATATCCTGATGGAAAATAACTTC
CGTCGTGTTAACCTCTCCAAATTCGTTGAAGCTGTCAAGTCTCTGCAGAATGCATCAGCA
ATTGAGAGCATTCTTAAAAATCTCCTGCCATGTCTGCCCCTGGCCACGGCCGCACCCACG

TABLE 4-continued

DNA SEQUENCES

CGACATCCAATCCATATCAAGGACGGTGACTGGAATGAATTCCGTCGTAAACTGACCTTC
TATCTGAAAACCTTGGAGAACGCGCAGGCTCAACAG [SEQ ID NO:87]
pMON5973 (Met-15-125hIL-3) having an M7
substitution.
DNA sequence #12
ATGAACTGCTCTAACATGATCGATGAAATCATCACCCACCTGAAGCAGCCACCGCTGCCG
CTGCTGGACTTCAACAACCTCAATGGTGAAGACCAAGATATCCTGATGGAAAATAACCTT
CGTCGTCCAAACCTCGAGGCATTCAACCGTTCCCAGGGTGAAGTTGACAATGCATCAGCA
ATTGAGAGCATTCTTAAAAATCTCCTGCCATGTCTGCCCCTGGCCACGGCCGCACCCACG
CGACATCCAATCCATATCAAGGACGGTGACTGGAATGAATTCCGTCGTAAACTGACCTTC
TATCTGAAAACCTTGGAGAACGCGCAGGCTCAACAG [SEQ ID NO:88]
pMON5974 (Met-15-125hIL-3 del aa29-35) having the
M2 deletion shown in FIG. 19.
DNA sequence #13
ATGAACTGCTCTAACATGATCGATGAAATCATCACCCACCTGAAGGACTTCAACAACCTC
AATGGTGAAGACCAAGATATCCTGATGGAAAATAACCTTCGTCGTCCAAACCTCGAGGCA
TTCAACCGTGCTGTCAAGTCTCTGCAGAATGCATCAGCAATTGAGAGCATTCTTAAAAAT
CTCCTGCCATGTCTGCCCCTGGCCACGGCCGCACCCACGCGACATCCAATCCATATCAAG
GACGGTGACTGGAATGAATTCCGTCGTAAACTGACCTTCTATCTGAAAACCTTGGAGAAC
GCGCAGGCTCAACAG [SEQ ID NO:89]
pMON5975 (Met-15-125hIL-3) having an M4
substitution.
DNA sequence #14
ATGAACTGCTCTAACATGATCGATGAAATCATCACCCACCTGAAGCAGCCACCGCTGCCG
CTGCTGGACTTCAACAACCTCACCGACGACGAAGGTCCGATCCTGATGGAAAATAACCTT
CGTCGTCCAAACCTCGAGGCATTCAACCGTGCTGTCAAGTCTCTGCAGAATGCATCAGCA
ATTGAGAGCATTCTTAAAAATCTCCTGCCATGTCTGCCCCTGGCCACGGCCGCACCCACG
CGACATCCAATCCATATCAAGGACGGTGACTGGAATGAATTCCGTCGTAAACTGACCTTC
TATCTGAAAACCTTGGAGAACGCGCAGGCTCAACAG [SEQ ID NO:90]
pMON5977 (Met-15-125hIL-3) having an M3
substitution.
DNA sequence #15
ATGAACTGCTCTAACATGATCGATGAAATCATCACCCACCTGAAGCAGCCACCGCTGCCG
CTGCTGGAACCGGAACTGAAAAATGGTGAAGACCAAGATATCCTGATGGAAAATAACCTT
CGTCGTCCAAACCTCGAGGCATTCAACCGTGCTGTCAAGTCTCTGCAGAATGCATCAGCA
ATTGAGAGCATTCTTAAAAATCTCCTGCCATGTCTGCCCCTGGCCACGGCCGCACCCACG
CGACATCCAATCCATATCAAGGACGGTGACTGGAATGAATTCCGTCGTAAACTGACCTTC
TATCTGAAAACCTTGGAGAACGCGCAGGCTCAACAG [SEQ ID NO:91]
pNON5978 (Met-Ala-15-125hIL-3)
DNA sequence #16
ATGGCTAACTGCTCTAACATGATCGATGAAATCATCACCCACCTGAAGCAGCCACCGCTG
CCGCTGCTGGACTTCAACAACCTCAATGGTGAAGACCAAGATATCCTGATGGAAAATAAC
CTTCGTCGTCCAAACCTCGAGGCATTCAACCGTGCTGTCAAGTCTCTGCAGAATGCATCA
GCAATTGAGAGCATTCTTAAAAATCTCCTGCCATGTCTGCCCCTGGCCACGGCCGCACCC
ACGCGACATCCAATCCATATCAAGGACGGTGACTGGAATGAATTCCGTCGTAAACTGACC
TTCTATCTGAAAACCTTGGAGAACGCGCAGGCTCAACAG [SEQ ID NO:92]
pMON5980 (Met-Ala-15-125hIL-3) having an M1
substitution.
DNA sequence #17
ATGGCTAACTGCTCTTCCATCGTTAAAGAAATCATCGGTAAACTGCCGCAGCCACCGCTG
CCGCTGCTGGACTTCAACAACCTCAATGGTGAAGACCAAGATATCCTGATGGAAAATAAC
CTTCGTCGTCCAAACCTCGAGGCATTCAACCGTGCTGTCAAGTCTCTGCAGAATGCATCA
GCAATTGAGAGCATTCTTAAAAATCTCCTGCCATGTCTGCCCCTGGCCACGGCCGCACCC
ACGCGACATCCAATCCATATCAAGGACGGTGACTGGAATGAATTCCGTCGTAAACTGACC
TTCTATCTGAAAACCTTGGAGAACGCGCAGGCTCAACAG [SEQ ID NO:93]

Table 5 shows the DNA sequences which code for the hIL-3 mutant polypeptide encoded by the plasmid indicated. The numbers correspond to the number of the amino acid coded for in the sequence of native hIL-3 except that the codon for the Met initiator always appears as the first codon in the sequence. The ATG which appears at the beginning of each sequence is the codon for methionine (Met) which always is encoded at the N-terminus in *E. coli* expression systems. In the sequence for pMON5978 and pMON5967 the Met codon (ATG) and the Ala codon (GCT) precede the first native hIL-3 amino acid codon. When this initial Met is followed by Ala, most of the Met is cleaved upon expression of the polypeptide.

TABLE 5

Example 5(a); pMON5872; (15-133)hIL-3:

|     |     | 15  |     |     |     |     | 20  |     |     |     | 25  |
| --- | --- | --- | --- | --- | --- | --- | --- | --- | --- | --- | --- |
|     | ATG | AAC | TGC | TCT | AAC | ATG | ATC | GAT | GAA | ATT | ATA | ACA |
|     |     |     |     | 30  |     |     |     |     | 35  |     |     |     |
| CAC | TTA | AAG | CAG | CCA | CCT | TTG | CCT | TTG | CTG | GAC | TTC | AAC |
|     | 40  |     |     |     |     | 45  |     |     |     |     | 50  |     |

TABLE 5-continued

| | | | | | | | | | | | |
|---|---|---|---|---|---|---|---|---|---|---|---|
| AAC | CTC | AAT | GGG | GAA | GAC | CAA | GAC | ATT | CTG | ATG | GAA | AAT |
| | | | 55 | | | | | 60 | | | |
| AAC | CTT | CGA | AGG | CCA | AAC | CTG | GAG | GCA | TTC | AAC | AGG | GCT |
| 65 | | | | | 70 | | | | | 75 | | |
| GTC | AAG | AGT | TTA | CAG | AAT | GCA | TCA | GCA | ATT | GAG | AGC | ATT |
| | | | 80 | | | | 85 | | | | | 90 |
| CTT | AAA | AAT | CTC | CTG | CCA | TGT | CTG | CCC | CTG | GCC | ACG | GCC |
| | | | | 95 | | | | | 100 | | | |
| GCA | CCC | ACG | CGA | CAT | CCA | ATC | CAT | ATC | AAG | GAC | GGT | GAC |
| | 105 | | | | | 110 | | | | | 115 | |
| TGG | AAT | GAA | TTC | CGT | CGT | AAA | CTG | ACC | TTC | TAT | CTG | AAA |
| | | | 120 | | | | | 125 | | | | |
| ACC | TTG | GAG | AAC | GCG | CAG | GCT | CAA | CAG | ACC | ACT | CTG | TCG |
| 130 | | | | | | | | | | | | |
| CTA | GCG | ATC | TTT | [SEQ ID NO:94] | | | | | | | | |

Example 6; pMON5887; Met-(1-125)hIL-3:

| | 1 | | | | 5 | | | | | 10 | | |
|---|---|---|---|---|---|---|---|---|---|---|---|---|
| ATG | GCT | CCA | ATG | ACT | CAG | ACT | ACT | TCT | CTT | AAG | ACT | TCT |
| | | | 15 | | | | 20 | | | | | 25 |
| TGG | GTT | AAC | TGC | TCT | AAC | ATG | ATC | GAT | GAA | ATT | ATA | ACA |
| | | | | 30 | | | | 35 | | | | |
| CAC | TTA | AAG | CAG | CCA | CCT | TTG | CCT | TTG | CTG | GAC | TTC | AAC |
| | 40 | | | | 45 | | | | | 50 | | |
| AAC | CTC | AAT | GGG | GAA | GAC | CAA | GAC | ATT | CTG | ATG | GAA | AAT |
| | | | 55 | | | | | 60 | | | | |
| AAC | CTT | CGA | AGG | CCA | AAC | CTG | GAG | GCA | TTC | AAC | AGG | GCT |
| 65 | | | | | 70 | | | | | 75 | | |
| GTC | AAG | AGT | TTA | CAG | AAT | GCA | TCA | GCA | ATT | GAG | AGC | ATT |
| | | | 80 | | | | 85 | | | | | 90 |
| CTT | AAA | AAT | CTC | CTG | CCA | TGT | CTG | CCC | CTG | GCC | ACG | GCC |
| | | | | 95 | | | | | 100 | | | |
| GCA | CCC | ACG | CGA | CAT | CCA | ATC | CAT | ATC | AAG | GAC | GGT | GAC |
| | 105 | | | | | 110 | | | | | 115 | |
| TGG | AAT | GAA | TTC | CGT | CGT | AAA | CTG | ACC | TTC | TAT | CTG | AAA |
| | | | 120 | | | | | 125 | | | | |
| ACC | TTG | GAG | AAC | GCG | CAG | GCT | CAA | CAG | [SEQ ID NO:95] | | | |

Example 7; pMON5901; Met-(15-125)hIL-3:

| | | 15 | | | | 20 | | | | | 25 | |
|---|---|---|---|---|---|---|---|---|---|---|---|---|
| | ATG | AAC | TGC | TCT | AAC | ATG | ATC | GAT | GAA | ATT | ATA | ACA |
| | | | | 30 | | | | 35 | | | | |
| CAC | TTA | AAG | CAG | CCA | CCT | TTG | CCT | TTG | CTG | GAC | TTC | AAC |
| | 40 | | | | 45 | | | | | 50 | | |
| AAC | CTC | AAT | GGG | GAA | GAC | CAA | GAC | ATT | CTG | ATG | GAA | AAT |
| | | | 55 | | | | | 60 | | | | |
| AAC | CTT | CGA | AGG | CCA | AAC | CTG | GAG | GCA | TTC | AAC | AGG | GCT |
| 65 | | | | | 70 | | | | | 75 | | |
| GTC | AAG | AGT | TTA | CAG | AAT | GCA | TCA | GCA | ATT | GAG | AGC | ATT |
| | | | 80 | | | | 85 | | | | | 90 |
| CTT | AAA | AAT | CTC | CTG | CCA | TGT | CTG | CCC | CTG | GCC | ACG | GCC |
| | | | | 95 | | | | | 100 | | | |
| GCA | CCC | ACG | CGA | CAT | CCA | ATC | CAT | ATC | AAG | GAC | GGT | GAC |
| | 105 | | | | | 110 | | | | | 115 | |
| TGG | AAT | GAA | TTC | CGT | CGT | AAA | CTG | ACC | TTC | TAT | CTG | AAA |
| | | | 120 | | | | | 125 | | | | |
| ACC | TTG | GAG | AAC | GCG | CAG | GCT | CAA | CAG | [SEQ ID NO:96] | | | |

Example 8; pMON5959; Met-(15-125)hIL-3:

| | | 15 | | | | 20 | | | | | 25 | |
|---|---|---|---|---|---|---|---|---|---|---|---|---|
| | ATG | AAC | TGC | TCT | AAC | ATG | ATC | GAT | GAA | ATC | ATC | ACC |
| | | | | 30 | | | | 35 | | | | |
| CAC | CTG | AAG | CAG | CCA | CCG | CTG | CCG | CTG | CTG | GAC | TTC | AAC |
| | 40 | | | | 45 | | | | | 50 | | |
| AAC | CTC | AAT | GGT | GAA | GAC | CAA | GAT | ATC | CTG | ATG | GAA | AAT |
| | | | 55 | | | | | 60 | | | | |
| AAC | CTT | CGT | CGT | CCA | AAC | CTC | GAG | GCA | TTC | AAC | CGT | GCT |
| 65 | | | | | 70 | | | | | 75 | | |
| GTC | AAG | TCT | CTG | CAG | AAT | GCA | TCA | GCA | ATT | GAG | AGC | ATT |
| | | | 80 | | | | 85 | | | | | 90 |
| CTT | AAA | AAT | CTC | CTG | CCA | TGT | CTG | CCC | CTG | GCC | ACG | GCC |
| | | | | 95 | | | | | 100 | | | |
| GCA | CCC | ACG | CGA | CAT | CCA | ATC | CAT | ATC | AAG | GAC | GGT | GAC |
| | 105 | | | | | 110 | | | | | 115 | |
| TGG | AAT | GAA | TTC | CGT | CGT | AAA | CTG | ACC | TTC | TAT | CTG | AAA |
| | | | 120 | | | | | 125 | | | | |
| ACC | TTG | GAG | AAC | GCG | CAG | GCT | CAA | CAG | [SEQ ID NO: 97] | | | |

TABLE 5-continued

Example 12; pMON5917; Met-(15-88)hIL-3:

|  | | 15 | | | | 20 | | | | 25 | |
|---|---|---|---|---|---|---|---|---|---|---|---|
|  | ATG | AAC | TGC | TCT | AAC | ATG | ATC | GAT | GAA | ATT | ATA | ACA |
|  |  |  |  | 30 |  |  |  |  | 35 |  |  |  |
| CAC | TTA | AAG | CAG | CCA | CCT | TTG | CCT | TTG | CTG | GAC | TTC | AAC |
|  | 40 |  |  |  |  | 45 |  |  |  |  | 50 |  |
| AAC | CTC | AAT | GGG | GAA | GAC | CAA | GAC | ATT | CTG | ATG | GAA | AAT |
|  |  |  | 55 |  |  |  |  | 60 |  |  |  |  |
| AAC | CTT | CGA | AGG | CCA | AAC | CTG | GAG | GCA | TTC | AAC | AGG | GCT |
| 65 |  |  |  |  | 70 |  |  |  |  | 75 |  |  |
| GTC | AAG | AGT | TTA | CAG | AAT | GCA | TCA | GCA | ATT | GAG | AGC | ATT |
|  |  | 80 |  |  |  |  | 85 |  |  |  |  |  |
| CTT | AAA | AAT | CTC | CTG | CCA | TGT | CTG | CCG | CTA | GCC | [SEQ ID NO:98] | |

Example 4(a); pMON5853; Met-(15-133)hIL-3 (Arg129):

|  | | 15 | | | | 20 | | | | 25 | |
|---|---|---|---|---|---|---|---|---|---|---|---|
|  | ATG | AAC | TGC | TCT | AAC | ATG | ATC | GAT | GAA | ATT | ATA | ACA |
|  |  |  |  | 30 |  |  |  |  | 35 |  |  |  |
| CAC | TTA | AAG | CAG | CCA | CCT | TTG | CCT | TTG | CTG | GAC | TTC | AAC |
|  | 40 |  |  |  |  | 45 |  |  |  |  | 50 |  |
| AAC | CTC | AAT | GGG | GAA | GAC | CAA | GAC | ATT | CTG | ATG | GAA | AAT |
|  |  |  | 55 |  |  |  |  | 60 |  |  |  |  |
| AAC | CTT | CGA | AGG | CCA | AAC | CTG | GAG | GCA | TTC | AAC | AGG | GCT |
| 65 |  |  |  |  | 70 |  |  |  |  | 75 |  |  |
| GTC | AAG | AGT | TTA | CAG | AAT | GCA | TCA | GCA | ATT | GAG | AGC | ATT |
|  |  | 80 |  |  |  |  | 85 |  |  |  |  | 90 |
| CTT | AAA | AAT | CTC | CTG | CCA | TGT | CTG | CCC | CTG | GCC | ACG | GCC |
|  |  |  |  | 95 |  |  |  |  | 100 |  |  |  |
| GCA | CCC | ACG | CGA | CAT | CCA | ATC | CAT | ATC | AAG | GAC | GGT | GAC |
|  | 105 |  |  |  |  | 110 |  |  |  |  | 115 |  |
| TGG | AAT | GAA | TTC | CGT | CGT | AAA | CTG | ACC | TTC | TAT | CTG | AAA |
|  |  |  | 120 |  |  |  |  | 125 |  |  |  |  |
| ACC | TTG | GAG | AAC | GCG | CAG | GCT | CAA | CAG | ACC | ACT | CTG | AGG |
| 130 |  |  |  |  |  |  |  |  |  |  |  |  |
| CTA | GCG | ATC | TTT | [SEQ ID NO:99] | | | | | | | | |

Example 9; pMON5976; [Met-(15-125)hIL-3 (Ala101)]

|  | | 15 | | | | 20 | | | | 25 | |
|---|---|---|---|---|---|---|---|---|---|---|---|
|  | ATG | AAC | TGC | TCT | AAC | ATG | ATC | GAT | GAA | ATC | ATC | ACC |
|  |  |  |  | 30 |  |  |  |  | 35 |  |  |  |
| CAC | CTG | AAG | CAG | CCA | CCG | CTG | CCG | CTG | CTG | GAC | TTC | AAC |
|  | 40 |  |  |  |  | 45 |  |  |  |  | 50 |  |
| AAC | CTC | AAT | GGT | GAA | GAC | CAA | GAT | ATC | CTG | ATG | GAA | AAT |
|  |  |  | 55 |  |  |  |  | 60 |  |  |  |  |
| AAC | CTT | CGT | CGT | CCA | AAC | CTC | GAG | GCA | TTC | AAC | CGT | GCT |
| 65 |  |  |  |  | 70 |  |  |  |  | 75 |  |  |
| GTC | AAG | TCT | CTG | CAG | AAT | GCA | TCA | GCA | ATT | GAG | AGC | ATT |
|  |  | 80 |  |  |  |  | 85 |  |  |  |  | 90 |
| CTT | AAA | AAT | CTC | CTG | CCA | TGT | CTG | CCG | CTA | GCC | ACG | GCC |
|  |  |  |  | 95 |  |  |  |  | 100 |  |  |  |
| GCA | CCC | ACG | CGA | CAT | CCA | ATC | CAT | ATC | AAG | GCT | GGT | GAC |
|  | 105 |  |  |  |  | 110 |  |  |  |  | 115 |  |
| TGG | AAT | GAA | TTC | CGT | CGT | AAA | CTG | ACC | TTC | TAT | CTG | AAA |
|  |  |  | 120 |  |  |  |  | 125 |  |  |  |  |
| ACC | TTG | GAG | AAC | GCG | CAG | GCT | CAA | CAG | [SEQ ID NO:100] | | | |

Example 13; pMON5941; [Met-(15-125)hIL-3(Ala101)]

|  | | 15 | | | | 20 | | | | 25 | |
|---|---|---|---|---|---|---|---|---|---|---|---|
|  | ATG | AAC | TGC | TCT | AAC | ATG | ATC | GAT | GAA | ATT | ATA | ACA |
|  |  |  |  | 30 |  |  |  |  | 35 |  |  |  |
| CAC | TTA | AAG | CAG | CCA | CCT | TTG | CCT | TTG | CTG | GAC | TTC | AAC |
|  | 40 |  |  |  |  | 45 |  |  |  |  | 50 |  |
| AAC | CTC | AAT | GGG | GAA | GAC | CAA | GAC | ATT | CTG | ATG | GAA | AAT |
|  |  |  | 55 |  |  |  |  | 60 |  |  |  |  |
| AAC | CTT | CGA | AGG | CCA· | AAC | CTG | GAG | GCA | TTC | AAC | AGG | GCT |
| 65 |  |  |  |  | 70 |  |  |  |  | 75 |  |  |
| GTC | AAG | AGT | TTA | CAG | AAT | GCA | TCA | GCA | ATT | GAG | AGC | ATT |
|  |  | 80 |  |  |  |  | 85 |  |  |  |  | 90 |
| CTT | AAA | AAT | CTC | CTG | CCA | TGT | CTG | CCG | CTA | GCC | ACG | GCC |
|  |  |  |  | 95 |  |  |  |  | 100 |  |  |  |
| GCA | CCC | ACG | CGA | CAT | CCA | ATC | CAT | ATC | AAG | GCT | GGT | GAC |
|  | 105 |  |  |  |  | 110 |  |  |  |  | 115 |  |
| TGG | AAT | GAA | TTC | CGT | CGT | AAA | CTG | ACC | TTC | TAT | CTG | AAA |
|  |  |  | 120 |  |  |  |  | 125 |  |  |  |  |
| ACC | TTG | GAG | AAC | GCG | CAG | GCT | CAA | CAG | [SEQ ID NO:101] | | | |

TABLE 5-continued

Example 10; pMON5978; [Met-Ala-(15-125)hIL-3]

```
                    15                              20                          25
ATG  GCT  AAC  TGC  TCT  AAC  ATG  ATC  GAT  GAA  ATC  ATC  ACC
                         30                        35
CAC  CTG  AAG  CAG  CCA  CCG  CTG  CCG  CTG  CTG  GAC  TTC  AAC
          40                    45                           50
AAC  CTC  AAT  GGT  GAA  GAC  CAA  GAT  ATC  CTG  ATG  GAA  AAT
                    55                        60
AAC  CTT  CGT  CGT  CCA  AAC  CTC  GAG  GCA  TTC  AAC  CGT  GCT
65                            70                            75
GTC  AAG  TCT  CTG  CAG  AAT  GCA  TCA  GCA  ATT  GAG  AGC  ATT
               80                        85                            90
CTT  AAA  AAT  CTC  CTG  CCA  TGT  CTG  CCC  CTG  GCC  ACG  GCC
                         95                        100
GCA  CCC  ACG  CGA  CAT  CCA  ATC  CAT  ATC  AAG  GAC  GGT  GAC
          105                       110                       115
TGG  AAT  GAA  TTC  CGT  CGT  AAA  CTG  ACC  TTC  TAT  CTG  AAA
                    120                       125
ACC  TTG  GAG  AAC  GCG  CAG  GCT  CAA  CAG  [SEQ ID NO:102]
```

Example 11; pMON5967; [Met-Ala-(15-125)hIL-3]

```
                    15                              20                          25
ATG  GCT  AAC  TGC  TCT  AAC  ATG  ATC  GAT  GAA  ATT  ATA  ACA
                         30                        35
CAC  TTA  AAG  CAG  CCA  CCT  TTG  CCT  TTG  CTG  GAC  TTC  AAC
          40                    45                           50
AAC  CTC  AAT  GGG  GAA  GAC  CAA  GAC  ATT  CTG  ATG  GAA  AAT
                    55                        60
AAC  CTT  CGA  AGG  CCA  AAC  CTG  GAG  GCA  TTC  AAC  AGG  GCT
65                            70                            75
GTC  AAG  AGT  TTA  CAG  AAT  GCA  TCA  GCA  ATT  GAG  AGC  ATT
               80                        85                            90
CTT  AAA  AAT  CTC  CTG  CCA  TGT  CTG  CCC  CTG  GCC  ACG  GCC
                         95                        100
GCA  CCC  ACG  CGA  CAT  CCA  ATC  CAT  ATC  AAG  GAC  GGT  GAC
          105                       110                       115
TGG  AAT  GAA  TTC  CGT  CGT  AAA  CTG  ACC  TTC  TAT  CTG  AAA
                    120                       125
ACC  TTG  GAG  AAC  GCG  CAG  GCT  CAA  CAG  [SEQ ID NO:103]
```

Further details known to those skilled in the art may be found in T. Maniatis, et al., *Molecular Cloning, A Laboratory Manual*, Cold Spring Harbor Laboratory (1982) and references cited therein, incorporated herein by reference; and in J. Sambrook, et al., *Molecular Cloning, A Laboratory Manual*, 2nd edition, Cold Spring Harbor Laboratory (1989) and references cited therein, incorporated herein by reference.

The following examples will illustrate the invention in greater detail although it will be understood that the invention is not limited to these specific examples.

Amino acids are shown herein by standard one letter or three letter abbreviations as follows:

| Abbreviation | Designation | Amino Acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Various other examples will be apparent to the person skilled in the art after reading the present disclosure without departing from the spirit and scope of the invention. It is intended that all such other examples be included within the scope of the appended claims.

EXAMPLE 1

Construction of pMON 5846 which encodes [Met-(1–133)hIL-3 (Arg129)]

A plasmid containing the gene for the cDNA of hIL-3 cloned into pUC18 on an EcoRI to HindIII fragment was obtained from British Biotechnology Limited (Cambridge, England). This plasmid was designated $pPO_{518}$. The purified plasmid DNA was cleaved by the restriction endonucleases NheI and BamHI. Approximately 0.5 micrograms of cleaved plasmid DNA was ligated to 1.0 picomoles of a pair of annealed oligonucleotides with the following sequence:

5'-CTAGCGATCTTTTAATAAGCTTG-3' [SEQ ID NO:1]
3'-GCTAGAAAATTATTCGAACCTAG-5' [SEQ ID NO:2]

The ligation mixture was used to transform competent JM101 cells to ampicillin resistance. Colonies were picked, and plasmid DNA was purified and subjected to restriction enzyme analysis. An isolate was identified in which the above oligonucleotide sequence had replaced the portion of the gene that encodes the extreme C terminus. Within the new sequence was a new stop codon, TAA, and a recognition site for the enzyme HindIII (AAGCTT). The new plasmid was designated pMON5846.

EXAMPLE 2

(a) Construction of expression vector plasmid pMON2341

The plasmid pMON2341 was used to supply the particular replicon and expression elements used for construction of many of the plasmids used to produce hIL-3 and hIL-3 muteins in *E. coli*. These expression elements are described in the materials and methods section. pMON2341 is derived from pMON5515 (Olins et al., 1988) and from pMON2429. pMON2429 consists of the phage mp18 (Yanisch-Perron et al., 1985) with a BclI fragment carrying the chloramphenicol acetyl transferase (cat) gene from pBR328 (Covarrubias et al., 1981) inserted into the BamHI site. The cat gene in pMON2429 has been altered from that in pBR328 by site directed mutagenesis (Kunkel, 1985). The recognition sites for NcoI and EcoRI which occur in the native gene were altered so that these two restriction enzymes no longer recognize these sites. The changes did not alter the protein specified by the gene. Also, an NcoI site was introduced at the N-terminus of the coding sequence so that it overlaps the initiator methionine coding sequence.

The steps involved in construction of pMON2341 are listed below:

(1) The DNAs of pMON5515 (Olins, P.O. et al., GENE, 1988) and pMON2429 were treated with NcoI and HindIII. The fragments were ligated and used to transform competent *E. coli* to ampicillin resistance. From these colonies, some were identified that were chloramphenicol resistant. From one of these colonies, plasmid DNA was isolated in which the rat atriopeptigen gene of pMON5515 had been replaced by the NcoI to HindIII fragment containing the cat gene from pMON2429. This fragment contains the recognition sites for several restriction enzymes in the portion derived from the multilinker region of mp18. The new plasmid was designated pMON2412.

(2) pMON2412 was treated with the enzyme ClaI which cleaves at one location in the pBR327 derived portion of the DNA. The protruding ends were rendered blunt by treatment with Klenow in the presence of nucleotide precursors. This DNA was mixed with an isolated 514 bp RsaI fragment derived from pEMBL8 (Dente et al., 1983). This RsaI fragment contains the origin of replication of phage f1. This ligation mixture was used to transform competent *E. coli* cells to ampicillin resistance. Among the plasmid DNAs isolated from these cells was pMON5578. This plasmid has the structure of pMON2412 with the f1 origin region inserted into the ClaI site. This is illustrated in the Figures and in Olins and Rangwala (1990).

(3) The DNA of pMON5578 was treated with restriction enzymes HindIII and MstII. The DNA was then treated with Klenow enzyme in the presence of nucleotide precursors to render the ends blunt. This treated DNA was ligated and used to transform competent *E. coli* to ampicillin resistance. From the ampicillin resistant colonies, one plasmid was recovered from which the portion between HindIII and MstII was absent. This deletion resulted in the removal of sequences from the plasmid which are recognized by a number of restriction endonuclease sites. The new plasmid was designated pMON5582.

(4) The DNA of pMON5582 was treated with SstII and BglII and ligated in the presence of annealed oligonucleotides with the sequences shown below.

5'-GGCAACAATTTCTACAAAACACTTGATACTGTATGAGCAT-
3'-CGCCGTTGTTAAAGATGTTTTGTGAACTATGACATACTCGTA-
ACAGTATAATTGCTTCAACAGAACA-3' [SEQ ID NO:3]
TGTCATATTAACGAAGTTGTCTTGTCTAG-5' [SEQ ID NO:4]

This sequence encodes the essential elements of the recA promoter of *E. coli* including the transcription start site and the lexA repressor binding site (the operator) (Sancar et al., 1980). The plasmid recovered from the ligation mixes contained this recA promoter in place of the one in pMON5582 (and in pMON5515). The functionality of the recA promoter was illustrated by Olins and Rangwala (1990). The new plasmid was designated pMON5594.

(5) To eliminate the single EcoRI site in pMON5594, the DNA was treated with EcoRI, then with Klenow in the presence of nucleotide precursors to render the ends blunt and then the DNA was ligated. From this ligation mix a plasmid was recovered whose DNA was not cleaved with EcoRI. This plasmid was designated pMON5630.

(6) To alter the single recognition site for PstI, plasmid pMON5630 was subjected to site directed mutagenesis (Kunkel, 1985). The oligonucleotide used in this procedure has the sequence shown below.

5'-CCATTGCTGCCGGCATCGTGGTC-3' [SEQ ID NO:5]

The result of the procedure was to construct pMON2341 which differs from pMON5630 in that the PstI site in the beta-lactamase gene was altered so that PstI no longer recognizes the site. The single amino acid change does not alter the amino acid sequence of the beta-lactamase protein.

Figure 5:
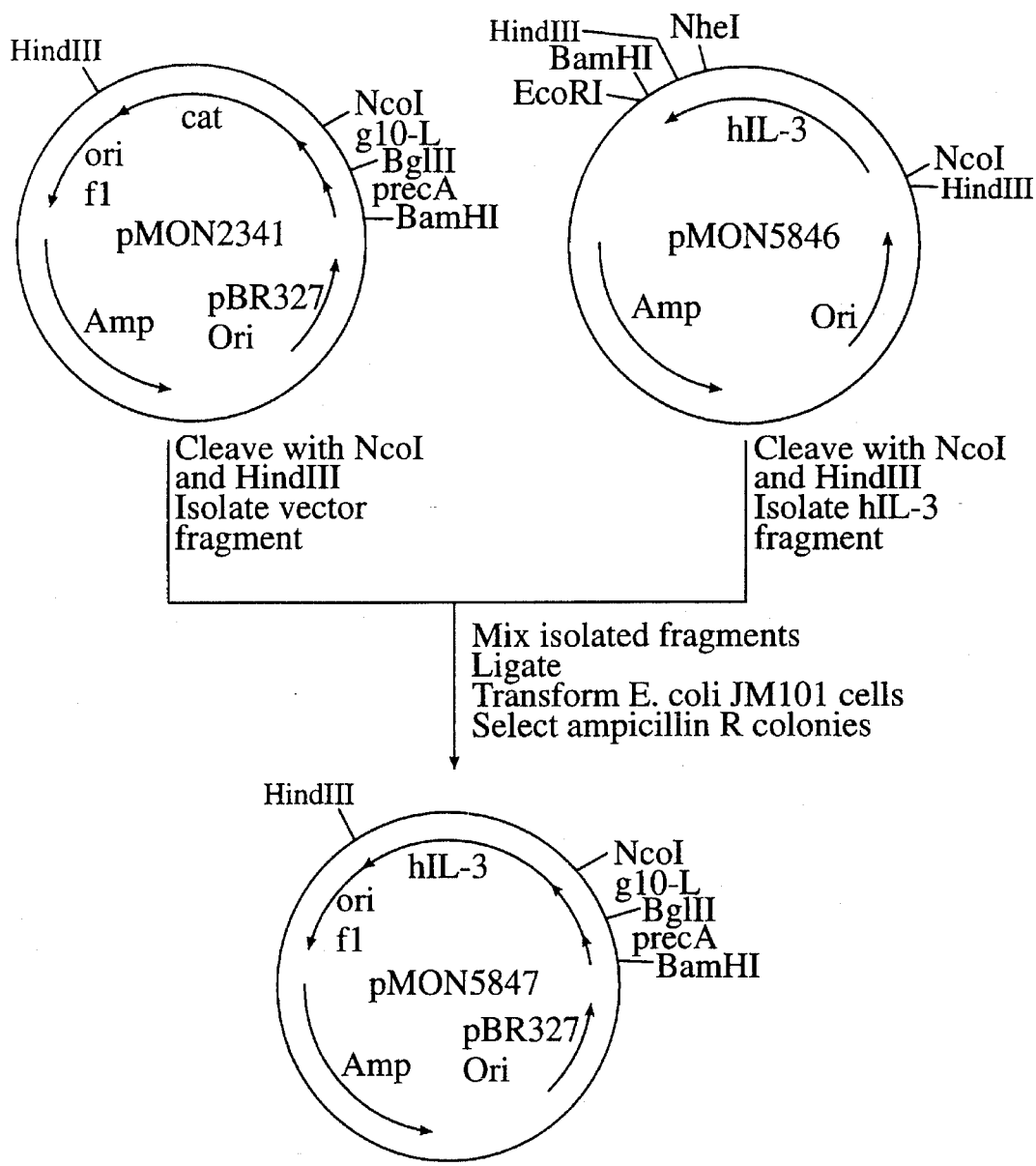
FIG. 5 shows the construction of the plasmid vector pMON5847 (ATCC 68912) which encodes [Met-(1–133) hIL-3 (Arg$^{129}$)].

(b) Construction of pMON5847 (FIG. 5) which encodes [Met-(1–133)hIL-3(Arg$^{129}$.)]

Plasmid pMON2341 was used to supply the replicon, promotor, ribosome binding site; transcription terminator and antibiotic resistance marker for the plasmids used to produce hIL-3 in *E. coli* from cDNA derived hIL-3 genes.

Plasmid pMON2341 was treated with restriction enzymes NcoI and HindIII. The restriction fragment containing the replication origin was purified. The DNA of plasmid pMON5846 was treated with NcoI and HindIII. The restriction fragment containing the hIL-3 gene was gel purified. These purified restriction fragments were mixed and ligated. The ligation mixture was used to transform competent JM101 cells to ampicillin resistance. Colonies were picked, and plasmid DNA was purified and analyzed using restriction enzymes. pMON5847 was identified as a plasmid with the replicon of pMON2341 and the hIL-3 gene in place of the chloramphenicol acetyl transferase gene. JM101 cells harboring this plasmid were cultured in M9 medium and treated with nalidixic acid as described above. Samples of the culture were examined for protein content. It was found that this hIL-3 mutein was produced at about 6% of total cell protein as measured on Coomassie stained polyacrylamide gels.

EXAMPLE 3

Figure 7:
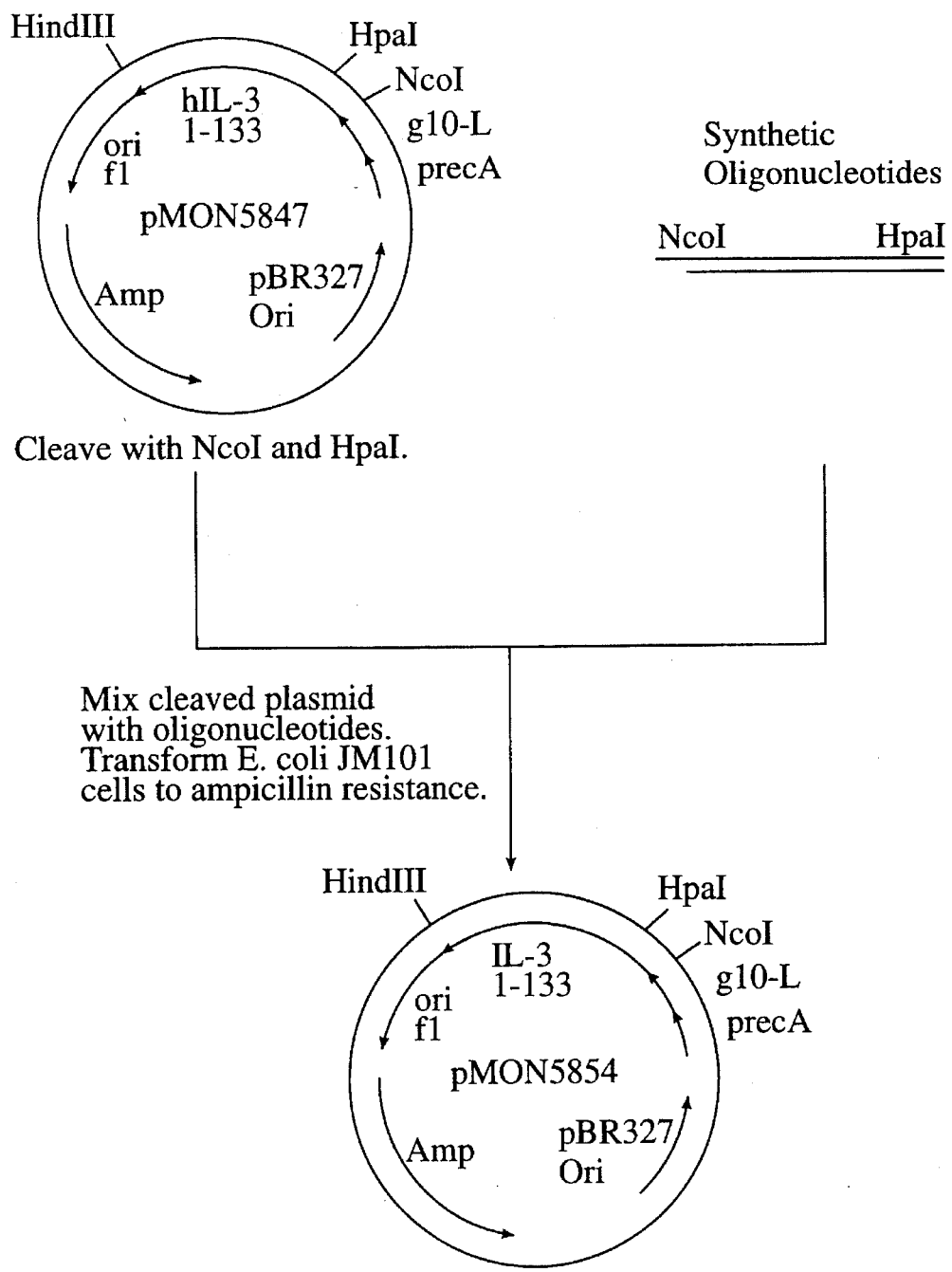
FIG. 7 shows the construction of the plasmid vector pMON5854 which encodes [Met-(1–133) hIL-3 (Arg$^{129}$)].
Figure 8:
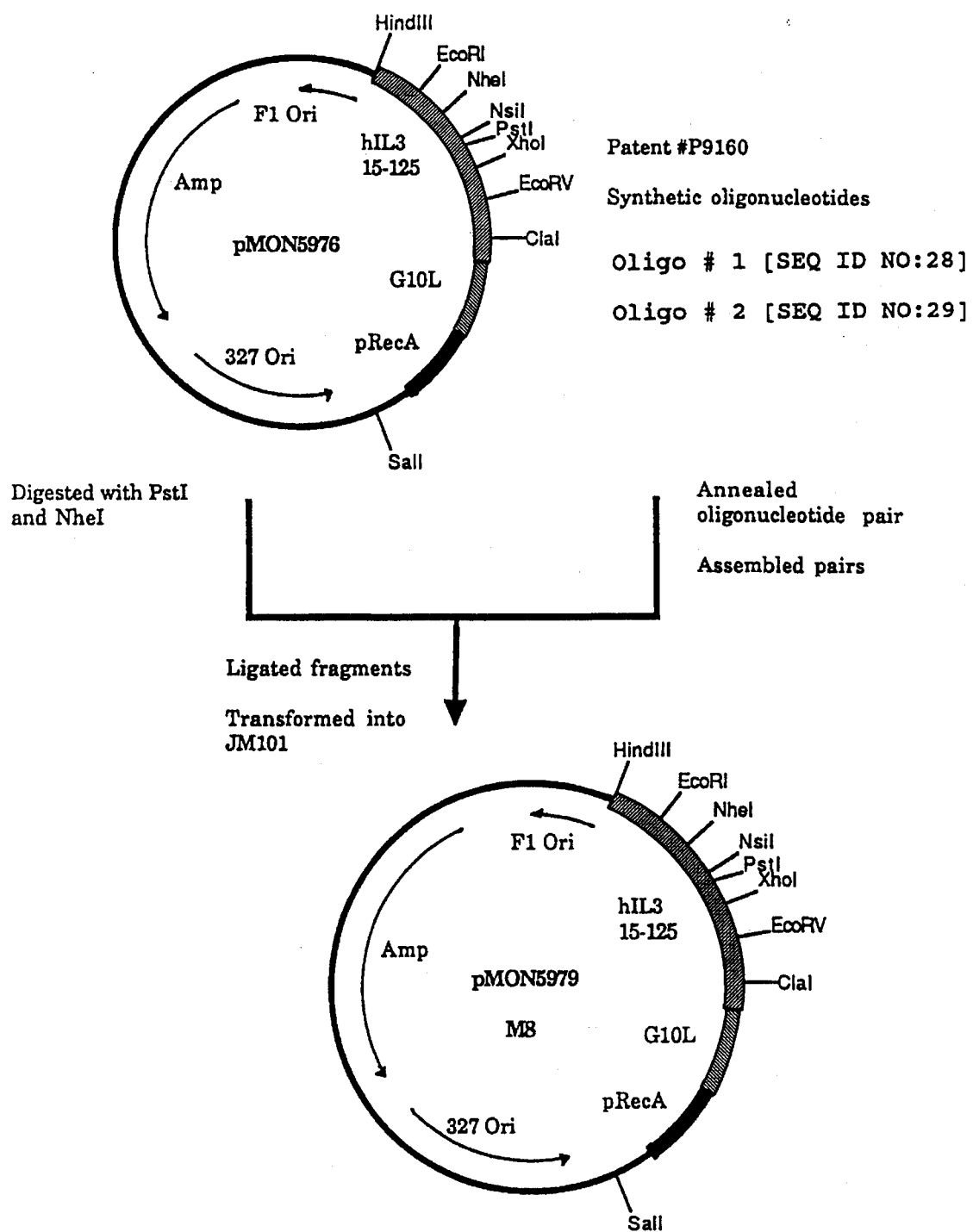
FIG. 8 shows the construction of pMON5979 which encodes (15–125)hIL-3 with an M8 insertion and Ala 101.
Figure 9:
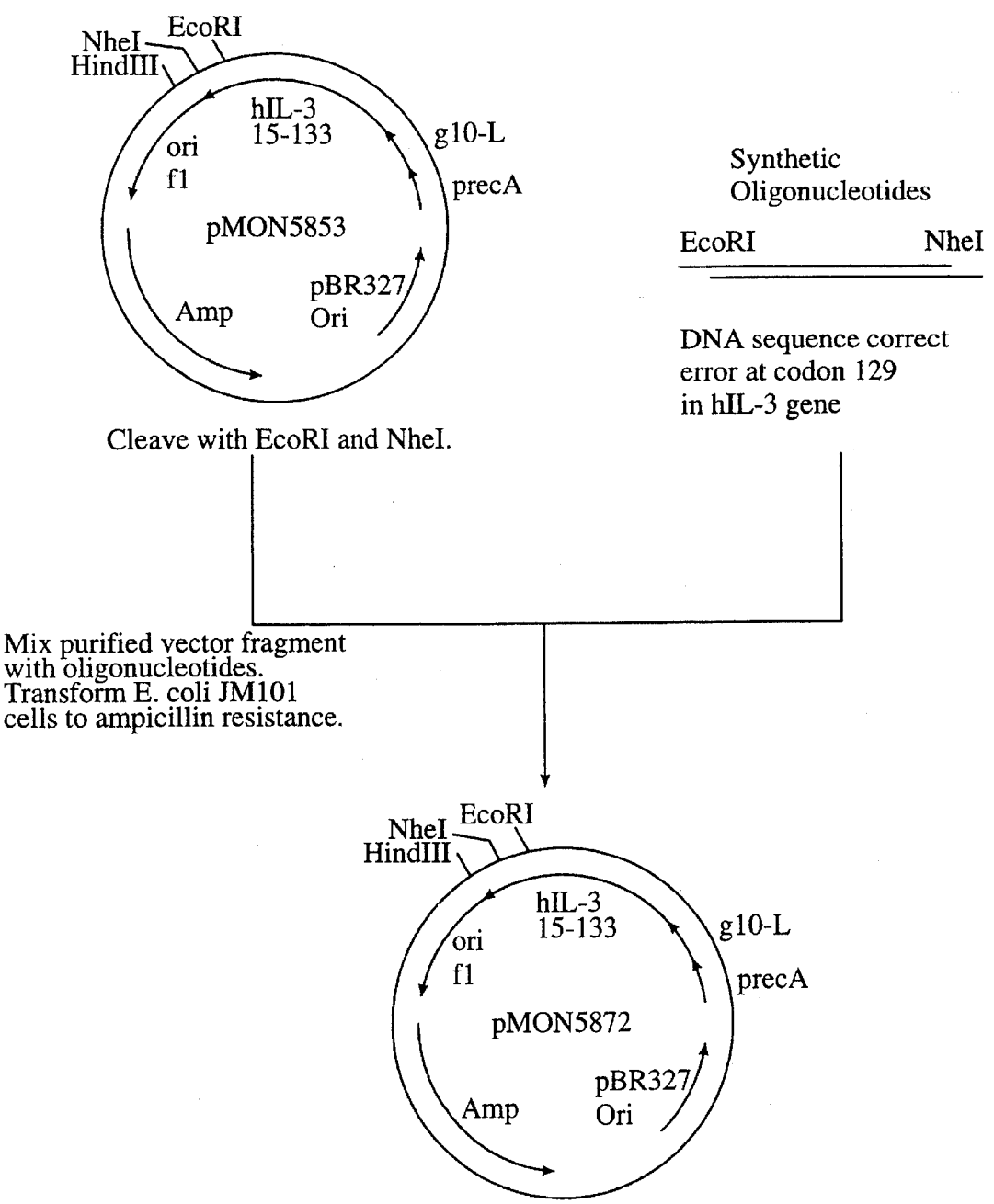
FIG. 9 shows the construction of the plasmid vector pMON5872 which encodes Met-(15–133) hIL-3.
Figure 10:
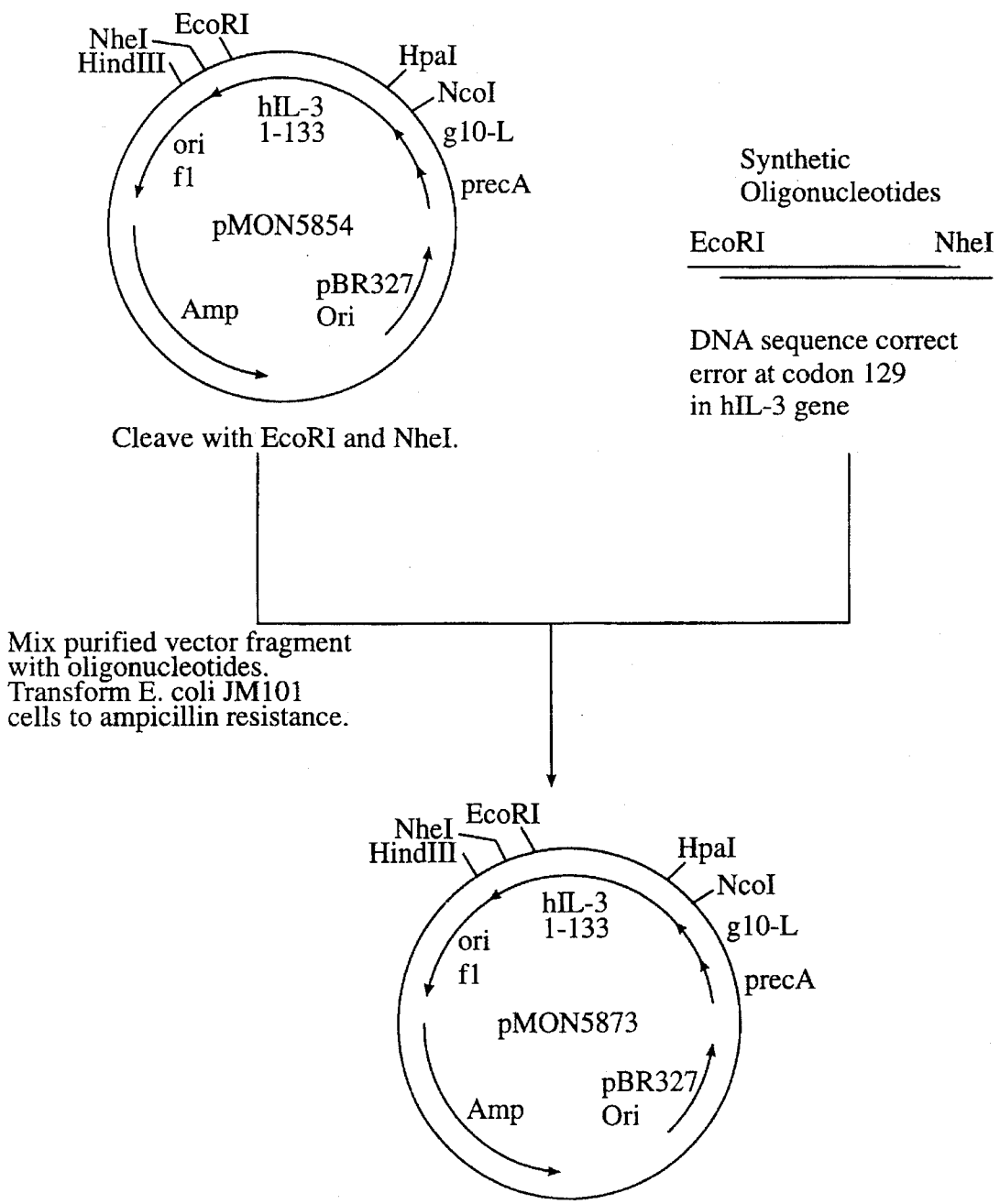
FIG. 10 shows the construction of the plasmid vector pMON5873 which encodes Met-(1–133) hIL-3.
Figure 12:
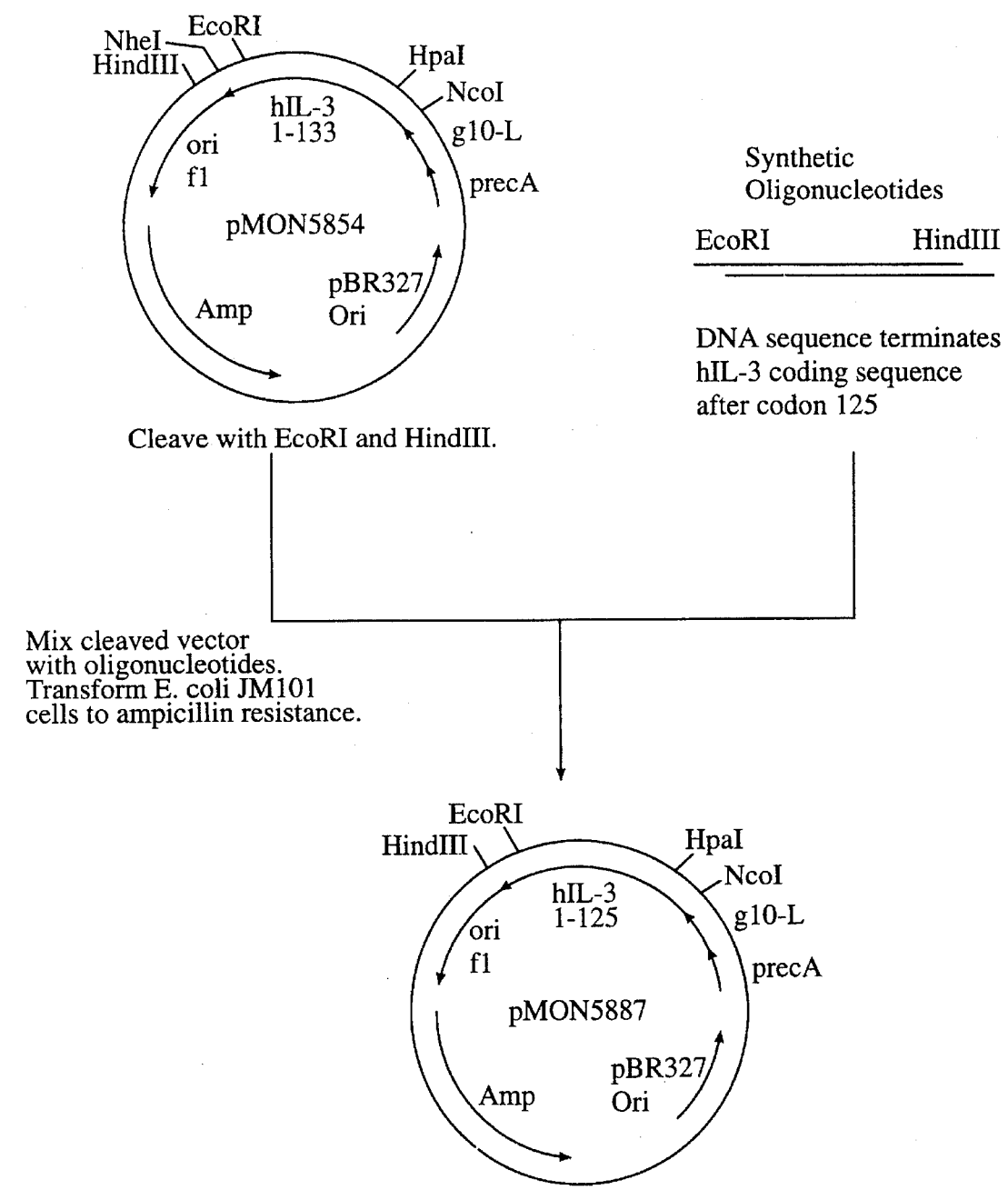
FIG. 12 shows the construction of the plasmid vector pMON5887 which encodes Met-(1–125) hIL-3.
Figure 13:
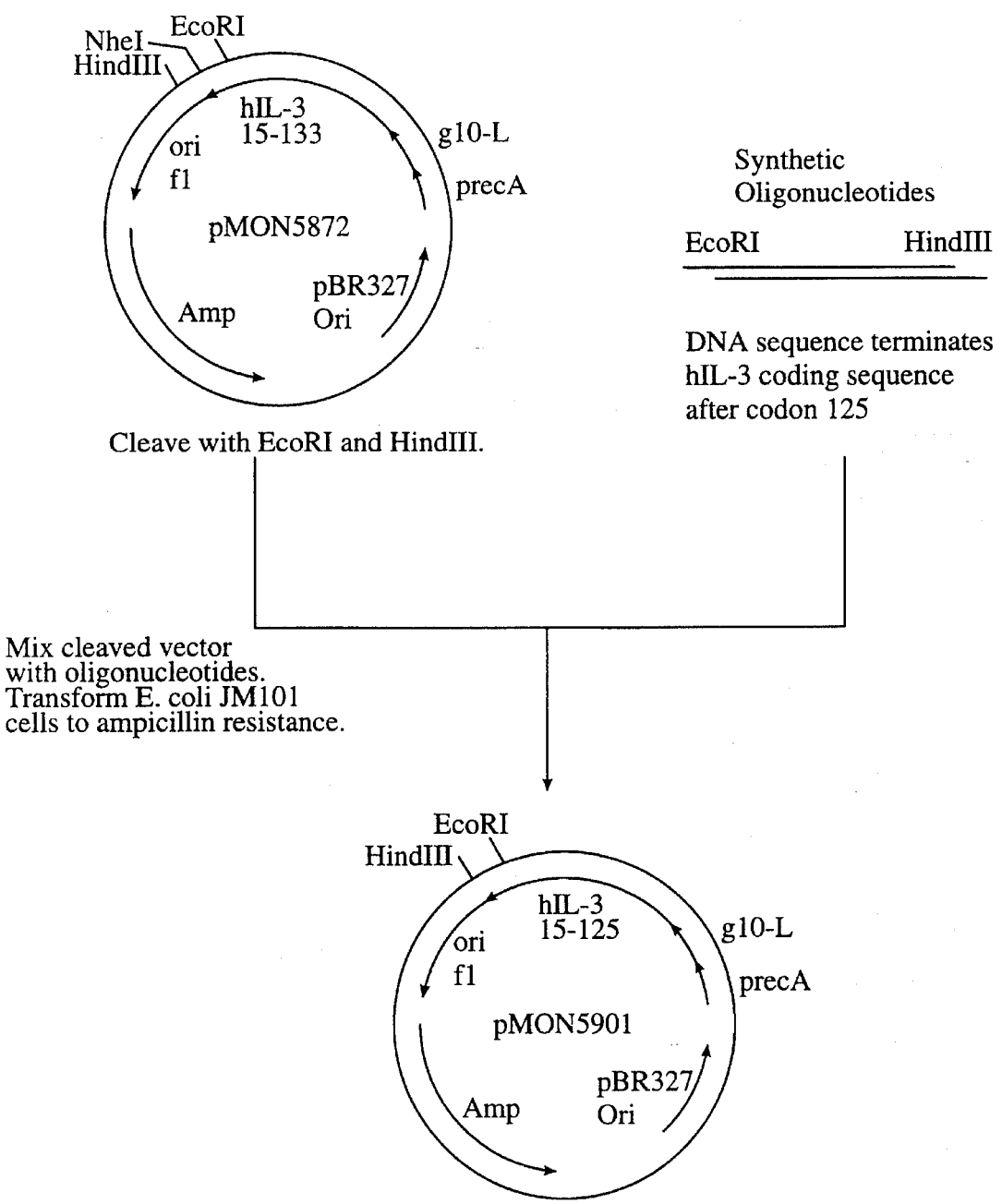
FIG. 13 shows the construction of the plasmid vector pMON5901 which encodes Met-(15–125) hIL-3.
Figure 14:
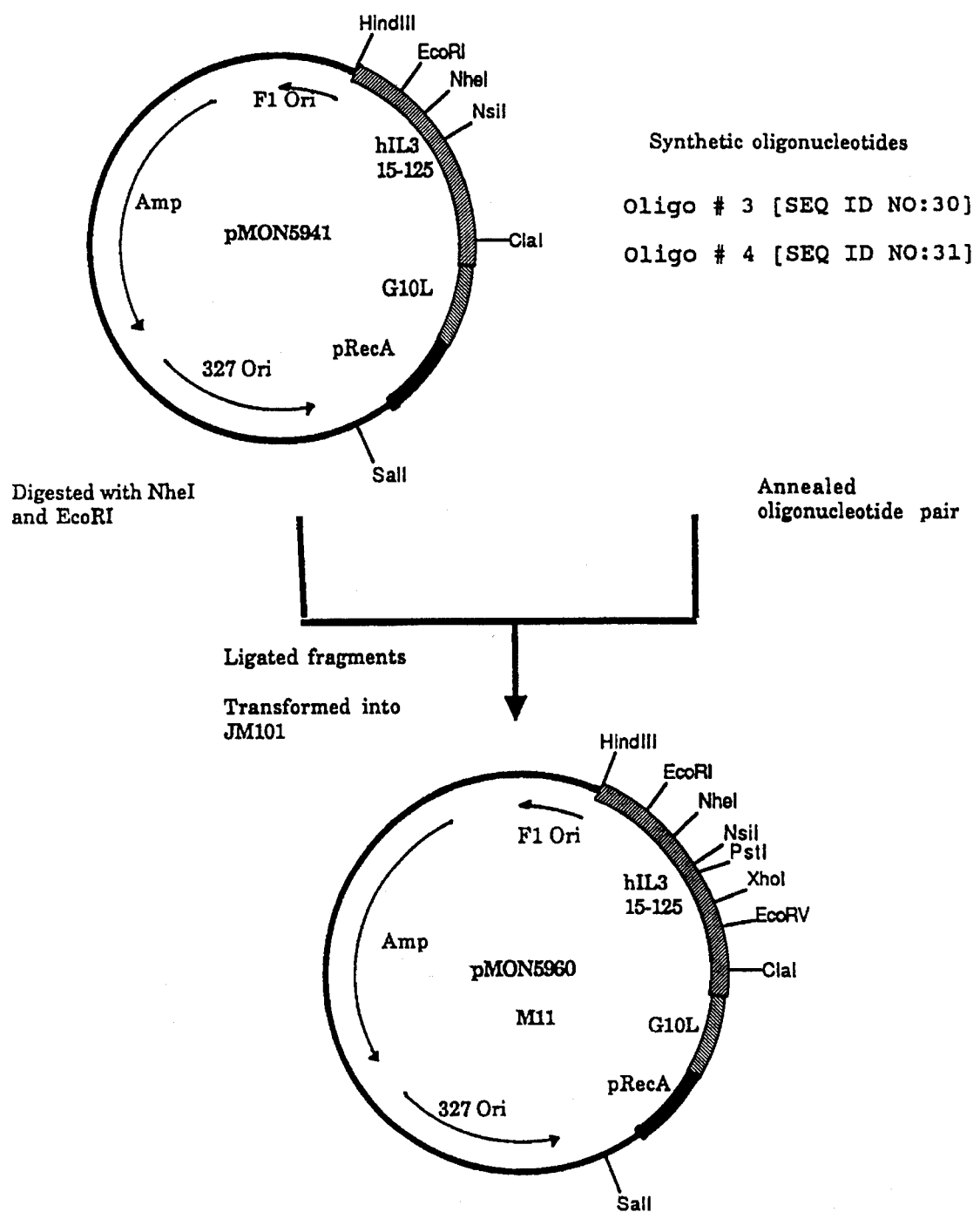
FIG. 14 shows the construction of pMON5960 which encodes (15–125)hIL-3 with an M11 insertion.
Figure 15:
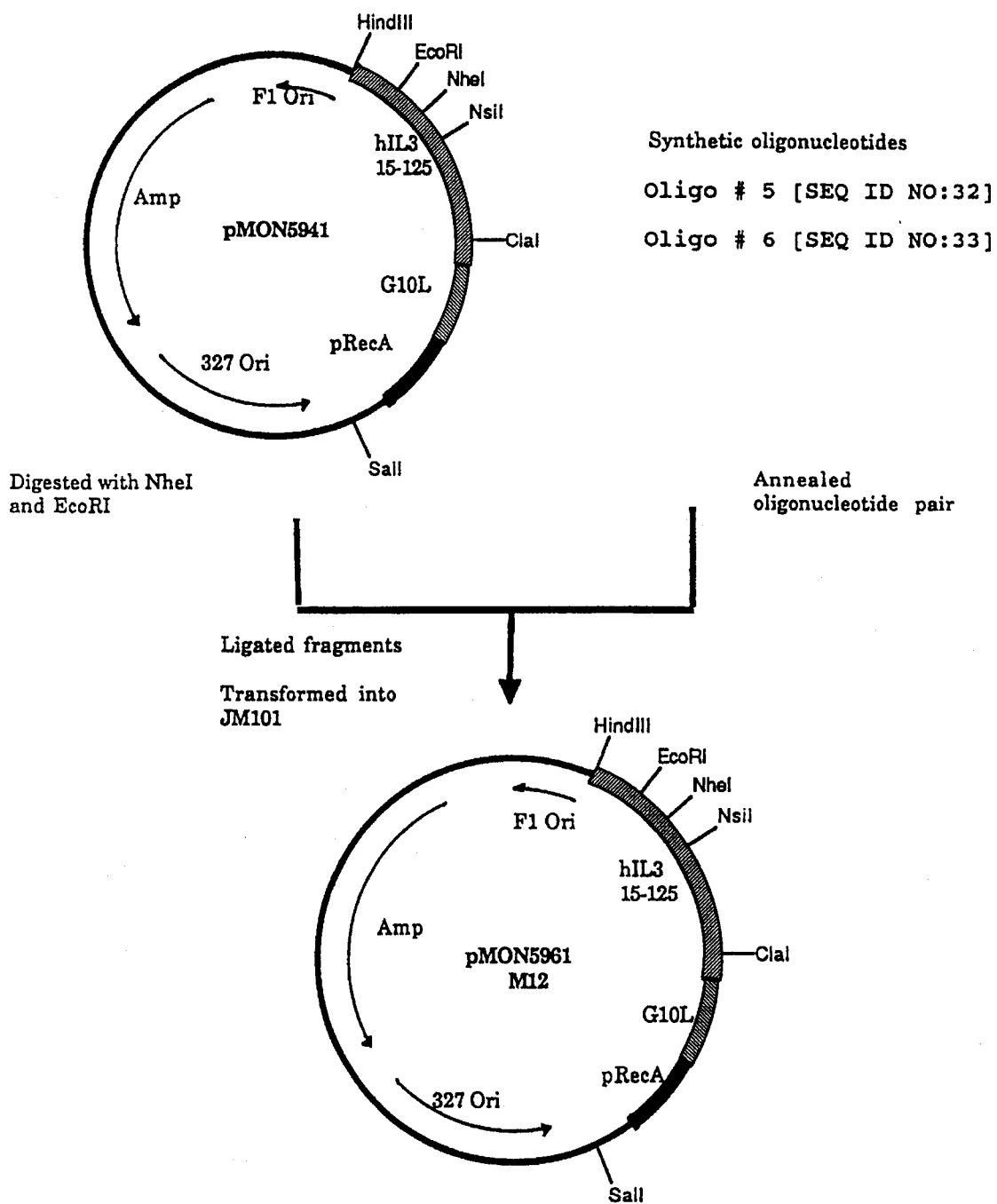
FIG. 15 shows the construction of pMON5961 which encodes (15–125)hIL-3 with an M12 insertion.
Figure 16:
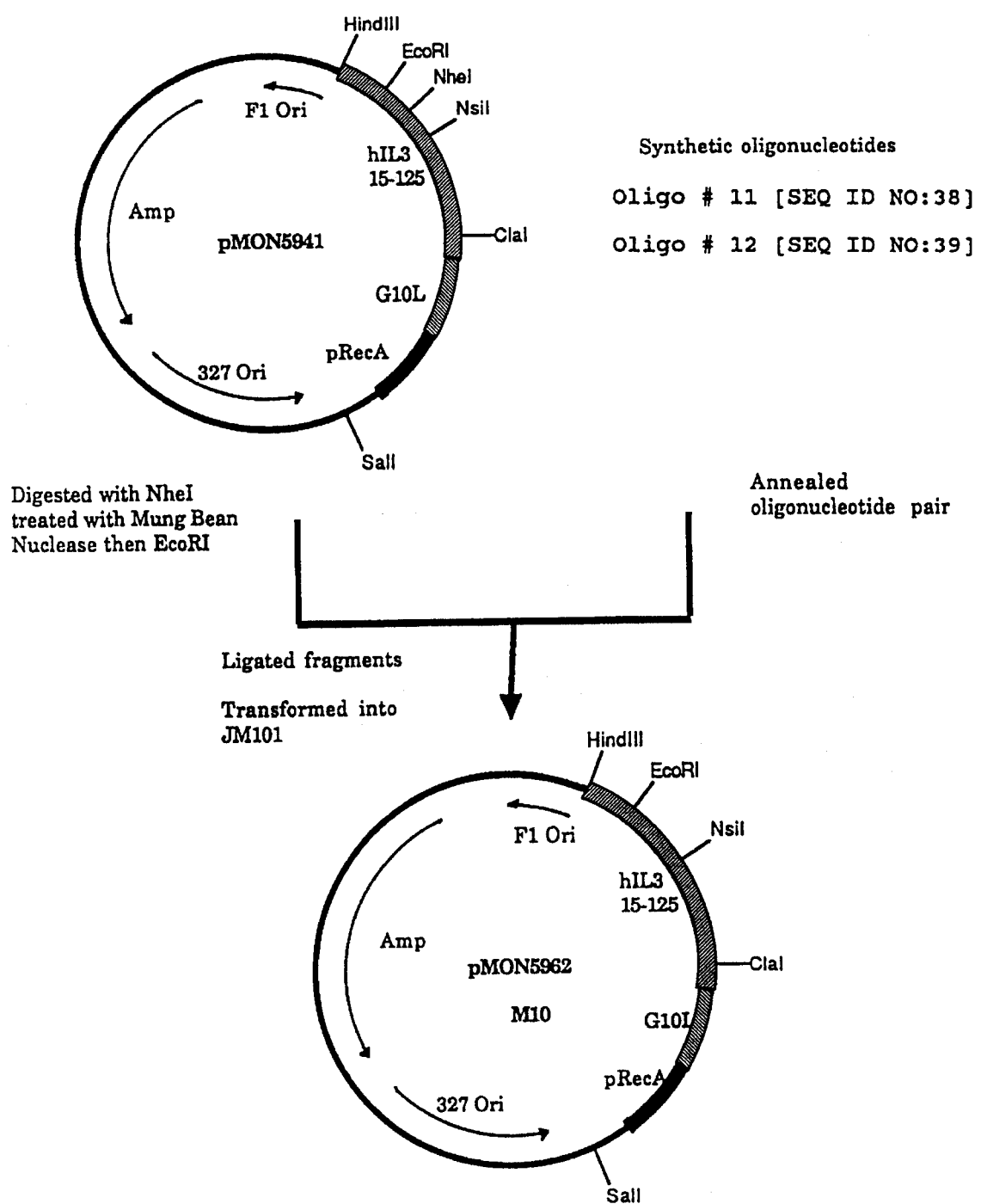
FIG. 16 shows the construction of pMON5962 which encodes (15–125)hIL-3 with an M10 insertion.
Figure 17:
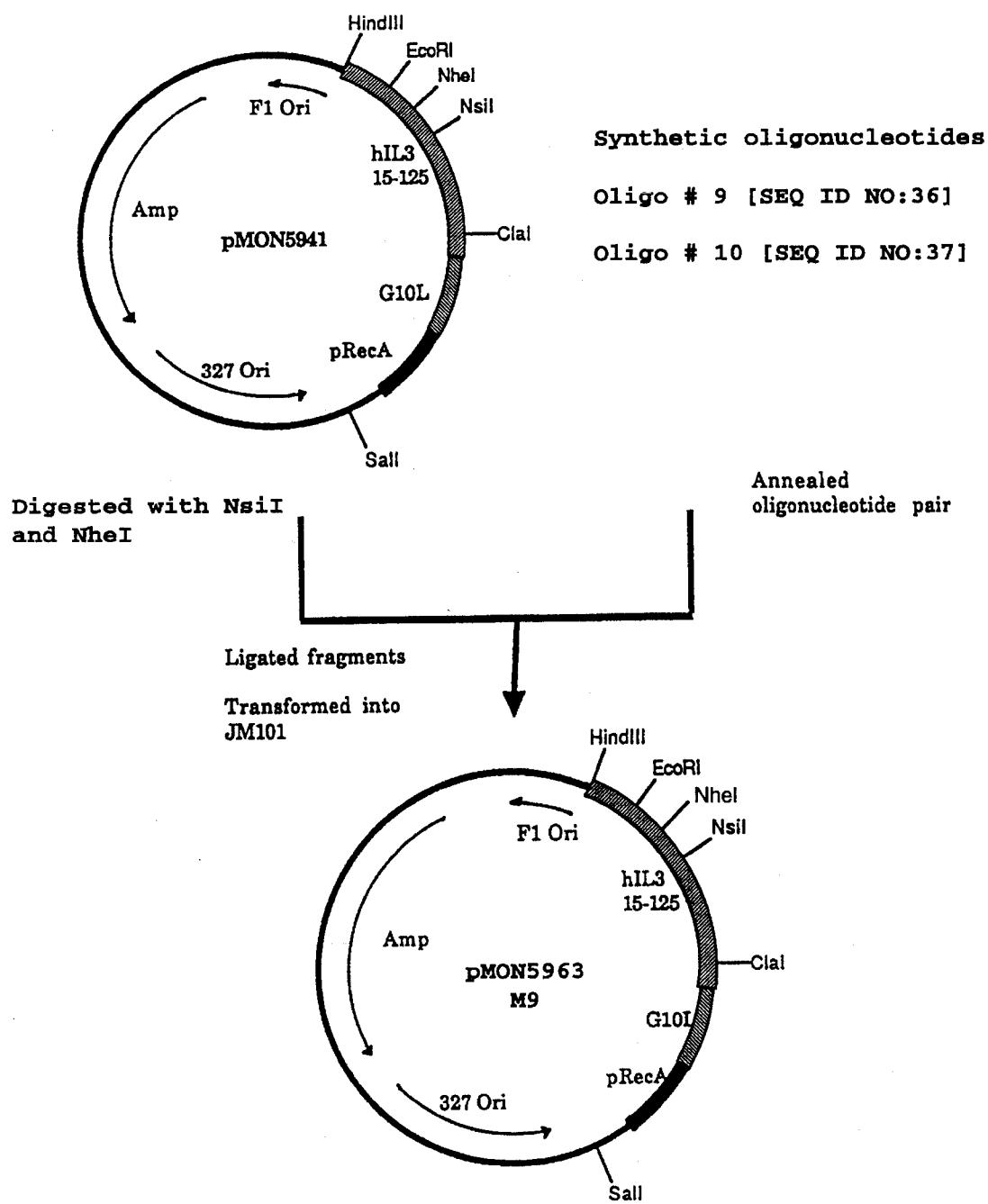
FIG. 17 shows the construction of pMON5963 which encodes (15–125)hIL-3 with an M9 insertion.
Figure 18:
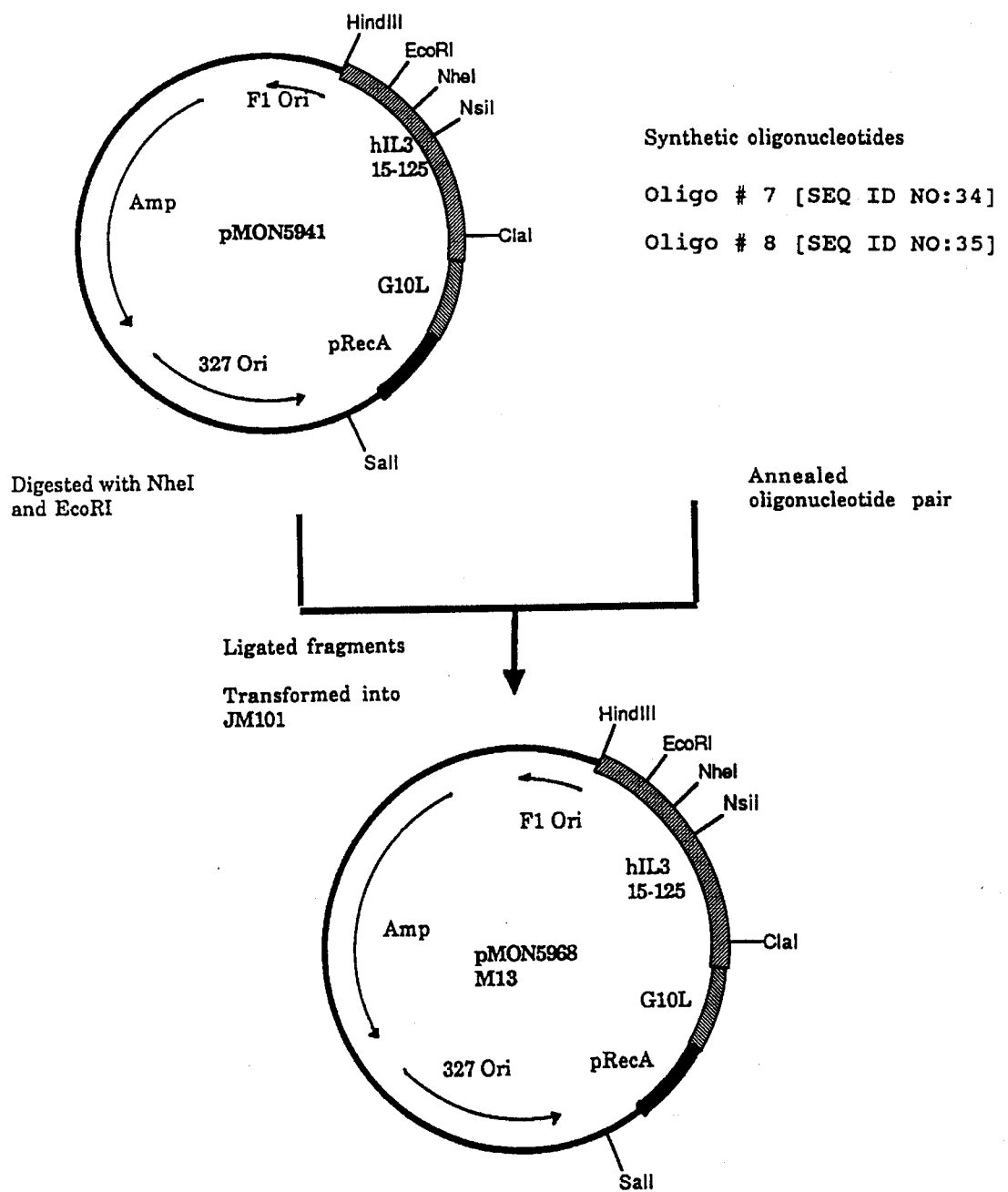
FIG. 18 shows the construction of pMON5968 which encodes (15–125)hIL-3 with an M13 insertion.

Construction of pMON5854 (FIG. 7) which encodes [Met-(1–133)hIL-3(Arg$^{129}$)]

To increase the accumulation of hIL-3 in *E. coli*, the coding sequence of the amino terminal portion of the protein was altered to more closely reflect the codon bias found in *E. coli* genes that produce high levels of proteins (Gouy and Gautier, 1982). To change the coding sequence for the amino terminal portion of the gene, a pair of synthetic oligonucleotides were inserted between the NcoI and HpaI sites within the coding sequence. About 0.5 micrograms of DNA of the plasmid pMON5847 (Example 2) was treated with NcoI and HpaI. This DNA was mixed with an annealed pair of oligonucleotides with the following sequence:

```
5'-CATGGCTCCAATGACTCAGACTACTTCTCTTAAGACT-
3'-CGAGGTTACTGAGTCTGATGAAGAGAATTCTGA-
TCTTGGGTT-3' [SEQ ID NO:6]
AGAACCCAA-5' [SEQ ID NO:7]
```

The fragments were ligated. The ligation mixture was used to transform competent JM101 to ampicillin resistance. Colonies were picked into broth. From the cultures plasmid DNA was made and examined for the presence of a DdeI site (CTNAG) which occurs in the synthetic sequence but not between the NcoI and HpaI sites in the sequence of pMON5847. The new recombinant plasmid was designated pMON5854. The nucleotide sequence of the DNA in the coding sequence of the amino terminal portion of the hIL-3 gene in pMON5854 was determined by DNA sequencing and found to be the same as that of the synthetic oligonucleotide used in ligation. Cultures of JM101 cells harboring this plasmid were grown and treated with nalidixic acid to induce production of the hIL-3 mutant protein. Analysis of the proteins on Coomassie gels showed that the accumulation of hIL-3 mutein was about 25% of total cell protein in cultures harboring pMON5854, significantly higher than it was in cultures harboring pMON5847.

EXAMPLE 4

Construction of pMON5853 (FIG. 6) which encodes [Met-(15–133)hIL-3(Arg$^{129}$)]

Plasmid DNA of pMON5847 (Example 2) was treated with NcoI. The restriction enzyme was inactivated by heat treatment (65° C. for 10 minutes). The DNA was then treated with large fragment of DNA polymerase I (Klenow) in the presence of all four nucleotide precursors. This produces DNA termini with non-overlapping ends. After 5 minutes at 37° C., the polymerase was inactivated by heat treatment at 65° C. for 10 minutes. The DNA was then treated with HpaI, an enzyme which produces non-overlapping termini. The DNA was ethanol precipitated and ligated. The ligation mixture was used to transform competent JM101 cells to ampicillin resistance. Colonies were picked and plasmid DNA isolated from cultures. The DNA was examined using restriction enzymes. A plasmid designated pMON5853 was identified as one containing a deletion of the amino terminal 14 codons of the hIL-3 gene. The DNA sequence for the junction of the ribosome binding site to the (15–133) hIL-3 gene was determined to be the following:

```
5'-AAGGAGATATATCCATGAACTGCTCTAAC-3'
[SEQ ID NO:8]
M N C S N [SEQ ID NO:9]
```

The lower line contains the one letter code for the amino acids specified by the coding sequence of the amino terminus of the 15-133 hIL-3 gene. These are methionine, asparagine, cysteine, serine and asparagine.

When cultures of JM101 cells harboring this plasmid were induced with nalidixic acid, it was found that a high level of hIL-3 accumulated in the cells.

The plasmid, pMON5853, encodes Met-(15–133) hIL-3 (Arg$^{129}$) which has the following amino acid sequence:

|     | Met | Asn | Cys | Ser | Asn | Met | Ile | Asp | Glu | Ile | Ile | Thr |
|-----|-----|-----|-----|-----|-----|-----|-----|-----|-----|-----|-----|-----|
| His | Leu | Lys | Gln | Pro | Pro | Leu | Pro | Leu | Leu | Asp | Phe | Asn |
| Asn | Leu | Asn | Gly | Glu | Asp | Gln | Asp | Ile | Leu | Met | Glu | Asn |
| Asn | Leu | Arg | Arg | Pro | Asn | Leu | Glu | Ala | Phe | Asn | Arg | Ala |
| Val | Lys | Ser | Leu | Gln | Asn | Ala | Ser | Ala | Ile | Glu | Ser | Ile |
| Leu | Lys | Asn | Leu | Leu | Pro | Cys | Leu | Pro | Leu | Ala | Thr | Ala |
| Ala | Pro | Thr | Arg | His | Pro | Ile | His | Ile | Lys | Asp | Gly | Asp |
| Trp | Asn | Glu | Phe | Arg | Arg | Lys | Leu | Thr | Phe | Tyr | Leu | Lys |
| Thr | Leu | Glu | Asn | Ala | Gln | Ala | Gln | Gln | Thr | Thr | Leu | Arg |
| Leu | Ala | Ile | Phe | [SEQ ID NO:10] | | | | | | | |

EXAMPLE 5

Construction of pMON5873 which encodes [Met-(1–133)hIL-3] and pMON5872 which encodes [Met-(15–133)hIL-3]

The gene obtained from British Biotechnology, Ltd. specified arginine at codon position 129. The amino acid specified in the native hIL-3 cDNA is serine. To produce a protein with the native sequence at this position, the portion of the coding sequence between the EcoRI site at codons 106 and 107 and the NheI site at codons 129 and 130 was replaced. Plasmid DNA of pMON5854 (Example 3) and pMON5853 (Example 4) were treated with EcoRI and NheI. The larger fragments of each were gel purified. These were ligated to a pair of an annealed oligonucleotides with the following sequences:

```
5'-AATTCCGTCGTAAACTGACCTTCTATCTGAAAACC-
3'-GGCAGCATTTGACTGGAAGATAGACTTTTGG-
TTGGAGAACGCGCAGGCTCAACAGACCACTCTGTCG-3' [SEQ ID NO:11]
AACCTCTTGCGCGTCCGAGTTGTCTGGTGAGACAGCGATC-5' [SEQ ID NO:12]
```

The ligation mixes were used to transform competent JM101 cells to ampicillin resistance. Colonies were picked into broth and grown. Plasmid DNA was isolated and examined for the presence of a new StyI recognition site present in the synthetic DNA and not in pMON5854 and pMON5853. The nucleotide sequence of the gene in the region between EcoRI and NheI was determined and found to be that of the synthetic oligonucleotides. The new plasmids were designated pMON5873 encoding [Met-(1–133)hIL-3] and pMON5872 encoding [Met-(15–133)hIL-3].

The plasmid, pMON5873, encodes Met-(1–133)hIL-3 which has the following amino acid sequence:

| Met | Ala | Pro | Met | Thr | Gln | Thr | Thr | Ser | Leu | Lys | Thr | Ser |
|-----|-----|-----|-----|-----|-----|-----|-----|-----|-----|-----|-----|-----|
| Trp | Val | Asn | Cys | Ser | Asn | Met | Ile | Asp | Glu | Ile | Ile | Thr |
| His | Leu | Lys | Gln | Pro | Pro | Leu | Pro | Leu | Leu | Asp | Phe | Asn |
| Asn | Leu | Asn | Gly | Glu | Asp | Gln | Asp | Ile | Leu | Met | Glu | Asn |
| Asn | Leu | Arg | Arg | Pro | Asn | Leu | Glu | Ala | Phe | Asn | Arg | Ala |
| Val | Lys | Ser | Leu | Gln | Asn | Ala | Ser | Ala | Ile | Glu | Ser | Ile |
| Leu | Lys | Asn | Leu | Leu | Pro | Cys | Leu | Pro | Leu | Ala | Thr | Ala |
| Ala | Pro | Thr | Arg | His | Pro | Ile | His | Ile | Lys | Asp | Gly | Asp |
| Trp | Asn | Glu | Phe | Arg | Arg | Lys | Leu | Thr | Phe | Tyr | Leu | Lys |
| Thr | Leu | Glu | Asn | Ala | Gln | Ala | Gln | Gln | Thr | Thr | Leu | Ser |
| Leu | Ala | Ile | Phe | [SEQ ID NO:13] | | | | | | | | |

The plasmid, pMON5872, encodes Met-(15–133)hIL-3 which has the following amino acid sequence:

| Met | Asn | Cys | Ser | Asn | Met | Ile | Asp | Glu | Ile | Ile | Thr | |
|-----|-----|-----|-----|-----|-----|-----|-----|-----|-----|-----|-----|-----|
| His | Leu | Lys | Gln | Pro | Pro | Leu | Pro | Leu | Leu | Asp | Phe | Asn |
| Asn | Leu | Asn | Gly | Glu | Asp | Gln | Asp | Ile | Leu | Met | Glu | Asn |
| Asn | Leu | Arg | Arg | Pro | Asn | Leu | Glu | Ala | Phe | Asn | Arg | Ala |
| Val | Lys | Ser | Leu | Gln | Asn | Ala | Ser | Ala | Ile | Glu | Ser | Ile |
| Leu | Lys | Asn | Leu | Leu | Pro | Cys | Leu | Pro | Leu | Ala | Thr | Ala |
| Ala | Pro | Thr | Arg | His | Pro | Ile | His | Ile | Lys | Asp | Gly | Asp |
| Trp | Asn | Glu | Phe | Arg | Arg | Lys | Leu | Thr | Phe | Tyr | Leu | Lys |
| Thr | Leu | Glu | Asn | Ala | Gln | Ala | Gln | Gln | Thr | Thr | Leu | Ser |
| Leu | Ala | Ile | Phe | [SEQ ID NO:14] | | | | | | | | |

EXAMPLE 6

Construction of pMON5887 which encodes [Met-(1–125)hIL-3]

The plasmid DNA of pMON5854 (Example 3) was treated with EcoRI and HindIII and the larger fragment gel was purified. About 0.5 microgram of this DNA was ligated to 1 picomole of an annealed pair of oligonucleotides which encode amino acids 107 through 125 of hIL-3. The sequences of these oligonucleotides are shown below.

EcoRI to HindIII
5'-AATTCCGTCGTAAACTGACCTTCTATCTGAAAA-
3'-GGCAGCATTTGACTGGAAGATAGACTTTT-
CCTTGGAGAACGCGCAGGCTCAACAGTAATA-3' [SEQ ID NO:15]
GGAACCTCTTGCGCGTCCGAGTTGTCATTATTCGA-5' [SEQ ID NO:16]

After ligation, the DNA was used to transform competent JM101 cells to ampicillin resistance. Colonies were picked into broth and plasmid DNA was isolated from each culture.

Restriction analysis of the plasmid DNA showed the presence of an EcoRI to HindIII fragment smaller than that of pMON5854. The nucleotide sequence of the portion of the coding sequence between the EcoRI and HindIII sites was determined to confirm the accuracy of the replaced sequence. The new plasmid was designated pMON5887 encoding Met-(1–125)hIL-3 which has the following amino acid sequence:

| Met | Ala | Pro | Met | Thr | Gln | Thr | Thr | Ser | Leu | Lys | Thr | Ser |
|-----|-----|-----|-----|-----|-----|-----|-----|-----|-----|-----|-----|-----|
| Trp | Val | Asn | Cys | Ser | Asn | Met | Ile | Asp | Glu | Ile | Ile | Thr |
| His | Leu | Lys | Gln | Pro | Pro | Leu | Pro | Leu | Leu | Asp | Phe | Asn |
| Asn | Leu | Asn | Gly | Glu | Asp | Gln | Asp | Ile | Leu | Met | Glu | Asn |
| Asn | Leu | Arg | Arg | Pro | Asn | Leu | Glu | Ala | Phe | Asn | Arg | Ala |
| Val | Lys | Ser | Leu | Gln | Asn | Ala | Ser | Ala | Ile | Glu | Ser | Ile |
| Leu | Lys | Asn | Leu | Leu | Pro | Cys | Leu | Pro | Leu | Ala | Thr | Ala |

| | | | | | | | | | | | |
|---|---|---|---|---|---|---|---|---|---|---|---|
| Ala | Pro | Thr | Arg | His | Pro | Ile | His | Ile | Lys | Asp | Gly | Asp |
| Trp | Asn | Glu | Phe | Arg | Arg | Lys | Leu | Thr | Phe | Tyr | Leu | Lys |
| Thr | Leu | Glu | Asn | Ala | Gln | Ala | Gln | Gln | [SEQ ID NO:17] | | |

EXAMPLE 7

Construction of pMON5901 which encodes [Met-(15–125)hIL-3]

The plasmid DNA of pMON5872 was treated with EcoRI and HindIII. The restriction enzymes were inactivated by heating at 65° C., and 0.5 picograms of the DNA was mixed with 1 picomole of the pair of annealed oligonucleotides used in the construction of pMON5887, above. The ligation mix was used to transform competent *E. coli* JM101 cells to ampicillin resistance. Colonies were chosen for analysis of plasmid DNA. As above, new recombinants were identified whose EcoRI to HindIII fragment was smaller than that of pMON5872. The nucleotide sequence of the replaced portion of the gene was determined. The new plasmid was designated pMON5901 encoding [Met-(15–125)hIL-3] which has the following amino acid sequence:

| Met | Asn | Cys | Ser | Asn | Met | Ile | Asp | Glu | Ile | Ile | Thr |
|---|---|---|---|---|---|---|---|---|---|---|---|
| His | Leu | Lys | Gln | Pro | Pro | Leu | Pro | Leu | Leu | Asp | Phe | Asn |
| Asn | Leu | Asn | Gly | Glu | Asp | Gln | Asp | Ile | Leu | Met | Glu | Asn |
| Asn | Leu | Arg | Arg | Pro | Asn | Leu | Glu | Ala | Phe | Asn | Arg | Ala |
| Val | Lys | Ser | Leu | Gln | Asn | Ala | Ser | Ala | Ile | Glu | Ser | Ile |
| Leu | Lys | Asn | Leu | Leu | Pro | Cys | Leu | Pro | Leu | Ala | Thr | Ala |
| Ala | Pro | Thr | Arg | His | Pro | Ile | His | Ile | Lys | Asp | Gly | Asp |
| Trp | Asn | Glu | Phe | Arg | Arg | Lys | Leu | Thr | Phe | Tyr | Leu | Lys |
| Thr | Leu | Glu | Asn | Ala | Gln | Ala | Gln | Gln | [SEQ ID NO:18] | | |

EXAMPLE 8

Construction of pMON5969 which encodes [Met-(15–125)hIL-3]

pMON5969 encodes Met-(15–125)hIL-3 using *E. coli* codons, which are represented in highly expressed *E. Coli* genes, between amino acids 20–70. This intermediate cloning construct has additional restriction sites which can be used to build other hIL-3 variants. The plasmid DNA of pMON5901, grown in a dam-*E. coli* strain, was cleaved with ClaI and NsiI and three annealed pairs of oligonucleotides (Oligos #31 to #36) having the sequence shown in FIG. 2 (ClaI to NsiI Replacement Fragment) was ligated to the vector. The ligation mix was used to transform competent *E. coli* JM101 cells to ampicillin resistance. Individual colonies were picked, and cultures were grown for plasmid DNA isolation. Plasmid DNA was isolated from cultures and screened for the presence of new restriction sites EcoRV, XhoI, and PstI. The nucleotide sequence of the substituted portion was determined and found to be that of the synthetic oligonucleotides. Cultures were induced for protein expression and the expressed protein was bioassayed.

The nucleotide and amino acid sequence of the ClaI to NsiI replacement fragment used between the ClaI and NsiI sites of the hIL-3 gene is shown in FIG. 2. The codon choice used in the fragment was one found in highly expressed *E. Coli* genes. Three new unique restriction sites, EcoRV, XhoI and PstI were introduced for the purpose of inserting synthetic gene fragments. The portion of the coding sequence shown in FIG. 2 encodes amino acids 20–70 of hIL-3. It is contained in the hIL-3 mutein gene in pMON5969.

EXAMPLE 9

Construction of pMON5976 which encodes [Met-(15–125)hIL-3 (Ala$^{101}$)]

At codons 86–87 of a nucleotide sequence coding for (15–125)hIL-3, an NheI site was introduced (Example 13). The plasmid with this alteration was designated pMON5941. This plasmid encodes Met-(15–125)hIL-3 which is altered at position 101 by replacement of aspartate by alanine.

The plasmid DNA of pMON5941 isolated from the dam-*E. coli* strain GM48 was cleaved with ClaI and NsiI and ligated to 1 picomole of an annealed assembly of six oligonucleotides encoding amino acids 20–70 of hIL-3 (FIG. 2). This synthetic fragment encodes three unique restriction sites, EcoRV, XhoI and PstI. The sequence of these oligonucleotides is shown in FIG. 2.

The resulting ligation mix was used to transform competent *E. coli* JM101 cells to ampicillin resistance. Plasmid DNA was isolated from cultures of these transformed cells, and the inserted fragment was determined to have both an EcoRV and NheI site. The nucleotide sequence of the region between ClaI and NsiI was determined and found to be that of the synthetic oligonucleotides. The new plasmid was designated pMON5976, and cells containing it were induced for protein production. Sonicated cell pellets and supernatants were used for protein purification and bioassay.

Plasmid pMON5976 encodes Met-(15–125)hIL-3(Ala$^{101}$) which has the following amino acid sequence:

| Met | Asn | Cys | Ser | Asn | Met | Ile | Asp | Glu | Ile | Ile | Thr |
|---|---|---|---|---|---|---|---|---|---|---|---|
| His | Leu | Lys | Gln | Pro | Pro | Leu | Pro | Leu | Leu | Asp | Phe | Asn |
| Asn | Leu | Asn | Gly | Glu | Asp | Gln | Asp | Ile | Leu | Met | Glu | Asn |
| Asn | Leu | Arg | Arg | Pro | Asn | Leu | Glu | Ala | Phe | Asn | Arg | Ala |
| Val | Lys | Ser | Leu | Gln | Asn | Ala | Ser | Ala | Ile | Glu | Ser | Ile |
| Leu | Lys | Asn | Leu | Leu | Pro | Cys | Leu | Pro | Leu | Ala | Thr | Ala |
| Ala | Pro | Thr | Arg | His | Pro | Ile | His | Ile | Lys | Ala | Gly | Asp |
| Trp | Asn | Glu | Phe | Arg | Arg | Lys | Leu | Thr | Phe | Tyr | Leu | Lys |

Thr Leu Glu Asn Ala Gln Ala Gln Gln [SEQ ID NO:19]

EXAMPLE 10

Construction of pMON5978 which encodes [Met-Ala-(15–125)hIL-3]

The dam- plasmid DNA of pMON5967 isolated from *E. coli* GM48 was cleaved with ClaI and NsiI and ligated to 1 picomole of an annealed assembly of six oligonucleotides encoding hIL-3 amino acids 20–70 (FIG. 2). This synthetic fragment encodes three unique restriction sites, EcoRV, XhoI and PstI. The sequence of these oligonucleotides is shown in FIG. 2.

The resulting ligation mix was used to transform competent *E. coli* JM101 cells to ampicillin resistance. Plasmid DNA was isolated from cultures of these transformed cells and screened with XbaI and EcoRV for the presence of the new restriction site EcoRV. The DNA sequence of the region between ClaI and NsiI was determined and found to be the same as that of the synthetic oligonucleotides. The new plasmid was designated pMON5978, and cells containing it were induced for protein production. Sonicated cell pellets and supernatants were used for protein purification and bioassay.

Plasmid pMON5978 encodes [Met-Ala-(15–125)hIL-3] which has the following amino acid sequence:

| Met | Ala | Asn | Cys | Ser | Asn | Met | Ile | Asp | Glu | Ile | Ile | Thr |
|---|---|---|---|---|---|---|---|---|---|---|---|---|
| His | Leu | Lys | Gln | Pro | Pro | Leu | Pro | Leu | Leu | Asp | Phe | Asn |
| Asn | Leu | Asn | Gly | Glu | Asp | Gln | Asp | Ile | Leu | Met | Glu | Asn |
| Asn | Leu | Arg | Arg | Pro | Asn | Leu | Glu | Ala | Phe | Asn | Arg | Ala |
| Val | Lys | Ser | Leu | Gln | Asn | Ala | Ser | Ala | Ile | Glu | Ser | Ile |
| Leu | Lys | Asn | Leu | Leu | Pro | Cys | Leu | Pro | Leu | Ala | Thr | Ala |
| Ala | Pro | Thr | Arg | His | Pro | Ile | His | Ile | Lys | Asp | Gly | Asp |
| Trp | Asn | Glu | Phe | Arg | Arg | Lys | Leu | Thr | Phe | Tyr | Leu | Lys |
| Thr | Leu | Glu | Asn | Ala | Gln | Ala | Gln | Gln | [SEQ ID NO:20] | | | |

EXAMPLE 11

Construction of pMON5967 which encodes [Met-Ala-(15–125)hIL-3]

The dam- plasmid DNA of pMON5887 isolated from *E. coli* GM48 was cleaved with NcoI and ClaI and ligated to 1 picomole of an annealed pair of oligonucleotides, Nco 1 and Nco 2, encoding amino acids [Met Ala (15–20)hIL-3]. The sequence of these oligonucleotides is shown below.

5'-CATGGCTAACTGCTCTAACATGAT-3' [SEQ ID NO:21]
3'-CGATTGACGAGATTGTACTAGC-5' [SEQ ID NO:22]

The resulting ligation mix was used to transform competent *E. Coli* JM101 cells to ampicillin resistance. Plasmid DNA was isolated from cultures of these transformed cells and the size of the inserted fragment was determined to be smaller than that of pMON5887 by restriction analysis using NcoI and NsiI. The nucleotide sequence of the region between NcoI and ClaI was determined and found to be that of the synthetic oligonucleotides. The new plasmid was designated pMON5967 and cells containing it were induced for protein production. Sonicated cell pellets and supernatants were used for protein purification and bio-assay.

EXAMPLE 12

Construction of pMON5917 which encodes [Met-(15–88)hIL-3]

The plasmid DNA of pMON 5853 was cleaved with NsiI and HindIII and ligated to an annealed pair of oligonucleotides encoding (70–88)hIL-3 with a new NheI endonuclease restriction site at codons 86–87. The sequence of these oligonucleotides is shown in Example 18.

The ligation mixture was used to transform competent *E. coli*. JM101 cells, and ampicillin resistant colonies were picked. Plasmid DNA isolated from individual colonies was screened for the presence of the new NheI restriction site. The nucleotide sequence of the substituted portion was determined and found to be that of the synthetic oligonucleotides. The new plasmid was designated pMON5917 encoding Met-(15–88)hIL-3 containing a new NheI site at codons 86–87.

Plasmid pMON5917 encodes Met-(15–88)hIL-3 which has the following amino acid sequence:

| Met | Asn | Cys | Ser | Asn | Met | Ile | Asp | Glu | Ile | Ile | Thr | |
|---|---|---|---|---|---|---|---|---|---|---|---|---|
| His | Leu | Lys | Gln | Pro | Pro | Leu | Pro | Leu | Leu | Asp | Phe | Asn |
| Asn | Leu | Asn | Gly | Glu | Asp | Gln | Asp | Ile | Leu | Met | Glu | Asn |
| Asn | Leu | Arg | Arg | Pro | Asn | Leu | Glu | Ala | Phe | Asn | Arg | Ala |
| Val | Lys | Ser | Leu | Gln | Asn | Ala | Ser | Ala | Ile | Glu | Ser | Ile |
| Leu | Lys | Asn | Leu | Leu | Pro | Cys | Leu | Pro | Leu | Ala | [SEQ ID NO:23] | |

EXAMPLE 13

Construction of pMON5941 which encodes [Met-(15–125)hIL-3 Ala[101]]

The plasmid DNA of pMON5917 was cleaved with NheI and HindIII and ligated to two annealed pairs of oligonucleotides which encode amino acids 86–106 and 107–125 of hIL-3 (See Example 17). The sequences of these oligonucleotides is shown below.

```
5'-CTAGCCACGGCCGCACCCACGCGACATCCAATCCATATCAAGGCTG-
3'-GGTGCCGGCGTGGGTGCGCTGTAGGTTAGGTATAGTTCCGAC-
GTGACTGGAATG-3' [SEQ ID NO:24]
CACTGACCTTACTTAA-5' [SEQ ID NO:25]
EcoRI to HindIII
5'-AATTCCGTCGTAAACTGACCTTCTATCTGAAAACCTTGGAGAACGCGCA-
3'-GGCAGCATTTGACTGGAAGATAGACTTTTGGAACCTCTTGCGCGT-
GGCTCAACAGTAATA-3' [SEQ ID NO:15]
CCGAGTTGTCATTATTCGA-5' [SEQ ID NO:16]
```

The ligation mixture was used to transform competent *E. coli* JM101 cells to ampicillin resistance. Plasmid DNA was isolated from cultures of these transformed cells and the size of the inserted fragment was determined to be larger by restriction analysis with NcoI and HindIII. The Asp to Ala 101 change is encoded on the NheI to EcoRI fragment. The nucleotide sequence of the portion of the coding region between the NheI and HindIII sites was determined and found to be that of the synthetic oligonucleotides. The new plasmid was designated pMON5941. Cells containing the plasmid were induced with nalidixic acid for protein production and sonicated cell pellets and supernatants were submitted for purification and bio-assay.

The plasmid, pMON5941, encodes Met-(15–125)hIL-3($Ala^{101}$) and contains a new NheI restriction site.

EXAMPLE 14

Construction of pMON5960

Plasmid pMON5941 was digested with the restriction enzymes NheI and EcoRI. This vector fragment contains the beta-lactamase gene (AMP), pBR327 origin of replication, the precA promoter, most of the hIL-3 gene and the phage f1 origin of replication as the transcription terminator. The mouse IL-3 amino acids to be substituted into the human sequence were encoded on a synthetic DNA fragment with NheI and EcoRI cloning ends that coded for aa 87–106. The sequences of the two oligonucleotides are shown in Table 2 as Oligo #3 and Oligo #4. These oligonucleotides substitute mouse IL-3 amino acids Ser Ala Leu Pro [SEQ ID NO:105] between amino acids 92–95 of the human IL-3 sequence.

The two strands of synthetic DNA were annealed and approximately 0.5 pmoles was ligated with T-4 ligase to 0.5 micrograms of the vector digest. The resulting DNA was used to transform *E. coli* K12 strain JM101 to ampicillin resistance. The transformed bacteria were selected on ampicillin-containing plates. Plasmid DNA was isolated from cultures of these transformed cells and DNA sequenced to identify the correct clone. There was no definitive restriction screen. A plasmid containing the desired sequence was designated pMON5960.

EXAMPLE 15

Construction of pMON6458

Plasmid pMON6525 was digested with restriction enzymes HindIII and SalI and the resulting 3172 base pair fragment was isolated from a 1% agarose gel by interception onto DEAE membrane. The genetic elements derived from pMON6525 are the beta-lactamase gene (AMP), pBR327 origin of replication, and phage f1 origin of replication as the transcription terminator. Plasmid pMON6457 was digested with restriction enzymes HindIII and SalI and the resulting 1117 base pair fragment was isolated by PAGE and crush and soak elution. The genetic elements derived from pMON6457 are the pAraBAD promoter, g10L ribosome binding site, lamb secretion leader and the (15–125) hIL-3 gene. The eluted restriction fragments were concentrated and desalted using Centricon 30 concentrators. The restriction fragments were ligated with T4 ligase and the resulting DNA was used to transform *E. coli* K-12 strain JM101 to ampicillin resistance. Transformant bacteria were selected on ampicillin-containing plates. Plasmid DNA was isolated from cultures of these transformed cells and the size of the inserted fragment was determined by restriction analysis employing restriction enzymes NcoI and HindIII in double digest. Clones containing the hIL-3 gene (encoding amino acids 15–125) contained a 345 base pair NcoI, HindIII restriction fragment. This construct was designated pMON6458. This plasmid was constructed to eliminate an EcoRI restriction site outside the hIL-3 gene coding region.

EXAMPLE 16

Construction of pMON5980

Plasmid pMON5978 was digested with the restriction enzymes NcoI and EcoRV. This vector fragment contains the beta-lactamase gene (AMP), pBR327 origin of replication, the precA promoter, most of the hIL-3 gene and the phage f1 origin of replication as the transcription terminator. Four synthetic DNA fragments were assembled and inserted into the vector to code for aa Met Ala and residues 15–46 of the IL-3 sequence.

The sequences of these four oligonucleotides are shown in Table 2 as Oligo #27, Oligo #28, Oligo #29 and Oligo #30. The mouse IL-3 amino acids encoded by this fragment are located between aa 18 and 28. The mouse residues are as follows: Ser 18, Ile 19, Val 20, Lys 21, Gly 25, Lys 26, and Pro 28. The four strands of synthetic DNA were annealed and approximately 0.5 pmoles were ligated with T-4 ligase to 0.5 micrograms of the vector digest. The resulting DNA was used to transform *E. coli* K12 strain JM101 to ampicillin resistance. The transformed bacteria were selected on ampicillin-containing plates. Plasmid DNA was isolated from cultures of these transformed cells and restricted with HphI to show that clones containing the synthetic fragment had a new HphI site. A plasmid that contained the correct restriction profile was designated pMON5980. The sequence of the synthetic DNA fragment was verified by DNA sequencing.

EXAMPLE 17

Construction of pMON5961

Plasmid pMON5941 was digested with the restriction enzymes NheI and EcoRI. This vector fragment contains the beta-lactamase gene (AMP), pBR327 origin of replication, the precA promoter, most of the hIL-3 gene and the phage f1 origin of replication as the transcription terminator. The mouse IL-3 amino acids to be substituted into the human IL-3 sequence were encoded on a synthetic DNA fragment with NheI and EcoRI cloning ends that coded for aa 87–106. The sequences of the two oligonucleotides are shown in Table 2 as Oligo #5 and Oligo #6.

These oligonucleotides substitute mouse IL-3 amino acids Gly 92, Val 93, Phe 94, and Arg 96 between amino acids 96–100 of the human IL-3 sequence.

The two strands of synthetic DNA were annealed and approximately 0.5 pmoles was ligated with T-4 ligase to 0.5 micrograms of the vector digest. The resulting DNA was used to transform *E. coli* K12 strain JM101 to ampicillin resistance. Transformed bacteria were selected on ampicillin-containing plates. Plasmid DNA was isolated from cultures of these transformed cells and restricted with XbaI and MluI. The synthetic oligonucleotide encodes a new MluI site that is not present in the parental construct. A plasmid containing the new site was designated pMON5961. The sequence of the synthetic DNA fragment was verified by DNA sequencing.

EXAMPLE 18

Construction of pMON5962

Plasmid pMON5941 was digested with the restriction enzyme NheI then treated with Mung Bean Nuclease according to manufacturer's directions (New England Biolabs) to remove single-stranded DNA resulting in ligatable blunt-ends. The vector was then digested with EcoRI. This vector fragment contains the beta-lactamase gene (AMP), pBR327 origin of replication, the precA promoter, most of the hIL-3 gene and the phage f1 origin of replication as the transcription terminator. The mouse IL-3 amino acids to be substituted into the human IL-3 sequence were encoded on a synthetic DNA fragment with blunted NheI ends and sticky EcoRI ends and code for aa 87–106. The sequences of the two oligonucleotides are shown in Table 2 as Oligo #11 and Oligo #12.

These oligonucleotides substitute mouse IL-3 amino acids Thr 83, Ser 84, Ala 85, Asn 86, and Asp 87 between amino acids 87–91 of the human IL-3 sequence.

The two strands of synthetic DNA were annealed and approximately 0.5 pmoles was ligated with T-4 ligase to 0.5 micrograms of the vector digest. The resulting DNA was used to transform *E. Coli* K12 strain JM101 to ampicillin resistance. The transformed bacteria were selected on ampicillin-containing plates. Plasmid DNA was isolated from cultures of these transformed cells and restricted with XbaI and MluI. The synthetic oligonucleotide encoded a new MluI site that was not present in the parental construct. A plasmid containing the new site was designated pMON5962. The sequence of the synthetic DNA fragment was verified by DNA sequencing.

EXAMPLE 19

Construction of pMON5963

Plasmid pMON5941 was digested with the restriction enzymes NsiI and NheI. This vector fragment contains the beta-lactamase gene (AMP), pBR327 origin of replication, the precA promoter, most of the hIL-3 gene and the phage f1 origin of replication as the transcription terminator. The mouse IL-3 amino acids to be substituted into the human IL-3 sequence were encoded on a synthetic DNA fragment with NsiI and NheI cloning ends that coded for aa 70–87. The sequences of the two oligonucleotides are shown in Table 2 as Oligo #9 and Oligo #10.

These oligonucleotides substitute mouse IL-3 amino acids Lys 75, Asn 77, Gln 79, Lys 80, Asn 82, and Ser 83 between amino acids 75 and 83 of the human IL-3 sequence.

The two strands of synthetic DNA were annealed and approximately 0.5 pmoles was ligated with T-4 ligase to 0.5 micrograms of the vector digest. The resulting DNA was used to transform *E. coli* K12 strain JM101 to ampicillin resistance. The transformed bacteria was selected on ampicillin-containing plates. Plasmid DNA was isolated from cultures of these transformed cells and restricted with XbaI and PstI. The synthetic oligonucleotide encodes a new PstI site that is not present in the parental construct. A plasmid containing the new site was designated pMON5963. The sequence of the synthetic DNA fragment was verified by DNA sequencing. This gene codes for alanine at aa 101.

EXAMPLE 20

Construction of pMON5968

Plasmid pMON5941 was digested with the restriction enzymes NheI and EcoRI. This vector fragment contains the beta-lactamase gene (AMP), pBR327 origin of replication, the precA promoter, most of the hIL-3 gene and the phage f1 origin of replication as the transcription terminator. The mouse amino acids to be substituted into the human sequence were encoded on a synthetic DNA fragment with NheI and EcoRI cloning ends that coded for aa 87–106. The sequences of the two oligonucleotides are shown in Table 2 as Oligo #7 and Oligo #8.

These oligonucleotides substitute mouse amino acid Leu at position 102 and delete amino acids 104 Trp and 105 Asn between amino acids 101 and 105 of the human sequence.

The two strands of synthetic DNA were annealed and approximately 0.5 pmoles was ligated with T-4 ligase to 0.5 micrograms of the vector digest. The resulting DNA was used to transform *E. coli* K12 strain JM101 to ampicillin resistance. The transformed bacteria was selected on ampicillin-containing plates. Plasmid DNA was isolated from cultures of these transformed cells and restricted with XbaI and MluI. The synthetic oligonucleotide encodes a new MluI site that is not present in the parental construct. A plasmid containing the new site was designated pMON5968. The sequence of the synthetic DNA fragment was verified by DNA sequencing.

EXAMPLE 21

Construction of pMON5970

Plasmid pMON5969 was digested with the restriction enzymes EcoRV and XhoI. This vector fragment contains the beta-lactamase gene (AMP), pBR327 origin of replication, the precA promoter, most of the hIL-3 gene and the phage f1 origin of replication as the transcription terminator. The mouse IL-3 amino acids to be substituted into the human sequence were encoded on a synthetic DNA fragment with a blunted 5' end that does not code for a restriction enzyme site and a XhoI cloning site at the 3' end. This fragment coded for aa 47–58 of the IL-3 sequence.

The sequences of the two oligonucleotides are shown in Table 2 as Oligo #13 and Oligo #14.

These oligonucleotides substitute mouse amino acids Ser Leu Arg Asn Lys Ser [SEQ ID NO:110] between amino acids 47 and 52 of the human IL-3 sequence.

The two strands of synthetic DNA were annealed and approximately 0.5 pmoles were ligated with T-4 ligase to 0.5 micrograms of the vector digest. The resulting DNA was used to transform *E. coli* K12 strain JM101 to ampicillin resistance. The transformed bacteria were selected on ampicillin-containing plates. Plasmid DNA was isolated from cultures of these transformed cells and restricted with XbaI and EcoRV to show the loss of the EcoRV site and with XbaI and XhoI to show that the XhoI cloning site was still present. A plasmid that lost the EcoRV site while maintaining the XhoI site was designated pMON5970. The sequence of the synthetic DNA fragment was verified by DNA sequencing.

EXAMPLE 22

Construction of pMON5972

Plasmid pMON5969 was digested with the restriction enzymes EcoRV and NsiI. This vector fragment contains the beta-lactamase gene (AMP), pBR327 origin of replication, the precA promoter, most of the hIL-3 gene and the phage f1 origin of replication as the transcription terminator. The mouse IL-3 amino acids to be substituted into the human IL-3 sequence were encoded on a synthetic DNA fragment with EcoRV and NsiI cloning ends that coded for aa 46–70. The sequences of the two oligonucleotides are shown in Table 2 as Oligo #15 and Oligo #16. These oligonucleotides substitute mouse IL-3 amino acids Phe 53, Val 56, Ser 59, Lys 60, Val 62, and Glu 63 between amino acids 53 and 63 of the human IL-3 sequence.

The two strands of synthetic DNA were annealed and approximately 0.5 pmoles were ligated with T-4 ligase to 0.5 micrograms of the vector digest. The resulting DNA was used to transform E. Coli K12 strain JM101 to ampicillin resistance. The transformed bacteria were selected on ampicillin-containing plates. Plasmid DNA was isolated from cultures of these transformed cells and restricted with XbaI and XhoI to show the loss of the XhoI site and with XbaI and HpaI to show that this new site encoded by the synthetic DNA fragment was present. A plasmid that lost the XhoI site while obtaining the HpaI site was designated pMON5972. The sequence of the synthetic DNA fragment was verified by DNA sequencing.

EXAMPLE 23

Construction of pMON5973

Plasmid pMON5969 was digested with the restriction enzymes XhoI and NsiI. This vector fragment contains the beta-lactamase gene (AMP), pBR327 origin of replication, the precA promoter, most of the hIL-3 gene and the phage f1 origin of replication as the transcription terminator. The mouse IL-3 amino acids to be substituted into the human IL-3 sequence were encoded on a synthetic DNA fragment with XhoI and NsiI cloning ends. This fragment coded for aa 58–70 of the IL-3 sequence. The sequences of the two oligonucleotides are shown in Table 2 as Oligo #17 and Oligo #18. These oligonucleotides substitute mouse IL-3 amino acids Ser Gln Gly Glu Val Asp [SEQ ID NO:112] between amino acids 64 and 69 of the human IL-3 sequence.

The two strands of synthetic DNA were annealed and approximately 0.5 pmoles were ligated with T-4 ligase to 0.5 micrograms of the vector digest. The resulting DNA was used to transform E. coli K12 strain JM101 to ampicillin resistance. The transformed bacteria were selected on ampicillin-containing plates. Plasmid DNA was isolated from cultures of the transformed cells and restricted with HincII. A plasmid with a new HincII site encoded by the synthetic DNA fragment was designated pMON5973. The sequence of the synthetic DNA fragment was verified by DNA sequencing.

EXAMPLE 24

Construction of pMON5974

Plasmid pMON5969 dam-DNA was digested with the restriction enzymes ClaI and EcoRV. This vector fragment contains the beta-lactamase gene (AMP), pBR327 origin of replication, the precA promoter, most of the hIL-3 gene and the phage f1 origin of replication as the transcription terminator. The synthetic DNA fragment to be inserted coded for aa 20–46 of the IL-3 sequence and deleted aa 29–35. The sequences of the two oligonucleotides are shown in Table 2 as Oligo #19 and Oligo #20. These oligonucleotides delete amino acids 29 through 35 (Gln Pro Pro Leu Pro Leu Leu [SEQ ID NO:113]) of the human IL-3 sequence.

The two strands of synthetic DNA were annealed and approximately 0.5 pmoles were ligated with T-4 ligase to 0.5 micrograms of the vector digest. The resulting DNA was used to transform E. coli K12 strain JM101 to ampicillin resistance. The transformed bacteria were selected on ampicillin-containing plates. Plasmid DNA was isolated from cultures of the transformed cells and restricted with XbaI and EcoRV to show that clones containing the synthetic fragment were 21 base pairs smaller than the parental fragment. A plasmid that contained the correct size fragment was designated pMON5974. The sequence of the synthetic DNA fragment was verified by DNA sequencing.

EXAMPLE 25

Construction of pMON5975

Plasmid pMON5969 dam-DNA was digested with the restriction enzymes ClaI and EcoRV. This vector fragment contains the beta-lactamase gene (AMP), pBR327 origin of replication, the precA promoter, most of the hIL-3 gene and the phage f1 origin of replication as the transcription terminator. Four synthetic DNA fragments were assembled and inserted into the vector to code for aa 20–46 of the IL-3 sequence. The sequences of these four oligonucleotides are shown in Table 2 as Oligo #21, Oligo #22, Oligo #23 and Oligo #24. Oligos #23 and #24 were used to make two hybrid genes, pMON5975 and pMON5977. The mouse IL-3 amino acids encoded on this fragment lie between aa 41 and 46 are as follows: Thr Asp Asp Glu Gly Pro [SEQ ID NO:114].

The four strands of synthetic DNA were annealed and approximately 0.5 pmoles were ligated with T-4 ligase to 0.5 micrograms of the vector digest. The resulting DNA was used to transform E. coli K12 strain JM101 to ampicillin reistance. The transformed bacteria were selected on ampicillin-containing plates. Plasmid DNA was isolated from cultures of these transformed cells and restricted with XbaI and AvaII to show that clones containing the synthetic fragment had a new AvaII site. These clones had also lost the EcoRV site. A plasmid that contained the correct restriction profile was designated pMON5975. The sequence of the synthetic DNA fragment was verified by DNA sequencing.

EXAMPLE 26

Construction of pMON5977

Plasmid pMON5969 dam-DNA was digested with the restriction enzymes ClaI and EcoRV. This vector fragment contains the beta-lactamase gene (AMP), pBR327 origin of replication, the precA promoter, most of the hIL-3 gene and the phage f1 origin of replication as the transcription terminator. Four synthetic DNA fragments were assembled and inserted into the vector to code for aa 20–46 of the IL-3 sequence. The sequence of these four oligonucleotides is listed as oligos #23, #24, #25 and #26. Oligo #23 and Oligo #24 were used in making two hybrid genes pMON5975 and pMON5977. The mouse IL-3 amino acids encoded on this fragment are located between aa 36 and 40. The amino acid substitutions are as follows: Glu Pro Glu Leu Lys [SEQ ID NO:115].

The four strands of synthetic DNA were annealed and approximately 0.5 pmoles were ligated with T-4 ligase to 0.5 micrograms of the vector digest. The resulting DNA was used to transform *E. coli* K12 strain JM101 to ampicillin resistance. The transformed bacteria was selected on ampicillin-containing plates. Plasmid DNA was isolated from cultures of these transformed cells and restricted with HpaII to show that clones containing the synthetic fragment had a new HpaII site. A plasmid that contained the correct restriction profile was designated pMON5977. The sequence of the synthetic DNA fragment was verified by DNA sequencing.

EXAMPLE 27

Construction of pMON5979

Plasmid pMON5976 was digested with the restriction enzymes PstI and NheI. This vector fragment contains the beta-lactamase gene (AMP), pBR327 origin of replication, the precA promoter most of the hIL-3 gene and the phage f1 origin of replication as the transcription terminator. The mouse amino acids to be substituted into the human sequence were encoded on a synthetic DNA fragment with PstI and NheI cloning ends. This fragment coded for aa 69–88. The sequence of the two oligonucleotides is shown in Table 2 as Oligo #1 and Oligo #2. These oligonucleotides substitute mouse IL-3 amino acids Pro 64, Glu 65, Asp 66, Arg 67, Tyr 68, and Val 69 between amino acids 70–74 of the human IL-3 sequence.

The two strands of synthetic DNA were annealed and approximately 0.5 pmoles was ligated with T-4 ligase to 0.5 micrograms of the vector digest. The resulting DNA was used to transform *E. coli* K12 strain JM101 to ampicillin resistance. The transformed bacteria was selected on ampicillin-containing plates. Plasmid DNA was isolated from cultures of these transformed cells and screened for the presence of a new Hpa II restriction site. A plasmid containing the new site was designated pMON5979 and sequenced to verify the identity of the synthetic oligonucleotide. This gene codes for alanine at aa.101.

References

Bachmann, B., Pedigrees of some mutant strains of Escherichia coli K-12, *Bacteriological Reviews*, 36:525–557 (1972).

Bayne, M. L. et al. Expression of a synthetic gene encoding human insulin-like growth factor I in cultured mouse fibroblasts. *Proc. Natl. Acad. Sci. USA* 84, 2638–642 (1987).

Ben-Bassat, A., et al. Processing of the initiating methionine from proteins: properties of the Escherichia coli methionine aminopeptidase and its gene structure. *J. Bacteriol.*, 169:751–757 (1987).

Birnboim, H. C. and J. Doly. A rapid alkaline extraction method for screening recombinant plasmid DNA. *Nucleic Acids Research*, 7(6): 1513–1523 (Nov. 24, 1979).

Bradford, M. M., A rapid and sensitive method for the quantitation of microgram quantities of protein utilizing the principle of protein-dye binding, *Analytical Biochemistry*, 72:248–254 (1976).

Clark-Lewis, I., L. E. Hood and S. B. H. Kent. Role of disulfide bridges in determining the biological activity of interleukin 3, *Proc. Natl. Acad. Sci.*, 85:7897–7901 (1988).

Clement, J. M. and Hofnung, M. Gene sequence of the receptor, an outer membrane protein of *E. coli* K12. *Cell*, 27: 507–514 (1981).

Covarrubias, L., et al. Construction and characterization of new cloning vehicles. V. Mobilization and coding properties of pBR322 and several deletion derivatives including pBR327 and pBR328. *Gene* 13: 25–35 (1981).

Dente, L., G. Cesareni and R. Cortese, pEMBL: a new family of single stranded plasmids, *Nucleic Acids Research*, 11:1645–1655 (1983).

Dunn, J. J. and Studier, F. W. Complete nucleotide sequence of bacteriophage T7 DNA and the locations of T7 genetic elements. *J. Mol. Biol.*, 166: 477–553 (1983).

Falk, S., et al. *Hematopathology* 95: 355 (1991).

Ganser, A., et al. *Blood* 76:666 (1990).

Gething and Sambrook, *Nature*, 293: 620–625 (1981).

Gierasch, L. M., *Biochemistry* 28: 923 (1989).

Gillio, A. P., et al. *J. Clin. Invest.* 85: 1560 (1990).

Gouy, M. and G. Gautier, Codon usage in bacteria: Correlation with gene expressivity, *Nucleic Acids Research*, 10: 7055–7074 (1982).

Greenfield, L., T. Boone, and G. Wilcox. DNA sequence of the araBAD promoter in Escherichia coli B/r. *Proc. Natl. Acad. Sci. USA*, 75: 4724–4728 (1978).

Hunkapiller, M. W., et al. High sensitivity sequencing with a gas-phase sequenator. Methods in Enzymology 153: 99–413 (1983).

Kaufman, et al., *Mol. Cell. Biol.*, 5(7): 1750–1759 (1985).

Kaufman, R. J. High level production of proteins in mammalian cells, in *Genetic Engineering, Principles and Methods*, Vol. 9, J. K. Setlow, editor, Plenum Press, New York (1987).

Kunkel, T. A. Rapid and efficient site-specific mutagenesis without phenotypic selection. *Proc. Natl. Acad. Sci. USA*, 82: 488–492 (1985).

Laemmli, U. K., Cleavage of structural proteins during assembly of the head of bacteriophage T4, *Nature*, 227: 680–685 (1970).

Lange, B., M. et al. Growth factor requirements of childhood acute leukemia: establishment of GM-CSF-dependent cell lines. *Blood* 70: 192 (1987).

Mahler, H. R. and E. H. Cordes, in *Biological Chemistry*, p. 128, New York, Harper and Row (1966).

Maniatis, T., E. F. Fritsch and J. Sambrook, *Molecular Cloning, A Laboratory Manual*. Cold Spring Harbor Laboratory (1982).

Marinus, M. G. Location of DNA methylation genes on the Escherichia coli K-12 genetic map. *Molec. Gen. Genet.* 127: 47–55 (1973).

Matsudaira, P. Sequence from picomole quantities of protein electroblotted onto PVDF membranes. *J. Biol. Chem.*, 261: 10035–10038 (1987).

Messing, J., A multipurpose cloning system based on the single-stranded DNA bacteriophage M13. *Recombinant DNA Technical Bulletin*, NIH Publication No. 79-99, Vol. 2, No. 2, 1979, pp. 43–48.

Neu, H. C. and L. A. Heppel. The release of enzymes from Escherichia coli by osmotic shock and during the formation of spheroplasts. *J. Biol. Chem.*, 240: 3685–692 (1965).

Olins, P. O., et al. The T7 phage gene 10 leader RNA, a ribosome-binding site that dramatically enhances the expression of foreign genes in *Escherichia Coli*, *Gene*, 73: 227–235 (1988).

Olins, P. O. and S. H. Rangwala, Vector for enhanced translation of foreign genes in *Escherichia coli*, *Methods in Enzymology*, 185: 115–119 (1990).

Prober, J. M., et al. A system for rapid DNA sequencing with fluorescent chain-terminating dideoxynucleotides. *Science* 238: 336–341 (1987).

Renart J., J. Reiser and G. R. Stark, Transfer of proteins from gels to diazobenzyloxymethyl-paper and detection with anti-sera: a method for studying antibody specificity and antigen structure, *Proc. Natl. Acad. Sci. USA*, 76: 3116–3120 (1979).

Reznikoff, W. and Abelson, J. N. (1980) The Operon. Miller, J. and Reznikoff, W. S. eds., Cold Spring Harbor Laboratory.

Sambrook, J., et al., *Molecular Cloning, A Laboratory Manual*, 2nd edition, Cold Spring Harbor Laboratory 1989).

Sancar, A., et al. Sequences of the recA gene and protein, *Proc. Natl. Acad. Sci.*, 77: 2611–2615 (1980). Sanger, F., S. Nicklen and A. R. Coulson. DNA sequencing with chain-terminating inhibitors. *Proc. Natl. Acad. Sci. U. S. A.* 74: 5463–5467 (1977).

Santoli, D., et al. (1987). Synergistic and antagonistic effects of recombinant human interleukin (IL-3), IL-1, granulocyte and macrophage colony-stimulating factors (G-CSF and M-CSF) on the growth of GM-CSF-dependent leukemic cell lines. *J. Immunol.* 139:348.

Soberon, X., L. Covarrubias and F. Bolivar, Construction and characterization of new cloning vehicles. IV. Deletion derivatives of pBR322 and pBR325, *Gene*, 9: 211–223 (1980).

Stader, J. A. and T. J. Silhavy. Engineering Escherichia coli to secrete heterologous gene products, *Methods in Enzymology*, 185: 166–87 (1990).

Stormo, G., Translation initiation. In: Reznikoff W. and L. Gold (Eds.) *Maximizing Gene Expression*. Butterworth, Boston, Mass., 1986, pp. 195–224.

Summers, M. D. and G. E. Smith. A manual of methods for Baculovirus vectors and insect cell culture procedures. Texas Agricultural Experiment Station Bulletin No. 1555 (1987).

Valtieri, M., et al. (1987). Establishment and characterization of an undifferentiated human T leukemia cell line which requires granulocyte-macrophage colony stimulating factor for growth. *J. Immunol.*, 138: 4042.

Voet, D., et al. Absorption spectra of the common bases. *Biopolymers* 1: 193 (1963).

Wong, E. Y. Y., et al. Expression of secreted IGF-1 in *Escherichia coli. Gene*, 68:193–203 (1988).

Yanisch-Perron, C., J. Viera and J. Messing. Improved M13 phage cloning vectors and host strains: nucleotide sequences of the M13mp18 and pUC19 vectors. Gene 33: 103–119 (1985).

---

SEQUENCE LISTING ( 1 ) GENERAL INFORMATION:

( i i i ) NUMBER OF SEQUENCES: 121

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:1:

CTAGCGATCT TTTAATAAGC TTG         23

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

GATCCAAGCT TATTAAAAGA TCG         23

( 2 ) INFORMATION FOR SEQ ID NO:3:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:3:

GGCAACAATT TCTACAAAAC ACTTGATACT GTATGAGCAT ACAGTATAAT TGCTTCAACA    60

GAACA    65

( 2 ) INFORMATION FOR SEQ ID NO:4:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:4:

GATCTGTTCT GTTGAAGCAA TTATACTGTA TGCTCATACA GTATCAAGTG TTTTGTAGAA    60

ATTGTTGCCG C    71

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:5:

CCATTGCTGC CGGCATCGTG GTC    23

( 2 ) INFORMATION FOR SEQ ID NO:6:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:6:

CATGGCTCCA ATGACTCAGA CTACTTCTCT TAAGACTTCT TGGGTT    46

( 2 ) INFORMATION FOR SEQ ID NO:7:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:7:

AACCCAAGAA GTCTTAAGAG AAGTAGTCTG AGTCATTGGA GC    42

( 2 ) INFORMATION FOR SEQ ID NO:8:

( i ) SEQUENCE CHARACTERISTICS:
        ( A ) LENGTH: 29 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:8:

AAGGAGATAT ATCCATGAAC TGCTCTAAC                                              29

( 2 ) INFORMATION FOR SEQ ID NO:9:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

Met Asn Cys Ser Asn
1               5

( 2 ) INFORMATION FOR SEQ ID NO:10:

( i ) SEQUENCE CHARACTERISTICS:
        ( A ) LENGTH: 120 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

Met Asn Cys Ser Asn Met Ile Asp Glu Ile Ile Thr His Leu Lys Gln
1               5                   10                  15

Pro Pro Leu Pro Leu Leu Asp Phe Asn Asn Leu Asn Gly Glu Asp Gln
                20              25                  30

Asp Ile Leu Met Glu Asn Asn Leu Arg Arg Pro Asn Leu Glu Ala Phe
            35              40                  45

Asn Arg Ala Val Lys Ser Leu Gln Asn Ala Ser Ala Ile Glu Ser Ile
        50              55                  60

Leu Lys Asn Leu Leu Pro Cys Leu Pro Leu Ala Thr Ala Ala Pro Thr
65              70              75                          80

Arg His Pro Ile His Ile Lys Asp Gly Asp Trp Asn Glu Phe Arg Arg
                85              90                      95

Lys Leu Thr Phe Tyr Leu Lys Thr Leu Glu Asn Ala Gln Ala Gln Gln
            100             105                 110

Thr Thr Leu Arg Leu Ala Ile Phe
        115             120

( 2 ) INFORMATION FOR SEQ ID NO:11:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:11:

AATTCCGTCG TAAACTGACC TTCTATCTGA AAACCTTGGA GAACGCGCAG GCTCAACAGA       60

CCACTCTGTC G                                                           71

( 2 ) INFORMATION FOR SEQ ID NO:12:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:12:

CTAGCGACAG AGTGGTCTGT TGAGCCTGCG CGTTCTCCAA GGTTTTCAGA TAGAAGGTCA 60

GTTTACGACG G 71

( 2 ) INFORMATION FOR SEQ ID NO:13:

( i ) SEQUENCE CHARACTERISTICS:
        ( A ) LENGTH: 134 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

```
Met Ala Pro Met Thr Gln Thr Thr Ser Leu Lys Thr Ser Trp Val Asn
 1               5                  10                   15

Cys Ser Asn Met Ile Asp Glu Ile Ile Thr His Leu Lys Gln Pro Pro
            20                  25                  30

Leu Pro Leu Leu Asp Phe Asn Asn Leu Asn Gly Glu Asp Gln Asp Ile
         35                  40                  45

Leu Met Glu Asn Asn Leu Arg Arg Pro Asn Leu Glu Ala Phe Asn Arg
     50                  55                  60

Ala Val Lys Ser Leu Gln Asn Ala Ser Ala Ile Glu Ser Ile Leu Lys
 65                  70                  75                   80

Asn Leu Leu Pro Cys Leu Pro Leu Ala Thr Ala Ala Pro Thr Arg His
                 85                  90                  95

Pro Ile His Ile Lys Asp Gly Asp Trp Asn Glu Phe Arg Arg Lys Leu
             100                 105                 110

Thr Phe Tyr Leu Lys Thr Leu Glu Asn Ala Gln Ala Gln Gln Thr Thr
         115                 120                 125

Leu Ser Leu Ala Ile Phe
         130
```

( 2 ) INFORMATION FOR SEQ ID NO:14:

( i ) SEQUENCE CHARACTERISTICS:
        ( A ) LENGTH: 120 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

```
Met Asn Cys Ser Asn Met Ile Asp Glu Ile Ile Thr His Leu Lys Gln
 1               5                  10                   15

Pro Pro Leu Pro Leu Leu Asp Phe Asn Asn Leu Asn Gly Glu Asp Gln
            20                  25                  30

Asp Ile Leu Met Glu Asn Asn Leu Arg Arg Pro Asn Leu Glu Ala Phe
         35                  40                  45

Asn Arg Ala Val Lys Ser Leu Gln Asn Ala Ser Ala Ile Glu Ser Ile
     50                  55                  60

Leu Lys Asn Leu Leu Pro Cys Leu Pro Leu Ala Thr Ala Ala Pro Thr
 65                  70                  75                   80

Arg His Pro Ile His Ile Lys Asp Gly Asp Trp Asn Glu Phe Arg Arg
                 85                  90                  95

Lys Leu Thr Phe Tyr Leu Lys Thr Leu Glu Asn Ala Gln Ala Gln Gln
             100                 105                 110
```

```
       Thr  Thr  Leu  Ser  Leu  Ala  Ile  Phe
            115                      120
```

( 2 ) INFORMATION FOR SEQ ID NO:15:

( i ) SEQUENCE CHARACTERISTICS:
    ( A ) LENGTH: 64 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:15:

```
AATTCCGTCG  TAAACTGACC  TTCTATCTGA  AAACCTTGGA  GAACGCGCAG  GCTCAACAGT        60

AATA                                                                         64
```

( 2 ) INFORMATION FOR SEQ ID NO:16:

( i ) SEQUENCE CHARACTERISTICS:
    ( A ) LENGTH: 64 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:16:

```
AGCTTATTAC  TGTTGAGCCT  GCGCGTTCTC  CAAGGTTTTC  AGATAGAAGG  TCAGTTTACG        60

ACGG                                                                         64
```

( 2 ) INFORMATION FOR SEQ ID NO:17:

( i ) SEQUENCE CHARACTERISTICS:
    ( A ) LENGTH: 126 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:17:

```
Met  Ala  Pro  Met  Thr  Gln  Thr  Thr  Ser  Leu  Lys  Thr  Ser  Trp  Val  Asn
1              5                        10                       15

Cys  Ser  Asn  Met  Ile  Asp  Glu  Ile  Ile  Thr  His  Leu  Lys  Gln  Pro  Pro
               20                       25                       30

Leu  Pro  Leu  Leu  Asp  Phe  Asn  Asn  Leu  Asn  Gly  Glu  Asp  Gln  Asp  Ile
               35                       40                  45

Leu  Met  Glu  Asn  Asn  Leu  Arg  Arg  Pro  Asn  Leu  Glu  Ala  Phe  Asn  Arg
     50                       55                  60

Ala  Val  Lys  Ser  Leu  Gln  Asn  Ala  Ser  Ala  Ile  Glu  Ser  Ile  Leu  Lys
65                       70                  75                            80

Asn  Leu  Leu  Pro  Cys  Leu  Pro  Leu  Ala  Thr  Ala  Ala  Pro  Thr  Arg  His
                    85                       90                  95

Pro  Ile  His  Ile  Lys  Asp  Gly  Asp  Trp  Asn  Glu  Phe  Arg  Arg  Lys  Leu
               100                      105                      110

Thr  Phe  Tyr  Leu  Lys  Thr  Leu  Glu  Asn  Ala  Gln  Ala  Gln  Gln
               115                      120                 125
```

( 2 ) INFORMATION FOR SEQ ID NO:18:

( i ) SEQUENCE CHARACTERISTICS:
    ( A ) LENGTH: 112 amino acids
    ( B ) TYPE: amino acid
    ( D ) TOPOLOGY: linear (i i) MOLECULE TYPE: peptide (x i) SEQUENCE DESCRIPTION: SEQ ID NO:18:

| Met | Asn | Cys | Ser | Asn | Met | Ile | Asp | Glu | Ile | Ile | Thr | His | Leu | Lys | Gln |
|---|---|---|---|---|---|---|---|---|---|---|---|---|---|---|---|
| 1 | | | | 5 | | | | | 10 | | | | | 15 | |

| Pro | Pro | Leu | Pro | Leu | Leu | Asp | Phe | Asn | Asn | Leu | Asn | Gly | Glu | Asp | Gln |
|---|---|---|---|---|---|---|---|---|---|---|---|---|---|---|---|
| | | | 20 | | | | | 25 | | | | | 30 | | |

| Asp | Ile | Leu | Met | Glu | Asn | Asn | Leu | Arg | Arg | Pro | Asn | Leu | Glu | Ala | Phe |
|---|---|---|---|---|---|---|---|---|---|---|---|---|---|---|---|
| | | | 35 | | | | | 40 | | | | | 45 | | |

| Asn | Arg | Ala | Val | Lys | Ser | Leu | Gln | Asn | Ala | Ser | Ala | Ile | Glu | Ser | Ile |
|---|---|---|---|---|---|---|---|---|---|---|---|---|---|---|---|
| | | 50 | | | | | 55 | | | | | 60 | | | |

| Leu | Lys | Asn | Leu | Leu | Pro | Cys | Leu | Pro | Leu | Ala | Thr | Ala | Ala | Pro | Thr |
|---|---|---|---|---|---|---|---|---|---|---|---|---|---|---|---|
| 65 | | | | | 70 | | | | | 75 | | | | | 80 |

| Arg | His | Pro | Ile | His | Ile | Lys | Asp | Gly | Asp | Trp | Asn | Glu | Phe | Arg | Arg |
|---|---|---|---|---|---|---|---|---|---|---|---|---|---|---|---|
| | | | | 85 | | | | 90 | | | | | | 95 | |

| Lys | Leu | Thr | Phe | Tyr | Leu | Lys | Thr | Leu | Glu | Asn | Ala | Gln | Ala | Gln | Gln |
|---|---|---|---|---|---|---|---|---|---|---|---|---|---|---|---|
| | | | 100 | | | | | 105 | | | | | 110 | | |

(2) INFORMATION FOR SEQ ID NO:19:

(i) SEQUENCE CHARACTERISTICS:
   (A) LENGTH: 112 amino acids
   (B) TYPE: amino acid
   (D) TOPOLOGY: linear (i i) MOLECULE TYPE: peptide (x i) SEQUENCE DESCRIPTION: SEQ ID NO:19:

| Met | Asn | Cys | Ser | Asn | Met | Ile | Asp | Glu | Ile | Ile | Thr | His | Leu | Lys | Gln |
|---|---|---|---|---|---|---|---|---|---|---|---|---|---|---|---|
| 1 | | | | 5 | | | | | 10 | | | | | 15 | |

| Pro | Pro | Leu | Pro | Leu | Leu | Asp | Phe | Asn | Asn | Leu | Asn | Gly | Glu | Asp | Gln |
|---|---|---|---|---|---|---|---|---|---|---|---|---|---|---|---|
| | | | 20 | | | | | 25 | | | | | 30 | | |

| Asp | Ile | Leu | Met | Glu | Asn | Asn | Leu | Arg | Arg | Pro | Asn | Leu | Glu | Ala | Phe |
|---|---|---|---|---|---|---|---|---|---|---|---|---|---|---|---|
| | | | 35 | | | | | 40 | | | | | 45 | | |

| Asn | Arg | Ala | Val | Lys | Ser | Leu | Gln | Asn | Ala | Ser | Ala | Ile | Glu | Ser | Ile |
|---|---|---|---|---|---|---|---|---|---|---|---|---|---|---|---|
| | | 50 | | | | | 55 | | | | | 60 | | | |

| Leu | Lys | Asn | Leu | Leu | Pro | Cys | Leu | Pro | Leu | Ala | Thr | Ala | Ala | Pro | Thr |
|---|---|---|---|---|---|---|---|---|---|---|---|---|---|---|---|
| 65 | | | | | 70 | | | | | 75 | | | | | 80 |

| Arg | His | Pro | Ile | His | Ile | Lys | Ala | Gly | Asp | Trp | Asn | Glu | Phe | Arg | Arg |
|---|---|---|---|---|---|---|---|---|---|---|---|---|---|---|---|
| | | | | 85 | | | | 90 | | | | | | 95 | |

| Lys | Leu | Thr | Phe | Tyr | Leu | Lys | Thr | Leu | Glu | Asn | Ala | Gln | Ala | Gln | Gln |
|---|---|---|---|---|---|---|---|---|---|---|---|---|---|---|---|
| | | | 100 | | | | | 105 | | | | | 110 | | |

(2) INFORMATION FOR SEQ ID NO:20:

(i) SEQUENCE CHARACTERISTICS:
   (A) LENGTH: 113 amino acids
   (B) TYPE: amino acid
   (D) TOPOLOGY: linear (i i) MOLECULE TYPE: peptide (x i) SEQUENCE DESCRIPTION: SEQ ID NO:20:

| Met | Ala | Asn | Cys | Ser | Asn | Met | Ile | Asp | Glu | Ile | Ile | Thr | His | Leu | Lys |
|---|---|---|---|---|---|---|---|---|---|---|---|---|---|---|---|
| 1 | | | | 5 | | | | | 10 | | | | | 15 | |

| Gln | Pro | Pro | Leu | Pro | Leu | Leu | Asp | Phe | Asn | Asn | Leu | Asn | Gly | Glu | Asp |
|---|---|---|---|---|---|---|---|---|---|---|---|---|---|---|---|
| | | | | 20 | | | | | 25 | | | | | 30 | |

| Gln | Asp | Ile | Leu | Met | Glu | Asn | Asn | Leu | Arg | Arg | Pro | Asn | Leu | Glu | Ala |
|---|---|---|---|---|---|---|---|---|---|---|---|---|---|---|---|
| | | | | 35 | | | | | 40 | | | | | 45 | |

|     |     |     |     |     |     |     |     |     |     |     |     |     |     |     |
| --- | --- | --- | --- | --- | --- | --- | --- | --- | --- | --- | --- | --- | --- | --- |
| Phe | Asn | Arg | Ala | Val | Lys | Ser | Leu | Gln | Asn | Ala | Ser | Ala | Ile | Glu | Ser |
|     | 50  |     |     |     |     | 55  |     |     |     | 60  |     |     |     |     |     |
| Ile | Leu | Lys | Asn | Leu | Leu | Pro | Cys | Leu | Pro | Leu | Ala | Thr | Ala | Ala | Pro |
| 65  |     |     |     |     | 70  |     |     |     |     | 75  |     |     |     |     | 80  |
| Thr | Arg | His | Pro | Ile | His | Ile | Lys | Asp | Gly | Asp | Trp | Asn | Glu | Phe | Arg |
|     |     |     |     | 85  |     |     |     |     | 90  |     |     |     |     | 95  |     |
| Arg | Lys | Leu | Thr | Phe | Tyr | Leu | Lys | Thr | Leu | Glu | Asn | Ala | Gln | Ala | Gln |
|     |     |     | 100 |     |     |     |     | 105 |     |     |     |     | 110 |     |     |
| Gln |     |     |     |     |     |     |     |     |     |     |     |     |     |     |     |

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:21:

CATGGCTAAC TGCTCTAACA TGAT 24

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:22:

CGATCATGTT AGAGCAGTTA GC 22

(2) INFORMATION FOR SEQ ID NO:23:

(i) SEQUENCE CHARACTERISTICS:
        (A) LENGTH: 75 amino acids
        (B) TYPE: amino acid
        (D) TOPOLOGY: linear (ii) MOLECULE TYPE: peptide (xi) SEQUENCE DESCRIPTION: SEQ ID NO:23:

|     |     |     |     |     |     |     |     |     |     |     |     |     |     |     |
| --- | --- | --- | --- | --- | --- | --- | --- | --- | --- | --- | --- | --- | --- | --- |
| Met | Asn | Cys | Ser | Asn | Met | Ile | Asp | Glu | Ile | Ile | Thr | His | Leu | Lys | Gln |
| 1   |     |     |     | 5   |     |     |     |     | 10  |     |     |     |     | 15  |     |
| Pro | Pro | Leu | Pro | Leu | Leu | Asp | Phe | Asn | Asn | Leu | Asn | Gly | Glu | Asp | Gln |
|     |     |     | 20  |     |     |     |     | 25  |     |     |     | 30  |     |     |     |
| Asp | Ile | Leu | Met | Glu | Asn | Asn | Leu | Arg | Arg | Pro | Asn | Leu | Glu | Ala | Phe |
|     |     | 35  |     |     |     |     | 40  |     |     |     | 45  |     |     |     |     |
| Asn | Arg | Ala | Val | Lys | Ser | Leu | Gln | Asn | Ala | Ser | Ala | Ile | Glu | Ser | Ile |
|     | 50  |     |     |     |     | 55  |     |     |     | 60  |     |     |     |     |     |
| Leu | Lys | Asn | Leu | Leu | Pro | Cys | Leu | Pro | Leu | Ala |     |     |     |     |     |
| 65  |     |     |     | 70  |     |     |     |     | 75  |     |     |     |     |     |     |

(2) INFORMATION FOR SEQ ID NO:24:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (i i) MOLECULE TYPE: DNA (synthetic)

(x i) SEQUENCE DESCRIPTION: SEQ ID NO:24:

CTAGCCACGG CCGCACCCAC GCGACATCCA ATCCATATCA AGGCTGGTGA CTGGAATG    58

(2) INFORMATION FOR SEQ ID NO:25:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (i i) MOLECULE TYPE: DNA (synthetic)

(x i) SEQUENCE DESCRIPTION: SEQ ID NO:25:

AATTCATTCC AGTCACCAGC CTTGATATGG ATTGGATGTC GCGTGGGTGC GGCCGTGG    58

(2) INFORMATION FOR SEQ ID NO:26:

(i) SEQUENCE CHARACTERISTICS:
        (A) LENGTH: 157 base pairs
        (B) TYPE: nucleic acid
        (C) STRANDEDNESS: double
        (D) TOPOLOGY: linear (i i) MOLECULE TYPE: DNA (genomic)

(i x) FEATURE:
        (A) NAME/KEY: CDS
        (B) LOCATION: 1..156

(x i) SEQUENCE DESCRIPTION: SEQ ID NO:26:

```
ATC GAT GAA ATC ATC ACC CAC CTG AAG CAG CCA CCG CTG CCG CTG CTG    48
Ile Asp Glu Ile Ile Thr His Leu Lys Gln Pro Pro Leu Pro Leu Leu
 1               5                  10                  15

GAC TTC AAC AAC CTC AAT GGT GAA GAC CAA GAT ATC CTG ATG GAA AAT    96
Asp Phe Asn Asn Leu Asn Gly Glu Asp Gln Asp Ile Leu Met Glu Asn
            20                  25                  30

AAC CTT CGT CGT CCA AAC CTC GAG GCA TTC AAC CGT GCT GTC AAG TCT   144
Asn Leu Arg Arg Pro Asn Leu Glu Ala Phe Asn Arg Ala Val Lys Ser
        35                  40                  45

CTG CAG AAT GCA T                                                  157
Leu Gln Asn Ala
     50
```

(2) INFORMATION FOR SEQ ID NO:27:

(i) SEQUENCE CHARACTERISTICS:
        (A) LENGTH: 52 amino acids
        (B) TYPE: amino acid
        (D) TOPOLOGY: linear (i i) MOLECULE TYPE: protein (x i) SEQUENCE DESCRIPTION: SEQ ID NO:27:

```
Ile Asp Glu Ile Ile Thr His Leu Lys Gln Pro Pro Leu Pro Leu Leu
 1               5                  10                  15

Asp Phe Asn Asn Leu Asn Gly Glu Asp Gln Asp Ile Leu Met Glu Asn
            20                  25                  30

Asn Leu Arg Arg Pro Asn Leu Glu Ala Phe Asn Arg Ala Val Lys Ser
        35                  40                  45

Leu Gln Asn Ala
     50
```

(2) INFORMATION FOR SEQ ID NO:28:

5,501,962

( i ) SEQUENCE CHARACTERISTICS:
    ( A ) LENGTH: 58 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:28:

GCCGGAAGAC CGTTACGTTA TCGAATCCAT CCTGAAAAAC CTGCTGCCGT GCCTGCCG        58

( 2 ) INFORMATION FOR SEQ ID NO:29:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:29:

CTAGCGGCAG GCACGGCAGC AGGTTTTTCA GGATGGATTC GATAACGTAA CGGTCTTCCG        60

GCTGCA        66

( 2 ) INFORMATION FOR SEQ ID NO:30:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:30:

CTAGCCACGG CCGCATCCGC TCTGCCGCCA ATCCATATCA AGGACGGTGA CTGGAATG        58

( 2 ) INFORMATION FOR SEQ ID NO:31:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:31:

AATTCATTCC AGTCACCGTC CTTGATATGG ATTGGCGGCA GAGCGGATGC GGCCGTGG        58

( 2 ) INFORMATION FOR SEQ ID NO:32:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:32:

CTAGCCACGG CCGCACCGAC GCGTCATGGT GTTTTCATCC GTGACGGTGA CTGGAATG        58

( 2 ) INFORMATION FOR SEQ ID NO:33:

( i ) SEQUENCE CHARACTERISTICS:
        ( A ) LENGTH: 58 base pairs (B) TYPE: nucleic acid
(C) STRANDEDNESS: single
(D) TOPOLOGY: linear (i i) MOLECULE TYPE: DNA (synthetic)

(x i) SEQUENCE DESCRIPTION: SEQ ID NO:33:

AATTCATTCC AGTCACCGTC ACGGATGAAA ACACCATGAC GCGTCGGTGC GGCCGTGG    58

(2) INFORMATION FOR SEQ ID NO:34:

(i) SEQUENCE CHARACTERISTICS:
(A) LENGTH: 52 base pairs
(B) TYPE: nucleic acid
(C) STRANDEDNESS: single
(D) TOPOLOGY: linear (i i) MOLECULE TYPE: DNA (synthetic)

(x i) SEQUENCE DESCRIPTION: SEQ ID NO:34:

CTAGCCACGG CCGCACCGAC GCGTCATCCA ATCCATATCA AGGACCTGGA CG    52

(2) INFORMATION FOR SEQ ID NO:35:

(i) SEQUENCE CHARACTERISTICS:
(A) LENGTH: 52 base pairs
(B) TYPE: nucleic acid
(C) STRANDEDNESS: single
(D) TOPOLOGY: linear (i i) MOLECULE TYPE: DNA (synthetic)

(x i) SEQUENCE DESCRIPTION: SEQ ID NO:35:

AATTCGTCCA GGTCCTTGAT ATGGATTGGA TGACGCGTCG GTGCGGCCGT GG    52

(2) INFORMATION FOR SEQ ID NO:36:

(i) SEQUENCE CHARACTERISTICS:
(A) LENGTH: 45 base pairs
(B) TYPE: nucleic acid
(C) STRANDEDNESS: single
(D) TOPOLOGY: linear (i i) MOLECULE TYPE: DNA (synthetic)

(x i) SEQUENCE DESCRIPTION: SEQ ID NO:36:

TCAGCAATTA AAAGCAACCT GCAGAAGCTC AACTCCTGTC TGCCG    45

(2) INFORMATION FOR SEQ ID NO:37:

(i) SEQUENCE CHARACTERISTICS:
(A) LENGTH: 53 base pairs
(B) TYPE: nucleic acid
(C) STRANDEDNESS: single
(D) TOPOLOGY: linear (i i) MOLECULE TYPE: DNA (synthetic)

(x i) SEQUENCE DESCRIPTION: SEQ ID NO:37:

CTAGCGGCAG ACAGGAGTTG AGCTTCTGCA GGTTGCTTTT AATTGCTGAT GCA    53

(2) INFORMATION FOR SEQ ID NO:38:

(i) SEQUENCE CHARACTERISTICS:
(A) LENGTH: 58 base pairs
(B) TYPE: nucleic acid
(C) STRANDEDNESS: single
(D) TOPOLOGY: linear (i i) MOLECULE TYPE: DNA (synthetic)

( x i ) SEQUENCE DESCRIPTION: SEQ ID NO:38:

ACCTCCGCTA ACGATCCGAC GCGTCATCCA ATCCATATCA AGGACGGTGA CTGGAACG 58

( 2 ) INFORMATION FOR SEQ ID NO:39:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:39:

AATTCGTTCC AGTCACCGTC CTTGATATGG ATTGGATGAC GCGTCGGATC GTTAGCGGAG 60

GT 62

( 2 ) INFORMATION FOR SEQ ID NO:40:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:40:

TCCCTGCGTA ACAAATCCCT TCGTCGTCCA AACC 34

( 2 ) INFORMATION FOR SEQ ID NO:41:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:41:

TCGAGGTTTG GACGACGAAG GGATTTGTTA CGCAGGGA 38

( 2 ) INFORMATION FOR SEQ ID NO:42:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:42:

ATCCTGATGG AAAATAACTT CCGTCGTGTT AACCTCTCCA AATTCGTTGA AGCTGTCAAG 60

TCTCTGCAGA ATGCA 75

( 2 ) INFORMATION FOR SEQ ID NO:43:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:43:

TTCTGCAGAG ACTTGACAGC TTCAACGAAT TGGAGAGGT TAACACGACG GAAGTTATTT  60

TCCATCAGGA T  71

( 2 ) INFORMATION FOR SEQ ID NO:44:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:44:

TCGAGGCATT CAACCGTTCC CAGGGTGAAG TTGACAATGC A  41

( 2 ) INFORMATION FOR SEQ ID NO:45:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:45:

TTGTCAACTT CACCCTGGGA ACGGTTGAAT GCC  33

( 2 ) INFORMATION FOR SEQ ID NO:46:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:46:

CGATGAAATC ATCACCCACC TGAAGGACTT CAACAACCTC AATGGTGAAG ACCAAGAT  58

( 2 ) INFORMATION FOR SEQ ID NO:47:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:47:

ATCTTGGTCT TCACCATTGA GGTTGTTGAA GTCCTTCAGG TGGGTGATGA TTTCAT  56

( 2 ) INFORMATION FOR SEQ ID NO:48:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:48:

CCGCTGCCGC TGCTGGACTT CAACAACCTC ACCGACGACG AAGGTCCG  48

( 2 ) INFORMATION FOR SEQ ID NO:49:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:49:

CGGACCTTCG TCGTCGGTGA GGTTGTTGAA GTCCAGCAGC     40

( 2 ) INFORMATION FOR SEQ ID NO:50:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:50:

CGATGAAATC ATCACCCACC TGAAGCAGCC A     31

( 2 ) INFORMATION FOR SEQ ID NO:51:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:51:

GGCTGCGGTG GCTGCTTCAG GTGGGTGATG ATTTCAT     37

( 2 ) INFORMATION FOR SEQ ID NO:52:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:52:

CCGCTGCCGC TGCTGGAACC GGAACTGAAA AATGGTGAAG ACCAAGAT     48

( 2 ) INFORMATION FOR SEQ ID NO:53:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:53:

ATCTTGGTCT TCACCATTTT TCAGTTCCGG TTCCAGCAGC     40

( 2 ) INFORMATION FOR SEQ ID NO:54:

( i ) SEQUENCE CHARACTERISTICS:

(A) LENGTH: 55 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:54:

CATGGCTAAC TGCTCTTCCA TCGTTAAAGA AATCATCGGT AAACTGCCGC AGCCA    55

(2) INFORMATION FOR SEQ ID NO:55:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:55:

CGGCAGTTTA CCGATGATTT CTTTAACGAT GGAAGAGCAG TTAGC    45

(2) INFORMATION FOR SEQ ID NO:56:

(i) SEQUENCE CHARACTERISTICS:
(A) LENGTH: 48 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:56:

CCGCTGCCGC TGCTGGACTT CAACAACCTC AATGGTGAAG ACCAAGAT    48

(2) INFORMATION FOR SEQ ID NO:57:

(i) SEQUENCE CHARACTERISTICS:
(A) LENGTH: 54 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:57:

ATCTTGGTCT TCACCATTGA GGTTGTTGAA GTCCAGCAGC GGCAGCGGTG GCTG    54

(2) INFORMATION FOR SEQ ID NO:58:

(i) SEQUENCE CHARACTERISTICS:
(A) LENGTH: 61 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:58:

CGTAGAAATC ATCACCCACC TGAAGCAGCC ACCGCTGCCG CTGCTGGACT TCAACAACCT    60
C    61

(2) INFORMATION FOR SEQ ID NO:59:

(i) SEQUENCE CHARACTERISTICS:
(A) LENGTH: 53 base pairs
(B) TYPE: nucleic acid
(C) STRANDEDNESS: single (D) TOPOLOGY: linear (ii) MOLECULE TYPE: DNA (synthetic)

(xi) SEQUENCE DESCRIPTION: SEQ ID NO:59:

GTTGAAGTCC AGCAGCGGCA GCGGTGGCTG CTTCAGGTGG GTGATGATTT CAT    53

(2) INFORMATION FOR SEQ ID NO:60:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:60:

AATGGTGAAG ACCAAGATAT CCTGATGGAA AATAACCTTC GTCGTCCAAA CC    52

(2) INFORMATION FOR SEQ ID NO:61:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:61:

TCGAGGTTTG GACGACGAAG GTTATTTTCC ATCAGGATAT CTTGGTCTTC ACCATTGAGG    60

TT    62

(2) INFORMATION FOR SEQ ID NO:62:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:62:

TCGAGGCATT CAACCGTGCT GTCAAGTCTC TGCAGAATGC A    41

(2) INFORMATION FOR SEQ ID NO:63:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:63:

TTCTGCAGAG ACTTGACAGC ACGGTTGAAT GCC    33

(2) INFORMATION FOR SEQ ID NO:64:

(i) SEQUENCE CHARACTERISTICS:
        (A) LENGTH: 114 amino acids
        (B) TYPE: amino acid
        (D) TOPOLOGY: linear (ii) MOLECULE TYPE: peptide ( x i ) SEQUENCE DESCRIPTION: SEQ ID NO:64:

| Met | Asn | Cys | Ser | Asn | Met | Ile | Asp | Glu | Ile | Ile | Thr | His | Leu | Lys | Gln |
| 1 | | | | 5 | | | | | 10 | | | | | 15 | |

| Pro | Pro | Leu | Pro | Leu | Leu | Asp | Phe | Asn | Asn | Leu | Asn | Gly | Glu | Asp | Gln |
| | | | 20 | | | | | 25 | | | | | 30 | | |

| Asp | Ile | Leu | Met | Glu | Asn | Asn | Leu | Arg | Arg | Pro | Asn | Leu | Glu | Ala | Phe |
| | | | 35 | | | | 40 | | | | | 45 | | | |

| Asn | Arg | Ala | Val | Lys | Ser | Leu | Gln | Pro | Glu | Asp | Arg | Tyr | Val | Ile | Glu |
| | | 50 | | | | | 55 | | | | | 60 | | | |

| Ser | Ile | Leu | Lys | Asn | Leu | Leu | Pro | Cys | Leu | Pro | Leu | Ala | Thr | Ala | Ala |
| 65 | | | | | 70 | | | | | 75 | | | | | 80 |

| Pro | Thr | Arg | His | Pro | Ile | His | Ile | Lys | Ala | Gly | Asp | Trp | Asn | Glu | Phe |
| | | | | 85 | | | | | 90 | | | | | 95 | |

| Arg | Arg | Lys | Leu | Thr | Phe | Tyr | Leu | Lys | Thr | Leu | Glu | Asn | Ala | Gln | Ala |
| | | | 100 | | | | | 105 | | | | | 110 | | |

| Gln | Gln |

( 2 ) INFORMATION FOR SEQ ID NO:65:

( i ) SEQUENCE CHARACTERISTICS:
( A ) LENGTH: 112 amino acids
( B ) TYPE: amino acid
( D ) TOPOLOGY: linear ( i i ) MOLECULE TYPE: peptide ( x i ) SEQUENCE DESCRIPTION: SEQ ID NO:65:

| Met | Asn | Cys | Ser | Asn | Met | Ile | Asp | Glu | Ile | Ile | Thr | His | Leu | Lys | Gln |
| 1 | | | | 5 | | | | | 10 | | | | | 15 | |

| Pro | Pro | Leu | Pro | Leu | Leu | Asp | Phe | Asn | Asn | Leu | Asn | Gly | Glu | Asp | Gln |
| | | | 20 | | | | | 25 | | | | | 30 | | |

| Asp | Ile | Leu | Met | Glu | Asn | Asn | Leu | Arg | Arg | Pro | Asn | Leu | Glu | Ala | Phe |
| | | | 35 | | | | 40 | | | | | 45 | | | |

| Asn | Arg | Ala | Val | Lys | Ser | Leu | Gln | Asn | Ala | Ser | Ala | Ile | Glu | Ser | Ile |
| | | 50 | | | | | 55 | | | | | 60 | | | |

| Leu | Lys | Asn | Leu | Leu | Pro | Cys | Leu | Pro | Leu | Ala | Thr | Ala | Ala | Ser | Ala |
| 65 | | | | | 70 | | | | | 75 | | | | | 80 |

| Leu | Pro | Pro | Ile | His | Ile | Lys | Asp | Gly | Asp | Trp | Asn | Glu | Phe | Arg | Arg |
| | | | | 85 | | | | | 90 | | | | | 95 | |

| Lys | Leu | Thr | Phe | Tyr | Leu | Lys | Thr | Leu | Glu | Asn | Ala | Gln | Ala | Gln | Gln |
| | | | 100 | | | | | 105 | | | | | 110 | | |

( 2 ) INFORMATION FOR SEQ ID NO:66:

( i ) SEQUENCE CHARACTERISTICS:
( A ) LENGTH: 112 amino acids
( B ) TYPE: amino acid
( D ) TOPOLOGY: linear ( i i ) MOLECULE TYPE: peptide ( x i ) SEQUENCE DESCRIPTION: SEQ ID NO:66:

| Met | Asn | Cys | Ser | Asn | Met | Ile | Asp | Glu | Ile | Ile | Thr | His | Leu | Lys | Gln |
| 1 | | | | 5 | | | | | 10 | | | | | 15 | |

| Pro | Pro | Leu | Pro | Leu | Leu | Asp | Phe | Asn | Asn | Leu | Asn | Gly | Glu | Asp | Gln |
| | | | 20 | | | | | 25 | | | | | 30 | | |

| Asp | Ile | Leu | Met | Glu | Asn | Asn | Leu | Arg | Arg | Pro | Asn | Leu | Glu | Ala | Phe |
| | | | 35 | | | | 40 | | | | | 45 | | | |

| Asn | Arg | Ala | Val | Lys | Ser | Leu | Gln | Asn | Ala | Ser | Ala | Ile | Glu | Ser | Ile |

```
                  50                        55                              60
Leu   Lys   Asn   Leu   Leu   Pro   Cys   Leu   Pro   Leu   Ala   Thr   Ala   Ala   Pro   Thr
65                            70                      75                                  80

Arg   His   Gly   Val   Phe   Ile   Arg   Asp   Gly   Asp   Trp   Asn   Glu   Phe   Arg   Arg
                        85                            90                            95

Lys   Leu   Thr   Phe   Tyr   Leu   Lys   Thr   Leu   Glu   Asn   Ala   Gln   Ala   Gln   Gln
                  100                         105                       110
```

( 2 ) INFORMATION FOR SEQ ID NO:67:

( i ) SEQUENCE CHARACTERISTICS:
        ( A ) LENGTH: 112 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:67:

```
Met   Asn   Cys   Ser   Asn   Met   Ile   Asp   Glu   Ile   Ile   Thr   His   Leu   Lys   Gln
1                       5                             10                            15

Pro   Pro   Leu   Pro   Leu   Leu   Asp   Phe   Asn   Asn   Leu   Asn   Gly   Glu   Asp   Gln
                  20                        25                            30

Asp   Ile   Leu   Met   Glu   Asn   Asn   Leu   Arg   Arg   Pro   Asn   Leu   Glu   Ala   Phe
                  35                        40                            45

Asn   Arg   Ala   Val   Lys   Ser   Leu   Gln   Asn   Ala   Ser   Ala   Ile   Glu   Ser   Ile
      50                            55                            60

Leu   Lys   Asn   Leu   Leu   Pro   Cys   Leu   Pro   Thr   Ser   Ala   Asn   Asp   Pro   Thr
65                            70                      75                                  80

Arg   His   Pro   Ile   His   Ile   Lys   Asp   Gly   Asp   Trp   Asn   Glu   Phe   Arg   Arg
                        85                            90                            95

Lys   Leu   Thr   Phe   Tyr   Leu   Lys   Thr   Leu   Glu   Asn   Ala   Gln   Ala   Gln   Gln
                  100                         105                       110
```

( 2 ) INFORMATION FOR SEQ ID NO:68:

( i ) SEQUENCE CHARACTERISTICS:
        ( A ) LENGTH: 112 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:68:

```
Met   Asn   Cys   Ser   Asn   Met   Ile   Asp   Glu   Ile   Ile   Thr   His   Leu   Lys   Gln
1                       5                             10                            15

Pro   Pro   Leu   Pro   Leu   Leu   Asp   Phe   Asn   Asn   Leu   Asn   Gly   Glu   Asp   Gln
                  20                        25                            30

Asp   Ile   Leu   Met   Glu   Asn   Asn   Leu   Arg   Arg   Pro   Asn   Leu   Glu   Ala   Phe
                  35                        40                            45

Asn   Arg   Ala   Val   Lys   Ser   Leu   Gln   Asn   Ala   Ser   Ala   Ile   Lys   Ser   Asn
      50                            55                            60

Leu   Gln   Lys   Leu   Asn   Ser   Cys   Leu   Pro   Leu   Ala   Thr   Ala   Ala   Pro   Thr
65                            70                      75                                  80

Arg   His   Pro   Ile   His   Ile   Lys   Ala   Gly   Asp   Trp   Asn   Glu   Phe   Arg   Arg
                        85                            90                            95

Lys   Leu   Thr   Phe   Tyr   Leu   Lys   Thr   Leu   Glu   Asn   Ala   Gln   Ala   Gln   Gln
                  100                         105                       110
```

( 2 ) INFORMATION FOR SEQ ID NO:69:

( i ) SEQUENCE CHARACTERISTICS:
( A ) LENGTH: 110 amino acids
( B ) TYPE: amino acid
( D ) TOPOLOGY: linear ( i i ) MOLECULE TYPE: peptide ( x i ) SEQUENCE DESCRIPTION: SEQ ID NO:69:

| Met | Asn | Cys | Ser | Asn | Met | Ile | Asp | Glu | Ile | Ile | Thr | His | Leu | Lys | Gln |
|---|---|---|---|---|---|---|---|---|---|---|---|---|---|---|---|
| 1 | | | | 5 | | | | | 10 | | | | | 15 | |
| Pro | Pro | Leu | Pro | Leu | Leu | Asp | Phe | Asn | Asn | Leu | Asn | Gly | Glu | Asp | Gln |
| | | | 20 | | | | | 25 | | | | | 30 | | |
| Asp | Ile | Leu | Met | Glu | Asn | Asn | Leu | Arg | Arg | Pro | Asn | Leu | Glu | Ala | Phe |
| | | | 35 | | | | 40 | | | | | 45 | | | |
| Asn | Arg | Ala | Val | Lys | Ser | Leu | Gln | Asn | Ala | Ser | Ala | Ile | Glu | Ser | Ile |
| | | 50 | | | | | 55 | | | | | 60 | | | |
| Leu | Lys | Asn | Leu | Leu | Pro | Cys | Leu | Pro | Leu | Ala | Thr | Ala | Ala | Pro | Thr |
| 65 | | | | | 70 | | | | | 75 | | | | | 80 |
| Arg | His | Pro | Ile | His | Ile | Lys | Asp | Leu | Asp | Glu | Phe | Arg | Arg | Lys | Leu |
| | | | | 85 | | | | | 90 | | | | | 95 | |
| Thr | Phe | Tyr | Leu | Lys | Thr | Leu | Glu | Asn | Ala | Gln | Ala | Gln | Gln | | |
| | | | 100 | | | | | 105 | | | | | 110 | | |

( 2 ) INFORMATION FOR SEQ ID NO:70:

( i ) SEQUENCE CHARACTERISTICS:
( A ) LENGTH: 112 amino acids
( B ) TYPE: amino acid
( D ) TOPOLOGY: linear ( i i ) MOLECULE TYPE: peptide ( x i ) SEQUENCE DESCRIPTION: SEQ ID NO:70:

| Met | Asn | Cys | Ser | Asn | Met | Ile | Asp | Glu | Ile | Ile | Thr | His | Leu | Lys | Gln |
|---|---|---|---|---|---|---|---|---|---|---|---|---|---|---|---|
| 1 | | | | 5 | | | | | 10 | | | | | 15 | |
| Pro | Pro | Leu | Pro | Leu | Leu | Asp | Phe | Asn | Asn | Leu | Asn | Gly | Glu | Asp | Gln |
| | | | 20 | | | | | 25 | | | | | 30 | | |
| Asp | Ser | Leu | Arg | Asn | Lys | Ser | Leu | Arg | Arg | Pro | Asn | Leu | Glu | Ala | Phe |
| | | | 35 | | | | | 40 | | | | | 45 | | |
| Asn | Arg | Ala | Val | Lys | Ser | Leu | Gln | Asn | Ala | Ser | Ala | Ile | Glu | Ser | Ile |
| | | 50 | | | | | 55 | | | | | 60 | | | |
| Leu | Lys | Asn | Leu | Leu | Pro | Cys | Leu | Pro | Leu | Ala | Thr | Ala | Ala | Pro | Thr |
| 65 | | | | | 70 | | | | | 75 | | | | | 80 |
| Arg | His | Pro | Ile | His | Ile | Lys | Asp | Gly | Asp | Trp | Asn | Glu | Phe | Arg | Arg |
| | | | | 85 | | | | | 90 | | | | | 95 | |
| Lys | Leu | Thr | Phe | Tyr | Leu | Lys | Thr | Leu | Glu | Asn | Ala | Gln | Ala | Gln | Gln |
| | | | 100 | | | | | 105 | | | | | 110 | | |

( 2 ) INFORMATION FOR SEQ ID NO:71:

( i ) SEQUENCE CHARACTERISTICS:
( A ) LENGTH: 112 amino acids
( B ) TYPE: amino acid
( D ) TOPOLOGY: linear ( i i ) MOLECULE TYPE: peptide ( x i ) SEQUENCE DESCRIPTION: SEQ ID NO:71:

| Met | Asn | Cys | Ser | Asn | Met | Ile | Asp | Glu | Ile | Ile | Thr | His | Leu | Lys | Gln |
|---|---|---|---|---|---|---|---|---|---|---|---|---|---|---|---|
| 1 | | | | 5 | | | | | 10 | | | | | 15 | |
| Pro | Pro | Leu | Pro | Leu | Leu | Asp | Phe | Asn | Asn | Leu | Asn | Gly | Glu | Asp | Gln |
| | | | 20 | | | | | 25 | | | | | 30 | | |

```
Asp  Ile  Leu  Met  Glu  Asn  Asn  Phe  Arg  Arg  Val  Asn  Leu  Ser  Lys  Phe
              35                       40                      45

Val  Glu  Ala  Val  Lys  Ser  Leu  Gln  Asn  Ala  Ser  Ala  Ile  Glu  Ser  Ile
         50                       55                      60

Leu  Lys  Asn  Leu  Leu  Pro  Cys  Leu  Pro  Leu  Ala  Thr  Ala  Ala  Pro  Thr
65                            70                 75                           80

Arg  His  Pro  Ile  His  Ile  Lys  Asp  Gly  Asp  Trp  Asn  Glu  Phe  Arg  Arg
                   85                       90                           95

Lys  Leu  Thr  Phe  Tyr  Leu  Lys  Thr  Leu  Glu  Asn  Ala  Gln  Ala  Gln  Gln
              100                      105                     110
```

( 2 ) INFORMATION FOR SEQ ID NO:72:

( i ) SEQUENCE CHARACTERISTICS:
        ( A ) LENGTH: 112 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:72:

```
Met  Asn  Cys  Ser  Asn  Met  Ile  Asp  Glu  Ile  Ile  Thr  His  Leu  Lys  Gln
1                    5                       10                      15

Pro  Pro  Leu  Pro  Leu  Leu  Asp  Phe  Asn  Asn  Leu  Asn  Gly  Glu  Asp  Gln
              20                       25                      30

Asp  Ile  Leu  Met  Glu  Asn  Asn  Leu  Arg  Arg  Pro  Asn  Leu  Glu  Ala  Phe
              35                       40                      45

Asn  Arg  Ser  Gln  Gly  Glu  Val  Asp  Asn  Ala  Ser  Ala  Ile  Glu  Ser  Ile
         50                       55                      60

Leu  Lys  Asn  Leu  Leu  Pro  Cys  Leu  Pro  Leu  Ala  Thr  Ala  Ala  Pro  Thr
65                            70                 75                           80

Arg  His  Pro  Ile  His  Ile  Lys  Asp  Gly  Asp  Trp  Asn  Glu  Phe  Arg  Arg
                   85                       90                           95

Lys  Leu  Thr  Phe  Tyr  Leu  Lys  Thr  Leu  Glu  Asn  Ala  Gln  Ala  Gln  Gln
              100                      105                     110
```

( 2 ) INFORMATION FOR SEQ ID NO:73:

( i ) SEQUENCE CHARACTERISTICS:
        ( A ) LENGTH: 105 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:73:

```
Met  Asn  Cys  Ser  Asn  Met  Ile  Asp  Glu  Ile  Ile  Thr  His  Leu  Lys  Asp
1                    5                       10                      15

Phe  Asn  Asn  Leu  Asn  Gly  Glu  Asp  Gln  Asp  Ile  Leu  Met  Glu  Asn  Asn
              20                       25                      30

Leu  Arg  Arg  Pro  Asn  Leu  Glu  Ala  Phe  Asn  Arg  Ala  Val  Lys  Ser  Leu
         35                       40                      45

Gln  Asn  Ala  Ser  Ala  Ile  Glu  Ser  Ile  Leu  Lys  Asn  Leu  Leu  Pro  Cys
         50                       55                      60

Leu  Pro  Leu  Ala  Thr  Ala  Ala  Pro  Thr  Arg  His  Pro  Ile  His  Ile  Lys
65                       70                       75                           80

Asp  Gly  Asp  Trp  Asn  Glu  Phe  Arg  Arg  Lys  Leu  Thr  Phe  Tyr  Leu  Lys
                   85                       90                           95

Thr  Leu  Glu  Asn  Ala  Gln  Ala  Gln  Gln
```

( 2 ) INFORMATION FOR SEQ ID NO:74:

(i) SEQUENCE CHARACTERISTICS:
(A) LENGTH: 112 amino acids
(B) TYPE: amino acid
(D) TOPOLOGY: linear (ii) MOLECULE TYPE: peptide (xi) SEQUENCE DESCRIPTION: SEQ ID NO:74:

| Met | Asn | Cys | Ser | Asn | Met | Ile | Asp | Glu | Ile | Ile | Thr | His | Leu | Lys | Gln |
|---|---|---|---|---|---|---|---|---|---|---|---|---|---|---|---|
| 1 | | | | 5 | | | | | 10 | | | | | 15 | |
| Pro | Pro | Leu | Pro | Leu | Leu | Asp | Phe | Asn | Asn | Leu | Thr | Asp | Asp | Glu | Gly |
| | | | 20 | | | | | 25 | | | | | 30 | | |
| Pro | Ile | Leu | Met | Glu | Asn | Asn | Leu | Arg | Arg | Pro | Asn | Leu | Glu | Ala | Phe |
| | | | 35 | | | | 40 | | | | | 45 | | | |
| Asn | Arg | Ala | Val | Lys | Ser | Leu | Gln | Asn | Ala | Ser | Ala | Ile | Glu | Ser | Ile |
| | | 50 | | | | 55 | | | | | 60 | | | | |
| Leu | Lys | Asn | Leu | Leu | Pro | Cys | Leu | Pro | Leu | Ala | Thr | Ala | Ala | Pro | Thr |
| 65 | | | | | 70 | | | | | 75 | | | | | 80 |
| Arg | His | Pro | Ile | His | Ile | Lys | Asp | Gly | Asp | Trp | Asn | Glu | Phe | Arg | Arg |
| | | | | 85 | | | | | 90 | | | | | 95 | |
| Lys | Leu | Thr | Phe | Tyr | Leu | Lys | Thr | Leu | Glu | Asn | Ala | Gln | Ala | Gln | Gln |
| | | | 100 | | | | | 105 | | | | | 110 | | |

( 2 ) INFORMATION FOR SEQ ID NO:75:

(i) SEQUENCE CHARACTERISTICS:
(A) LENGTH: 112 amino acids
(B) TYPE: amino acid
(D) TOPOLOGY: linear (ii) MOLECULE TYPE: peptide (xi) SEQUENCE DESCRIPTION: SEQ ID NO:75:

| Met | Asn | Cys | Ser | Asn | Met | Ile | Asp | Glu | Ile | Ile | Thr | His | Leu | Lys | Gln |
|---|---|---|---|---|---|---|---|---|---|---|---|---|---|---|---|
| 1 | | | | 5 | | | | | 10 | | | | | 15 | |
| Pro | Pro | Leu | Pro | Leu | Leu | Glu | Pro | Glu | Leu | Lys | Asn | Gly | Glu | Asp | Gln |
| | | | 20 | | | | | 25 | | | | | 30 | | |
| Asp | Ile | Leu | Met | Glu | Asn | Asn | Leu | Arg | Arg | Pro | Asn | Leu | Glu | Ala | Phe |
| | | | 35 | | | | | 40 | | | | | 45 | | |
| Asn | Arg | Ala | Val | Lys | Ser | Leu | Gln | Asn | Ala | Ser | Ala | Ile | Glu | Ser | Ile |
| | | 50 | | | | 55 | | | | | 60 | | | | |
| Leu | Lys | Asn | Leu | Leu | Pro | Cys | Leu | Pro | Leu | Ala | Thr | Ala | Ala | Pro | Thr |
| 65 | | | | | 70 | | | | | 75 | | | | | 80 |
| Arg | His | Pro | Ile | His | Ile | Lys | Asp | Gly | Asp | Trp | Asn | Glu | Phe | Arg | Arg |
| | | | | 85 | | | | | 90 | | | | | 95 | |
| Lys | Leu | Thr | Phe | Tyr | Leu | Lys | Thr | Leu | Glu | Asn | Ala | Gln | Ala | Gln | Gln |
| | | | 100 | | | | | 105 | | | | | 110 | | |

( 2 ) INFORMATION FOR SEQ ID NO:76:

(i) SEQUENCE CHARACTERISTICS:
(A) LENGTH: 113 amino acids
(B) TYPE: amino acid
(D) TOPOLOGY: linear (ii) MOLECULE TYPE: peptide (xi) SEQUENCE DESCRIPTION: SEQ ID NO:76:

```
  Met  Ala  Asn  Cys  Ser  Ser  Ile  Val  Lys  Glu  Ile  Ile  Gly  Lys  Leu  Pro
   1              5                        10                           15

Gln  Pro  Pro  Leu  Pro  Leu  Leu  Asp  Phe  Asn  Asn  Leu  Asn  Gly  Glu  Asp
                  20                        25                      30

Gln  Asp  Ile  Leu  Met  Glu  Asn  Asn  Leu  Arg  Arg  Pro  Asn  Leu  Glu  Ala
            35                        40                      45

Phe  Asn  Arg  Ala  Val  Lys  Ser  Leu  Gln  Asn  Ala  Ser  Ala  Ile  Glu  Ser
       50                       55                       60

Ile  Leu  Lys  Asn  Leu  Leu  Pro  Cys  Leu  Pro  Leu  Ala  Thr  Ala  Ala  Pro
  65                      70                       75                            80

Thr  Arg  His  Pro  Ile  His  Ile  Lys  Asp  Gly  Asp  Trp  Asn  Glu  Phe  Arg
                       85                       90                            95

Arg  Lys  Leu  Thr  Phe  Tyr  Leu  Lys  Thr  Leu  Glu  Asn  Ala  Gln  Ala  Gln
                 100                      105                      110

Gln
```

( 2 ) INFORMATION FOR SEQ ID NO:77:

( i ) SEQUENCE CHARACTERISTICS:
        ( A ) LENGTH: 336 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:77:

```
ATGAACTGCT  CTAACATGAT  CGATGAAATC  ATCACCCACC  TGAAGCAGCC  ACCGCTGCCG    60
CTGCTGGACT  TCAACAACCT  CAATGGTGAA  GACCAAGATA  TCCTGATGGA  AAATAACCTT   120
CGTCGTCCAA  ACCTCGAGGC  ATTCAACCGT  GCTGTCAAGT  CTCTGCAGAA  TGCATCAGCA   180
ATTGAGAGCA  TTCTTAAAAA  TCTCCTGCCA  TGTCTGCCGC  TAGCCACGGC  CGCACCCACG   240
CGACATCCAA  TCCATATCAA  GGCTGGTGAC  TGGAATGAAT  TCCGTCGTAA  ACTGACCTTC   300
TATCTGAAAA  CCTTGGAGAA  CGCGCAGGCT  CAACAG                               336
```

( 2 ) INFORMATION FOR SEQ ID NO:78:

( i ) SEQUENCE CHARACTERISTICS:
        ( A ) LENGTH: 342 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:78:

```
ATGAACTGCT  CTAACATGAT  CGATGAAATC  ATCACCCACC  TGAAGCAGCC  ACCGCTGCCG    60
CTGCTGGACT  TCAACAACCT  CAATGGTGAA  GACCAAGATA  TCCTGATGGA  AAATAACCTT   120
CGTCGTCCAA  ACCTCGAGGC  ATTCAACCGT  GCTGTCAAGT  CTCTGCAGCC  GGAAGACCGT   180
TACGTTATCG  AATCCATCCT  GAAAAACCTG  CTGCCGTGCC  TGCCGCTAGC  CACGGCCGCA   240
CCCACGCGAC  ATCCAATCCA  TATCAAGGCT  GGTGACTGGA  ATGAATTCCG  TCGTAAACTG   300
ACCTTCTATC  TGAAAACCTT  GGAGAACGCG  CAGGCTCAAC  AG                       342
```

( 2 ) INFORMATION FOR SEQ ID NO:79:

( i ) SEQUENCE CHARACTERISTICS:
        ( A ) LENGTH: 336 base pairs
        ( B ) TYPE: nucleic acid
        ( C ) STRANDEDNESS: double ( D ) TOPOLOGY: linear ( i i ) MOLECULE TYPE: DNA (genomic)

( x i ) SEQUENCE DESCRIPTION: SEQ ID NO:79:

| ATGAACTGCT | CTAACATGAT | CGATGAAATT | ATAACACACT | TAAAGCAGCC | ACCTTTGCCT | 60 |
| TTGCTGGACT | TCAACAACCT | CAATGGGGAA | GACCAAGACA | TTCTGATGGA | AAATAACCTT | 120 |
| CGAAGGCCAA | ACCTGGAGGC | ATTCAACAGG | GCTGTCAAGA | GTTTACAGAA | TGCATCAGCA | 180 |
| ATTGAGAGCA | TTCTTAAAAA | TCTCCTGCCA | TGTCTGCCGC | TAGCCACGGC | CGCACCCACG | 240 |
| CGACATCCAA | TCCATATCAA | GGCTGGTGAC | TGGAATGAAT | TCCGTCGTAA | ACTGACCTTC | 300 |
| TATCTGAAAA | CCTTGGAGAA | CGCGCAGGCT | CAACAG | | | 336 |

( 2 ) INFORMATION FOR SEQ ID NO:80:

( i ) SEQUENCE CHARACTERISTICS:
        ( A ) LENGTH: 336 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:80:

| ATGAACTGCT | CTAACATGAT | CGATGAAATT | ATAACACACT | TAAAGCAGCC | ACCTTTGCCT | 60 |
| TTGCTGGACT | TCAACAACCT | CAATGGGGAA | GACCAAGACA | TTCTGATGGA | AAATAACCTT | 120 |
| CGAAGGCCAA | ACCTGGAGGC | ATTCAACAGG | GCTGTCAAGA | GTTTACAGAA | TGCATCAGCA | 180 |
| ATTGAGAGCA | TTCTTAAAAA | TCTCCTGCCA | TGTCTGCCGC | TAGCCACGGC | CGCATCCGCT | 240 |
| CTGCCGCCAA | TCCATATCAA | GGACGGTGAC | TGGAATGAAT | TCCGTCGTAA | ACTGACCTTC | 300 |
| TATCTGAAAA | CCTTGGAGAA | CGCGCAGGCT | CAACAG | | | 336 |

( 2 ) INFORMATION FOR SEQ ID NO:81:

( i ) SEQUENCE CHARACTERISTICS:
        ( A ) LENGTH: 336 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:81:

| ATGAACTGCT | CTAACATGAT | CGATGAAATT | ATAACACACT | TAAAGCAGCC | ACCTTTGCCT | 60 |
| TTGCTGGACT | TCAACAACCT | CAATGGGGAA | GACCAAGACA | TTCTGATGGA | AAATAACCTT | 120 |
| CGAAGGCCAA | ACCTGGAGGC | ATTCAACAGG | GCTGTCAAGA | GTTTACAGAA | TGCATCAGCA | 180 |
| ATTGAGAGCA | TTCTTAAAAA | TCTCCTGCCA | TGTCTGCCGC | TAGCCACGGC | CGCACCGACG | 240 |
| CGTCATGGTG | TTTTCATCCG | TGACGGTGAC | TGGAATGAAT | TCCGTCGTAA | ACTGACCTTC | 300 |
| TATCTGAAAA | CCTTGGAGAA | CGCGCAGGCT | CAACAG | | | 336 |

( 2 ) INFORMATION FOR SEQ ID NO:82:

( i ) SEQUENCE CHARACTERISTICS:
        ( A ) LENGTH: 336 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:82:

```
ATGAACTGCT CTAACATGAT CGATGAAATT ATAACACACT TAAAGCAGCC ACCTTTGCCT        60

TTGCTGGACT TCAACAACCT CAATGGGGAA GACCAAGACA TTCTGATGGA AAATAACCTT       120

CGAAGGCCAA ACCTGGAGGC ATTCAACAGG GCTGTCAAGA GTTTACAGAA TGCATCAGCA       180

ATTGAGAGCA TTCTTAAAAA TCTCCTGCCA TGTCTGCCGA CCTCCGCTAA CGATCCGACG       240

CGTCATCCAA TCCATATCAA GGACGGTGAC TGGAACGAAT TCCGTCGTAA ACTGACCTTC       300

TATCTGAAAA CCTTGGAGAA CGCGCAGGCT CAACAG                                 336
```

( 2 ) INFORMATION FOR SEQ ID NO:83:

( i ) SEQUENCE CHARACTERISTICS:
        ( A ) LENGTH: 336 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:83:

```
ATGAACTGCT CTAACATGAT CGATGAAATT ATAACACACT TAAAGCAGCC ACCTTTGCCT        60

TTGCTGGACT TCAACAACCT CAATGGGGAA GACCAAGACA TTCTGATGGA AAATAACCTT       120

CGAAGGCCAA ACCTGGAGGC ATTCAACAGG GCTGTCAAGA GTTTACAGAA TGCATCAGCA       180

ATTAAAAGCA ACCTGCAGAA GCTCAACTCC TGTCTGCCGC TAGCCACGGC CGCACCCACG       240

CGACATCCAA TCCATATCAA GGCTGGTGAC TGGAATGAAT TCCGTCGTAA ACTGACCTTC       300

TATCTGAAAA CCTTGGAGAA CGCGCAGGCT CAACAG                                 336
```

( 2 ) INFORMATION FOR SEQ ID NO:84:

( i ) SEQUENCE CHARACTERISTICS:
        ( A ) LENGTH: 330 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:84:

```
ATGAACTGCT CTAACATGAT CGATGAAATT ATAACACACT TAAAGCAGCC ACCTTTGCCT        60

TTGCTGGACT TCAACAACCT CAATGGGGAA GACCAAGACA TTCTGATGGA AAATAACCTT       120

CGAAGGCCAA ACCTGGAGGC ATTCAACAGG GCTGTCAAGA GTTTACAGAA TGCATCAGCA       180

ATTGAGAGCA TTCTTAAAAA TCTCCTGCCA TGTCTGCCGC TAGCCACGGC CGCACCGACG       240

CGTCATCCAA TCCATATCAA GGACCTGGAC GAATTCCGTC GTAAACTGAC CTTCTATCTG       300

AAAACCTTGG AGAACGCGCA GGCTCAACAG                                        330
```

( 2 ) INFORMATION FOR SEQ ID NO:85:

( i ) SEQUENCE CHARACTERISTICS:
        ( A ) LENGTH: 336 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:85:

```
ATGAACTGCT CTAACATGAT CGATGAAATC ATCACCCACC TGAAGCAGCC ACCGCTGCCG        60

CTGCTGGACT TCAACAACCT CAATGGTGAA GACCAAGATA TCCTGATGGA AAATAACCTT       120
```

| CGTCGTCCAA | ACCTCGAGGC | ATTCAACCGT | GCTGTCAAGT | CTCTGCAGAA | TGCATCAGCA | 180 |
| ATTGAGAGCA | TTCTTAAAAA | TCTCCTGCCA | TGTCTGCCCC | TGGCCACGGC | CGCACCCACG | 240 |
| CGACATCCAA | TCCATATCAA | GGACGGTGAC | TGGAATGAAT | TCCGTCGTAA | ACTGACCTTC | 300 |
| TATCTGAAAA | CCTTGGAGAA | CGCGCAGGCT | CAACAG | | | 336 |

( 2 ) INFORMATION FOR SEQ ID NO:86:

( i ) SEQUENCE CHARACTERISTICS:
        ( A ) LENGTH: 336 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:86:

| ATGAACTGCT | CTAACATGAT | CGATGAAATC | ATCACCCACC | TGAAGCAGCC | ACCGCTGCCG | 60 |
| CTGCTGGACT | TCAACAACCT | CAATGGTGAA | GACCAAGATT | CCCTGCGTAA | CAAATCCCTT | 120 |
| CGTCGTCCAA | ACCTCGAGGC | ATTCAACCGT | GCTGTCAAGT | CTCTGCAGAA | TGCATCAGCA | 180 |
| ATTGAGAGCA | TTCTTAAAAA | TCTCCTGCCA | TGTCTGCCCC | TGGCCACGGC | CGCACCCACG | 240 |
| CGACATCCAA | TCCATATCAA | GGACGGTGAC | TGGAATGAAT | TCCGTCGTAA | ACTGACCTTC | 300 |
| TATCTGAAAA | CCTTGGAGAA | CGCGCAGGCT | CAACAG | | | 336 |

( 2 ) INFORMATION FOR SEQ ID NO:87:

( i ) SEQUENCE CHARACTERISTICS:
        ( A ) LENGTH: 336 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:87:

| ATGAACTGCT | CTAACATGAT | CGATGAAATC | ATCACCCACC | TGAAGCAGCC | ACCGCTGCCG | 60 |
| CTGCTGGACT | TCAACAACCT | CAATGGTGAA | GACCAAGATA | TCCTGATGGA | AAATAACTTC | 120 |
| CGTCGTGTTA | ACCTCTCCAA | ATTCGTTGAA | GCTGTCAAGT | CTCTGCAGAA | TGCATCAGCA | 180 |
| ATTGAGAGCA | TTCTTAAAAA | TCTCCTGCCA | TGTCTGCCCC | TGGCCACGGC | CGCACCCACG | 240 |
| CGACATCCAA | TCCATATCAA | GGACGGTGAC | TGGAATGAAT | TCCGTCGTAA | ACTGACCTTC | 300 |
| TATCTGAAAA | CCTTGGAGAA | CGCGCAGGCT | CAACAG | | | 336 |

( 2 ) INFORMATION FOR SEQ ID NO:88:

( i ) SEQUENCE CHARACTERISTICS:
        ( A ) LENGTH: 336 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:88:

| ATGAACTGCT | CTAACATGAT | CGATGAAATC | ATCACCCACC | TGAAGCAGCC | ACCGCTGCCG | 60 |
| CTGCTGGACT | TCAACAACCT | CAATGGTGAA | GACCAAGATA | TCCTGATGGA | AAATAACTT | 120 |
| CGTCGTCCAA | ACCTCGAGGC | ATTCAACCGT | TCCCAGGGTG | AAGTTGACAA | TGCATCAGCA | 180 |
| ATTGAGAGCA | TTCTTAAAAA | TCTCCTGCCA | TGTCTGCCCC | TGGCCACGGC | CGCACCCACG | 240 |
| CGACATCCAA | TCCATATCAA | GGACGGTGAC | TGGAATGAAT | TCCGTCGTAA | ACTGACCTTC | 300 |

TATCTGAAAA CCTTGGAGAA CGCGCAGGCT CAACAG 336

( 2 ) INFORMATION FOR SEQ ID NO:89:

( i ) SEQUENCE CHARACTERISTICS:
        ( A ) LENGTH: 315 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:89:

ATGAACTGCT CTAACATGAT CGATGAAATC ATCACCCACC TGAAGGACTT CAACAACCTC 60

AATGGTGAAG ACCAAGATAT CCTGATGGAA AATAACCTTC GTCGTCCAAA CCTCGAGGCA 120

TTCAACCGTG CTGTCAAGTC TCTGCAGAAT GCATCAGCAA TTGAGAGCAT TCTTAAAAAT 180

CTCCTGCCAT GTCTGCCCCT GGCCACGGCC GCACCCACGC GACATCCAAT CCATATCAAG 240

GACGGTGACT GGAATGAATT CCGTCGTAAA CTGACCTTCT ATCTGAAAAC CTTGGAGAAC 300

GCGCAGGCTC AACAG 315

( 2 ) INFORMATION FOR SEQ ID NO:90:

( i ) SEQUENCE CHARACTERISTICS:
        ( A ) LENGTH: 336 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:90:

ATGAACTGCT CTAACATGAT CGATGAAATC ATCACCCACC TGAAGCAGCC ACCGCTGCCG 60

CTGCTGGACT TCAACAACCT CACCGACGAC GAAGGTCCGA TCCTGATGGA AAATAACCTT 120

CGTCGTCCAA ACCTCGAGGC ATTCAACCGT GCTGTCAAGT CTCTGCAGAA TGCATCAGCA 180

ATTGAGAGCA TTCTTAAAAA TCTCCTGCCA TGTCTGCCCC TGGCCACGGC CGCACCCACG 240

CGACATCCAA TCCATATCAA GGACGGTGAC TGGAATGAAT TCCGTCGTAA ACTGACCTTC 300

TATCTGAAAA CCTTGGAGAA CGCGCAGGCT CAACAG 336

( 2 ) INFORMATION FOR SEQ ID NO:91:

( i ) SEQUENCE CHARACTERISTICS:
        ( A ) LENGTH: 336 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:91:

ATGAACTGCT CTAACATGAT CGATGAAATC ATCACCCACC TGAAGCAGCC ACCGCTGCCG 60

CTGCTGGAAC CGGAACTGAA AAATGGTGAA GACCAAGATA TCCTGATGGA AAATAACCTT 120

CGTCGTCCAA ACCTCGAGGC ATTCAACCGT GCTGTCAAGT CTCTGCAGAA TGCATCAGCA 180

ATTGAGAGCA TTCTTAAAAA TCTCCTGCCA TGTCTGCCCC TGGCCACGGC CGCACCCACG 240

CGACATCCAA TCCATATCAA GGACGGTGAC TGGAATGAAT TCCGTCGTAA ACTGACCTTC 300

TATCTGAAAA CCTTGGAGAA CGCGCAGGCT CAACAG 336

( 2 ) INFORMATION FOR SEQ ID NO:92:

( i ) SEQUENCE CHARACTERISTICS:
  ( A ) LENGTH: 339 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:92:

| | | | | | | |
|---|---|---|---|---|---|---|
| ATGGCTAACT | GCTCTAACAT | GATCGATGAA | ATCATCACCC | ACCTGAAGCA | GCCACCGCTG | 60 |
| CCGCTGCTGG | ACTTCAACAA | CCTCAATGGT | GAAGACCAAG | ATATCCTGAT | GGAAAATAAC | 120 |
| CTTCGTCGTC | CAAACCTCGA | GGCATTCAAC | CGTGCTGTCA | AGTCTCTGCA | GAATGCATCA | 180 |
| GCAATTGAGA | GCATTCTTAA | AAATCTCCTG | CCATGTCTGC | CCCTGGCCAC | GGCCGCACCC | 240 |
| ACGCGACATC | CAATCCATAT | CAAGGACGGT | GACTGGAATG | AATTCCGTCG | TAAACTGACC | 300 |
| TTCTATCTGA | AAACCTTGGA | GAACGCGCAG | GCTCAACAG | | | 339 |

( 2 ) INFORMATION FOR SEQ ID NO:93:

( i ) SEQUENCE CHARACTERISTICS:
    ( A ) LENGTH: 339 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:93:

| | | | | | | |
|---|---|---|---|---|---|---|
| ATGGCTAACT | GCTCTTCCAT | CGTTAAAGAA | ATCATCGGTA | AACTGCCGCA | GCCACCGCTG | 60 |
| CCGCTGCTGG | ACTTCAACAA | CCTCAATGGT | GAAGACCAAG | ATATCCTGAT | GGAAAATAAC | 120 |
| CTTCGTCGTC | CAAACCTCGA | GGCATTCAAC | CGTGCTGTCA | AGTCTCTGCA | GAATGCATCA | 180 |
| GCAATTGAGA | GCATTCTTAA | AAATCTCCTG | CCATGTCTGC | CCCTGGCCAC | GGCCGCACCC | 240 |
| ACGCGACATC | CAATCCATAT | CAAGGACGGT | GACTGGAATG | AATTCCGTCG | TAAACTGACC | 300 |
| TTCTATCTGA | AAACCTTGGA | GAACGCGCAG | GCTCAACAG | | | 339 |

( 2 ) INFORMATION FOR SEQ ID NO:94:

( i ) SEQUENCE CHARACTERISTICS:
    ( A ) LENGTH: 360 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:94:

| | | | | | | |
|---|---|---|---|---|---|---|
| ATGAACTGCT | CTAACATGAT | CGATGAAATT | ATAACACACT | TAAAGCAGCC | ACCTTTGCCT | 60 |
| TTGCTGGACT | TCAACAACCT | CAATGGGAA | GACCAAGACA | TTCTGATGGA | AAATAACCTT | 120 |
| CGAAGGCCAA | ACCTGGAGGC | ATTCAACAGG | CTGTCAAGA | GTTTACAGAA | TGCATCAGCA | 180 |
| ATTGAGAGCA | TTCTTAAAAA | TCTCCTGCCA | TGTCTGCCCC | TGGCCACGGC | CGCACCCACG | 240 |
| CGACATCCAA | TCCATATCAA | GGACGGTGAC | TGGAATGAAT | TCCGTCGTAA | ACTGACCTTC | 300 |
| TATCTGAAAA | CCTTGGAGAA | CGCGCAGGCT | CAACAGACCA | CTCTGTCGCT | AGCGATCTTT | 360 |

( 2 ) INFORMATION FOR SEQ ID NO:95:

( i ) SEQUENCE CHARACTERISTICS:
    ( A ) LENGTH: 378 base pairs
    ( B ) TYPE: nucleic acid
    ( C ) STRANDEDNESS: double 5,501,962

109                                                                                              110
-continued ( D ) TOPOLOGY: linear ( i i ) MOLECULE TYPE: DNA (genomic)

( x i ) SEQUENCE DESCRIPTION: SEQ ID NO:95:

| ATGGCTCCAA | TGACTCAGAC | TACTTCTCTT | AAGACTTCTT | GGGTTAACTG | CTCTAACATG | 60 |
| ATCGATGAAA | TTATAACACA | CTTAAAGCAG | CCACCTTTGC | CTTTGCTGGA | CTTCAACAAC | 120 |
| CTCAATGGGG | AAGACCAAGA | CATTCTGATG | GAAAATAACC | TTCGAAGGCC | AAACCTGGAG | 180 |
| GCATTCAACA | GGGCTGTCAA | GAGTTTACAG | AATGCATCAG | CAATTGAGAG | CATTCTTAAA | 240 |
| AATCTCCTGC | CATGTCTGCC | CCTGGCCACG | GCCGCACCCA | CGCGACATCC | AATCCATATC | 300 |
| AAGGACGGTG | ACTGGAATGA | ATTCCGTCGT | AAACTGACCT | TCTATCTGAA | AACCTTGGAG | 360 |
| AACGCGCAGG | CTCAACAG   |            |            |            |            | 378 |

( 2 ) INFORMATION FOR SEQ ID NO:96:

( i ) SEQUENCE CHARACTERISTICS:
        ( A ) LENGTH: 336 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:96:

| ATGAACTGCT | CTAACATGAT | CGATGAAATT | ATAACACACT | TAAAGCAGCC | ACCTTTGCCT | 60 |
| TTGCTGGACT | TCAACAACCT | CAATGGGGAA | GACCAAGACA | TTCTGATGGA | AAATAACCTT | 120 |
| CGAAGGCCAA | ACCTGGAGGC | ATTCAACAGG | GCTGTCAAGA | GTTTACAGAA | TGCATCAGCA | 180 |
| ATTGAGAGCA | TTCTTAAAAA | TCTCCTGCCA | TGTCTGCCCC | TGGCCACGGC | CGCACCCACG | 240 |
| CGACATCCAA | TCCATATCAA | GGACGGTGAC | TGGAATGAAT | TCCGTCGTAA | ACTGACCTTC | 300 |
| TATCTGAAAA | CCTTGGAGAA | CGCGCAGGCT | CAACAG     |            |            | 336 |

( 2 ) INFORMATION FOR SEQ ID NO:97:

( i ) SEQUENCE CHARACTERISTICS:
        ( A ) LENGTH: 336 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:97:

| ATGAACTGCT | CTAACATGAT | CGATGAAATC | ATCACCCACC | TGAAGCAGCC | ACCGCTGCCG | 60 |
| CTGCTGGACT | TCAACAACCT | CAATGGTGAA | GACCAAGATA | TCCTGATGGA | AAATAACCTT | 120 |
| CGTCGTCCAA | ACCTCGAGGC | ATTCAACCGT | GCTGTCAAGT | CTCTGCAGAA | TGCATCAGCA | 180 |
| ATTGAGAGCA | TTCTTAAAAA | TCTCCTGCCA | TGTCTGCCCC | TGGCCACGGC | CGCACCCACG | 240 |
| CGACATCCAA | TCCATATCAA | GGACGGTGAC | TGGAATGAAT | TCCGTCGTAA | ACTGACCTTC | 300 |
| TATCTGAAAA | CCTTGGAGAA | CGCGCAGGCT | CAACAG     |            |            | 336 |

( 2 ) INFORMATION FOR SEQ ID NO:98:

( i ) SEQUENCE CHARACTERISTICS:
        ( A ) LENGTH: 225 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:98:

| | | | | | |
|---|---|---|---|---|---|
| ATGAACTGCT | CTAACATGAT | CGATGAAATT | ATAACACACT | TAAAGCAGCC | ACCTTTGCCT | 60
| TTGCTGGACT | TCAACAACCT | CAATGGGGAA | GACCAAGACA | TTCTGATGGA | AAATAACCTT | 120
| CGAAGGCCAA | ACCTGGAGGC | ATTCAACAGG | GCTGTCAAGA | GTTTACAGAA | TGCATCAGCA | 180
| ATTGAGAGCA | TTCTTAAAAA | TCTCCTGCCA | TGTCTGCCGC | TAGCC | | 225

( 2 ) INFORMATION FOR SEQ ID NO:99:

( i ) SEQUENCE CHARACTERISTICS:
        ( A ) LENGTH: 360 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:99:

| | | | | | |
|---|---|---|---|---|---|
| ATGAACTGCT | CTAACATGAT | CGATGAAATT | ATAACACACT | TAAAGCAGCC | ACCTTTGCCT | 60
| TTGCTGGACT | TCAACAACCT | CAATGGGGAA | GACCAAGACA | TTCTGATGGA | AAATAACCTT | 120
| CGAAGGCCAA | ACCTGGAGGC | ATTCAACAGG | GCTGTCAAGA | GTTTACAGAA | TGCATCAGCA | 180
| ATTGAGAGCA | TTCTTAAAAA | TCTCCTGCCA | TGTCTGCCCC | TGGCCACGGC | CGCACCCACG | 240
| CGACATCCAA | TCCATATCAA | GGACGGTGAC | TGGAATGAAT | TCCGTCGTAA | ACTGACCTTC | 300
| TATCTGAAAA | CCTTGGAGAA | CGCGCAGGCT | CAACAGACCA | CTCTGTCGCT | AGCGATCTTT | 360

( 2 ) INFORMATION FOR SEQ ID NO:100:

( i ) SEQUENCE CHARACTERISTICS:
        ( A ) LENGTH: 336 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:100:

| | | | | | |
|---|---|---|---|---|---|
| ATGAACTGCT | CTAACATGAT | CGATGAAATC | ATCACCCACC | TGAAGCAGCC | ACCGCTGCCG | 60
| CTGCTGGACT | TCAACAACCT | CAATGGTGAA | GACCAAGATA | TCCTGATGGA | AAATAACCTT | 120
| CGTCGTCCAA | ACCTCGAGGC | ATTCAACGT | GCTGTCAAGT | CTCTGCAGAA | TGCATCAGCA | 180
| ATTGAGAGCA | TTCTTAAAAA | TCTCCTGCCA | TGTCTGCCGC | TAGCCACGGC | CGCACCCACG | 240
| CGACATCCAA | TCCATATCAA | GGCTGGTGAC | TGGAATGAAT | TCCGTCGTAA | ACTGACCTTC | 300
| TATCTGAAAA | CCTTGGAGAA | CGCGCAGGCT | CAACAG | | | 336

( 2 ) INFORMATION FOR SEQ ID NO:101:

( i ) SEQUENCE CHARACTERISTICS:
        ( A ) LENGTH: 336 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:101:

| | | | | | |
|---|---|---|---|---|---|
| ATGAACTGCT | CTAACATGAT | CGATGAAATT | ATAACACACT | TAAAGCAGCC | ACCTTTGCCT | 60
| TTGCTGGACT | TCAACAACCT | CAATGGGGAA | GACCAAGACA | TTCTGATGGA | AAATAACCTT | 120
| CGAAGGCCAA | ACCTGGAGGC | ATTCAACAGG | GCTGTCAAGA | GTTTACAGAA | TGCATCAGCA | 180

| | | | | | | |
|---|---|---|---|---|---|---|
| ATTGAGAGCA | TTCTTAAAAA | TCTCCTGCCA | TGTCTGCCGC | TAGCCACGGC | CGCACCCACG | 240 |
| CGACATCCAA | TCCATATCAA | GGCTGGTGAC | TGGAATGAAT | TCCGTCGTAA | ACTGACCTTC | 300 |
| TATCTGAAAA | CCTTGGAGAA | CGCGCAGGCT | CAACAG | | | 336 |

( 2 ) INFORMATION FOR SEQ ID NO:102:

( i ) SEQUENCE CHARACTERISTICS:
        ( A ) LENGTH: 339 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:102:

| | | | | | | |
|---|---|---|---|---|---|---|
| ATGGCTAACT | GCTCTAACAT | GATCGATGAA | ATCATCACCC | ACCTGAAGCA | GCCACCGCTG | 60 |
| CCGCTGCTGG | ACTTCAACAA | CCTCAATGGT | GAAGACCAAG | ATATCCTGAT | GGAAAATAAC | 120 |
| CTTCGTCGTC | CAAACCTCGA | GGCATTCAAC | CGTGCTGTCA | AGTCTCTGCA | GAATGCATCA | 180 |
| GCAATTGAGA | GCATTCTTAA | AAATCTCCTG | CCATGTCTGC | CCTGGCCAC | GGCCGCACCC | 240 |
| ACGCGACATC | CAATCCATAT | CAAGGACGGT | GACTGGAATG | AATTCCGTCG | TAAACTGACC | 300 |
| TTCTATCTGA | AAACCTTGGA | GAACGCGCAG | GCTCAACAG | | | 339 |

( 2 ) INFORMATION FOR SEQ ID NO:103:

( i ) SEQUENCE CHARACTERISTICS:
        ( A ) LENGTH: 339 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:103:

| | | | | | | |
|---|---|---|---|---|---|---|
| ATGGCTAACT | GCTCTAACAT | GATCGATGAA | ATTATAACAC | ACTTAAAGCA | GCCACCTTTG | 60 |
| CCTTTGCTGG | ACTTCAACAA | CCTCAATGGG | GAAGACCAAG | ACATTCTGAT | GGAAAATAAC | 120 |
| CTTCGAAGGC | CAAACCTGGA | GGCATTCAAC | AGGGCTGTCA | AGAGTTTACA | GAATGCATCA | 180 |
| GCAATTGAGA | GCATTCTTAA | AAATCTCCTG | CCATGTCTGC | CCTGGCCAC | GGCCGCACCC | 240 |
| ACGCGACATC | CAATCCATAT | CAAGGACGGT | GACTGGAATG | AATTCCGTCG | TAAACTGACC | 300 |
| TTCTATCTGA | AAACCTTGGA | GAACGCGCAG | GCTCAACAG | | | 339 |

( 2 ) INFORMATION FOR SEQ ID NO:104:

( i ) SEQUENCE CHARACTERISTICS:
        ( A ) LENGTH: 408 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:104:

| | | | | | | |
|---|---|---|---|---|---|---|
| ATGGCTCCAA | TGACTCAGAC | TACTTCTCTT | AAGACTTCTT | GGGTTAACTG | CTCTAACATG | 60 |
| ATCGATGAAA | TTATAACACA | CTTAAAGCAG | CCACCTTTGC | CTTTGCTGGA | CTTCAACAAC | 120 |
| CTCAATGGGG | AAGACCAAGA | CATTCTGATG | AAAATAACC | TTCGAAGGC | AAACCTGGAG | 180 |
| GCATTCAACA | GGGCTGTCAA | GAGTTTACAG | AATGCATCAG | CAATTGAGAG | CATTCTTAAA | 240 |
| AATCTCCTGC | CATGTCTGCC | CTGGCCACG | GCCGCACCCA | CGCGACATCC | AATCCATATC | 300 |
| AAGGACGGTG | ACTGGAATGA | ATTCCGTCGT | AAACTGACCT | TCTATCTGAA | AACCTTGGAG | 360 |

AACGCGCAGG CTCAACAGAC CACTCTGTCG CTAGCGATCT TTTAATAA     408

( 2 ) INFORMATION FOR SEQ ID NO:105:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:105:

Ser Ala Leu Pro
1

( 2 ) INFORMATION FOR SEQ ID NO:106:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:106:

Ser Ile Val Lys Glu Ile Ile Gly Lys Leu Pro
1               5                       10

( 2 ) INFORMATION FOR SEQ ID NO:107:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:107:

Gly Val Phe Ile Arg
1               5

( 2 ) INFORMATION FOR SEQ ID NO:108:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:108:

Cys Leu Pro Thr Ser Ala Asn Asp
1               5

( 2 ) INFORMATION FOR SEQ ID NO:109:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:109:

Lys Ser Asn Leu Gln Lys Leu Asn Ser
1               5

( 2 ) INFORMATION FOR SEQ ID NO:110:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:110:

Ser Leu Arg Asn Lys Ser
1               5

( 2 ) INFORMATION FOR SEQ ID NO:111:

( i ) SEQUENCE CHARACTERISTICS:
    ( A ) LENGTH: 11 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:111:

Phe Arg Arg Val Asn Leu Ser Lys Phe Val Glu
1               5                   10

( 2 ) INFORMATION FOR SEQ ID NO:112:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:112:

Ser Gln Gly Glu Val Asp
1               5

( 2 ) INFORMATION FOR SEQ ID NO:113:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:113:

Gln Pro Pro Leu Pro Leu Leu
1               5

( 2 ) INFORMATION FOR SEQ ID NO:114:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:114:

Thr Asp Asp Glu Gly Pro
1               5

( 2 ) INFORMATION FOR SEQ ID NO:115:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:115:

Glu Pro Glu Leu Lys
1               5

( 2 ) INFORMATION FOR SEQ ID NO:116:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( x i ) SEQUENCE DESCRIPTION: SEQ ID NO:116:

Pro Glu Asp Arg Tyr Val Ile
1               5

( 2 ) INFORMATION FOR SEQ ID NO:117:

( i ) SEQUENCE CHARACTERISTICS:
( A ) LENGTH: 3 amino acids
( B ) TYPE: amino acid
( D ) TOPOLOGY: linear ( i i ) MOLECULE TYPE: peptide ( x i ) SEQUENCE DESCRIPTION: SEQ ID NO:117:

Asp Leu Asp
1

( 2 ) INFORMATION FOR SEQ ID NO:118:

( i ) SEQUENCE CHARACTERISTICS:
( A ) LENGTH: 140 amino acids
( B ) TYPE: amino acid
( D ) TOPOLOGY: linear ( i i ) MOLECULE TYPE: peptide ( x i ) SEQUENCE DESCRIPTION: SEQ ID NO:118:

Ala Ser Ile Ser Gly Arg Asp Thr His Arg Leu Thr Arg Thr Leu Asn
1               5                   10                  15

Cys Ser Ser Ile Val Lys Glu Ile Ile Gly Lys Leu Pro Glu Pro Glu
                20                  25                  30

Leu Lys Thr Asp Asp Glu Gly Pro Ser Leu Arg Asn Lys Ser Phe Arg
            35                  40                  45

Arg Val Asn Leu Ser Lys Phe Val Glu Ser Gln Gly Glu Val Asp Pro
        50                  55                  60

Glu Asp Arg Tyr Val Ile Lys Ser Asn Leu Gln Lys Leu Asn Cys Cys
65                  70                  75                  80

Leu Pro Thr Ser Ala Asn Asp Ser Ala Leu Pro Gly Val Phe Ile Arg
                85                  90                  95

Asp Leu Asp Asp Phe Arg Lys Lys Leu Arg Phe Tyr Met Val His Leu
            100                 105                 110

Asn Asp Leu Glu Thr Val Leu Thr Ser Arg Pro Pro Gln Pro Ala Ser
        115                 120                 125

Gly Ser Val Ser Pro Asn Arg Gly Thr Val Glu Cys
    130                 135                 140

( 2 ) INFORMATION FOR SEQ ID NO:119:

( i ) SEQUENCE CHARACTERISTICS:
     ( A ) LENGTH: 13 amino acids
     ( B ) TYPE: amino acid
     ( D ) TOPOLOGY: linear ( i i ) MOLECULE TYPE: peptide ( x i ) SEQUENCE DESCRIPTION: SEQ ID NO:119:

Met Ala Tyr Pro Glu Thr Asp Tyr Lys Asp Asp Asp Lys
 1               5                  10

( 2 ) INFORMATION FOR SEQ ID NO:120:

( i ) SEQUENCE CHARACTERISTICS:
          ( A ) LENGTH: 414 base pairs
          ( B ) TYPE: nucleic acid
          ( C ) STRANDEDNESS: double
          ( D ) TOPOLOGY: linear ( i i ) MOLECULE TYPE: DNA (genomic)

( x i ) SEQUENCE DESCRIPTION: SEQ ID NO:120:

```
AAGCTTATTA AAAGATCGCT AGCGACAGAG TGGTCTGTTG AGCCTGCGCG TTCTCCAAGG     60
TTTTCAGATA GAAGGTCAGT TTACGACGGA ATTCATTCCA GTCACCGTCC TTGATATGGA    120
TTGGATGTCG CGTGGGTGCG GCCGTGGCCA GGGGCAGACA TGGCAGGAGA TTTTTAAGAA    180
TGCTCTCAAT TGCTGATGCA TTCTGTAAAC TCTTGACAGC CCTGTTGAAT GCCTCCAGGT    240
TTGGCCTTCG AAGGTTATTT CCATCAGAA TGTCTTGGTC TTCCCCATTG AGGTTGTTGA     300
AGTCCAGCAA AGGCAAAGGT GGCTGCTTTA AGTGTGTTAT AATTTCATCG ATCATGTTAG    360
AGCAGTTAAC CCAAGAAGTC TTAAGAGAAG TAGTCTGAGT CATTGGAGCC ATGG          414
```

( 2 ) INFORMATION FOR SEQ ID NO:121:

( i ) SEQUENCE CHARACTERISTICS:
          ( A ) LENGTH: 414 base pairs
          ( B ) TYPE: nucleic acid
          ( C ) STRANDEDNESS: double
          ( D ) TOPOLOGY: linear ( i i ) MOLECULE TYPE: DNA (genomic)

( x i ) SEQUENCE DESCRIPTION: SEQ ID NO:121:

```
CCATGGCTCC AATGACTCAG ACTACTTCTC TTAAGACTTC TTGGGTTAAC TGCTCTAACA     60
TGATCGATGA AATTATAACA CACTTAAAGC AGCCACCTTT GCCTTTGCTG GACTTCAACA    120
ACCTCAATGG GGAAGACCAA GACATTCTGA TGGAAAATAA CCTTCGAAGG CCAAACCTGG    180
AGGCATTCAA CAGGGCTGTC AAGAGTTTAC AGAATGCATC AGCAATTGAG AGCATTCTTA    240
AAAATCTCCT GCCATGTCTG CCCCTGGCCA CGGCCGCACC CACGCGACAT CCAATCCATA    300
TCAAGGACGG TGACTGGAAT GAATTCCGTC GTAAACTGAC CTTCTATCTG AAAACCTTGG    360
AGAACGCGCA GGCTCAACAG ACCACTCTGT CGCTAGCGAT CTTTTAATAA GCTT          414
```

What is claimed is:

1. A polypeptide which is selected from the group consisting of

Met Asn Cys Ser Asn Met Ile Asp
              Glu Ile Ile Thr His Leu Lys
Gln Pro Pro Leu Pro Leu Leu Asp
              Phe Asn Asn Leu Asn Gly Glu
Asp Gln Asp Ile Leu Met Glu Asn
              Asn Leu Arg Arg Pro Asn Leu
Glu Ala Phe Asn Arg Ala Val Lys
Tyr Val Ile Ser Leu Gln Pro Glu Asp Arg
              Glu Ser Ile Leu Lys
              Asn Leu Leu Pro Cys Leu Pro
Leu Ala Thr Ala Ala Pro Thr Arg
              His Pro Ile His Ile Lys Ala
Gly Asp Trp Asn Glu Phe Arg Arg
              Lys Leu Thr Phe Tyr Leu Lys
Thr Leu Glu Asn Ala Gln Ala Gln
              Gln [SEQ ID NO:64];

-continued

| Met | Asn | Cys | Ser | Asn | Met | Ile | Asp |
| | | | Glu | Ile | Ile | Thr | His | Leu | Lys |
| Gln | Pro | Pro | Leu | Pro | Leu | Leu | Asp |
| | | | Phe | Asn | Asn | Leu | Asn | Gly | Glu |
| Asp | Gln | Asp | Ile | Leu | Met | Glu | Asn |
| | | | Asn | Leu | Arg | Arg | Pro | Asn | Leu |
| Glu | Ala | Phe | Asn | Arg | Ala | Val | Lys |
| | | | Ser | Leu | Gln | Asn | Ala | Ser | Ala |
| Ile | Glu | Ser | Ile | Leu | Lys | Asn | Leu |
| | | | Leu | Pro | Cys | Leu | Pro | Leu | Ala |
| Thr | Ala | Ala | Pro | Thr | Arg | His | Gly |
| | | | Val | Phe | Ile | Arg | Asp | Gly | Asp |
| Trp | Asn | Glu | Phe | Arg | Arg | Lys | Leu |
| | | | Thr | Phe | Tyr | Leu | Tyr | Thr | Leu |
| Glu | Asn | Ala | Gln | Ala | Gln | Gln | [SEQ ID NO:66]; |
| Met | Asn | Cys | Ser | Asn | Met | Ile | Asp |
| | | | Glu | Ile | Ile | Thr | His | Leu | Lys |
| Gln | Pro | Pro | Leu | Pro | Leu | Leu | Asp |
| | | | Phe | Asn | Asn | Leu | Asn | Gly | Glu |
| Asp | Gln | Asp | Ile | Leu | Met | Glu | Asn |
| | | | Asn | Leu | Arg | Arg | Pro | Asn | Leu |
| Glu | Ala | Phe | Asn | Arg | Ala | Val | Lys |
| | | | Ser | Leu | Gln | Asn | Ala | Ser | Ala |
| Ile | Glu | Ser | Ile | Leu | Lys | Asn | Leu |
| | | | Leu | Pro | Cys | Leu | Pro | Thr | Ser |
| Ala | Asn | Asp | Pro | Thr | Arg | His | Pro |
| | | | Ile | His | Ile | Lys | Asp | Gly | Asp |
| Trp | Asn | Glu | Phe | Arg | Arg | Lys | Leu |
| | | | Thr | Phe | Tyr | Leu | Lys | Thr | Leu |
| Glu | Asn | Ala | Gln | Ala | Gln | Gln | [SEQ ID NO:67]; |
| Met | Asn | Cys | Ser | Asn | Met | Ile | Asp |
| | | | Glu | Ile | Ile | Thr | His | Leu | Lys |
| Gln | Pro | Pro | Leu | Pro | Leu | Leu | Asp |
| | | | Phe | Asn | Asn | Leu | Asn | Gly | Glu |
| Asp | Gln | Asp | Ile | Leu | Met | Glu | Asn |
| | | | Asn | Leu | Arg | Arg | Pro | Asn | Leu |
| Glu | Ala | Phe | Asn | Arg | Ala | Val | Lys |
| | | | Ser | Leu | Gln | Asn | Ala | Ser | Ala |
| Ile | Lys | Ser | Asn | Leu | Gln | Lys | Leu |
| | | | Asn | Ser | Cys | Leu | Pro | Leu | Ala |
| Thr | Ala | Ala | Pro | Thr | Arg | His | Pro |
| | | | Ile | His | Ile | Lys | Ala | Gly | Asp |
| Trp | Asn | Glu | Phe | Arg | Arg | Lys | Leu |
| | | | Thr | Phe | Tyr | Leu | Lys | Thr | Leu |
| Glu | Asn | Ala | Gln | Ala | Gln | Gln | [SEQ ID NO:68]; |
| and | | | | | | | |
| Met | Asn | Cys | Ser | Asn | Met | Ile | Asp |
| | | | Glu | Ile | Ile | Thr | His | Leu | Lys |
| Gln | Pro | Pro | Leu | Pro | Leu | Leu | Glu |
| | | | Pro | Glu | Leu | Lys | Asn | Gly | Glu |
| Asp | Gln | Asp | Ile | Leu | Met | Glu | Asn |
| | | | Asn | Leu | Arg | Arg | Pro | Asn | Leu |
| Glu | Ala | Phe | Asn | Arg | Ala | Val | Lys |
| | | | Ser | Leu | Gln | Asn | Ala | Ser | Ala |
| Ile | Glu | Ser | Ile | Leu | Lys | Asn | Leu |
| | | | Leu | Pro | Cys | Leu | Pro | Leu | Ala |
| Thr | Ala | Ala | Pro | Thr | Arg | His | Pro |
| | | | Ile | His | Ile | Lys | Asp | Gly | Asp |
| Trp | Asn | Glu | Phe | Arg | Arg | Lys | Leu |
| | | | Thr | Phe | Tyr | Leu | Lys | Thr | Leu |
| Glu | Asn | Ala | Gln | Ala | Gln | Gln | [SEQ ID NO:75] |

2. A pharmaceutical composition comprising a therapeutically effective amount of a polypeptide selected from the group consisting of a polypeptide having an amino acid sequence corresponding to SEQ ID NO: 64;

a polypeptide having an amino acid sequence corresponding to SEQ ID NO: 66;

a polypeptide having an amino acid sequence corresponding to SEQ ID NO: 67;

a polypeptide having an amino acid sequence corresponding to SEQ ID NO: 68; and a polypeptide having an amino acid sequence corresponding to SEQ ID NO: 75;

and a pharmaceutically acceptable carrier.

3. A recombinant DNA sequence comprising vector DNA and a DNA selected from the group consisting of a DNA having a nucleotide sequence corresponding to SEQ ID NO: 78;

a DNA having a nucleotide sequence corresponding to SEQ ID NO: 81;

a DNA having a nucleotide sequence corresponding to SEQ ID NO: 82;

a DNA having a nucleotide sequence corresponding to SEQ ID NO: 83; and a DNA having a nucleotide sequence corresponding to SEQ ID NO: 91.

4. A host cell containing a recombinant DNA sequence selected from the group consisting of a DNA having a nucleotide sequence corresponding to SEQ ID NO: 78;

a DNA having a nucleotide sequence corresponding to SEQ ID NO: 81;

a DNA having a nucleotide sequence corresponding to SEQ ID NO: 82;

a DNA having a nucleotide sequence corresponding to SEQ ID NO: 83; and a DNA having a nucleotide sequence corresponding to SEQ ID NO: 91 and capable of expressing the encoded polypeptide.

5. A host cell containing a recombinant DNA vector comprising vector DNA and a DNA having a nucleotide sequence corresponding to a DNA selected from the group consisting of a DNA having a nucleotide sequence corresponding to SEQ ID NO: 78;

a DNA having a nucleotide sequence corresponding to SEQ ID NO: 81;

a DNA having a nucleotide sequence corresponding to SEQ ID NO: 82;

a DNA having a nucleotide sequence corresponding to SEQ ID NO: 83; and a DNA having a nucleotide sequence corresponding to SEQ ID NO: 91 and capable of expressing the encoded polypeptide.

6. A method of producing a human/murine interleukin-3 hybrid polypeptide comprising the steps of:

(a) culturing a host cell containing a recombinant DNA sequence comprising vector DNA and a DNA sequence selected from the group consisting of a DNA having a nucleotide sequence corresponding to SEQ ID NO: 78;

a DNA having a nucleotide sequence corresponding to SEQ ID NO: 81;

a DNA having a nucleotide sequence corresponding to SEQ ID NO: 82;

a DNA having a nucleotide sequence corresponding to SEQ ID NO: 83; and a DNA having a nucleotide sequence corresponding to SEQ ID NO: 91 and capable of expressing the encoded polypeptide under conditions permitting expression of the recombinant DNA;

(b) harvesting the polypeptide from the culture; and (c) recovering said human/murine interleukin-3 hybrid polypeptide.

7. A vector consisting a DNA sequence selected from the group consisting of:

a DNA having a nucleotide sequence corresponding to SEQ ID NO: 78;

a DNA having a nucleotide sequence corresponding to SEQ ID NO: 81;

a DNA having a nucleotide sequence corresponding to SEQ ID NO: 82;

a DNA having a nucleotide sequence corresponding to SEQ ID NO: 83; and a DNA having a nucleotide sequence corresponding to SEQ ID NO: 91.

8. A recombinant DNA vector comprising a promoter and a ribosome binding site directly linked to a DNA sequence encoding a polypeptide selected from the group consisting of a polypeptide having an amino acid sequence corresponding to SEQ ID NO: 64;

a polypeptide having an amino acid sequence corresponding to SEQ ID NO: 66;

a polypeptide having an amino acid sequence corresponding to SEQ ID NO: 67;

a polypeptide having an amino acid sequence corresponding to SEQ ID NO: 68; and a polypeptide having an amino acid sequence corresponding to SEQ ID NO: 75; said vector being capable of directing expression of said mutant human interleukin-3 polypeptide.

9. A recombinant DNA vector according to claim 8 wherein the promoter is precA.

10. A recombinant DNA vector according to claim 8 wherein the ribosome binding site is g10-L.

11. A recombinant DNA vector according to claim 8 wherein the promoter is precA and the ribosome binding site is g10-L.

12. A recombinant bacterial host which comprises the vector of claim 11 wherein said host expresses a mutant human interleukin-3 polypeptide selected from the group consisting of a polypeptide having an amino acid sequence corresponding to SEQ ID NO: 64;

a polypeptide having an amino acid sequence corresponding to SEQ ID NO: 66;

a polypeptide having an amino acid sequence corresponding to SEQ ID NO: 67;

a polypeptide having an amino acid sequence corresponding to SEQ ID NO: 68; and a polypeptide having an amino acid sequence corresponding to SEQ ID NO: 75.

13. A polypeptide which is selected from the group consisting of

| Met | Asn | Cys | Ser | Asn | Met | Ile | Asp | Glu | Ile | Ile | Thr | His | Leu | Lys |
|---|---|---|---|---|---|---|---|---|---|---|---|---|---|---|
| Gln | Pro | Pro | Leu | Pro | Leu | Leu | Asp | Phe | Asn | Asn | Leu | Asn | Gly | Glu |
| Asp | Gln | Asp | Ile | Leu | Met | Glu | Asn | Asn | Leu | Arg | Arg | Pro | Asn | Leu |
| Glu | Ala | Phe | Asn | Arg | Ala | Val | Lys | Ser | Leu | Gln | Pro | Glu | Asp | Arg |
| Tyr | Val | Ile | Glu | Ser | Ile | Leu | Lys | Asn | Leu | Leu | Pro | Cys | Leu | Pro |
| Leu | Ala | Thr | Ala | Ala | Pro | Thr | Arg | His | Pro | Ile | His | Ile | Lys | Ala |
| Gly | Asp | Trp | Asn | Glu | Phe | Arg | Arg | Lys | Leu | Thr | Phe | Tyr | Leu | Lys |
| Thr | Leu | Glu | Asn | Ala | Gln | Ala | Gln | Gln | [SEQ ID NO:64]; and | | | | | |
| Met | Asn | Cys | Ser | Asn | Met | Ile | Asp | Glu | Ile | Ile | Thr | His | Leu | Lys |
| Gln | Pro | Pro | Leu | Pro | Leu | Leu | Glu | Pro | Glu | Leu | Lys | Asn | Gly | Glu |
| Asp | Gln | Asp | Ile | Leu | Met | Glu | Asn | Asn | Leu | Arg | Arg | Pro | Asn | Leu |
| Glu | Ala | Phe | Asn | Arg | Ala | Val | Lys | Ser | Leu | Gln | Asn | Ala | Ser | Ala |
| Ile | Glu | Ser | Ile | Leu | Lys | Asn | Leu | Pro | Cys | Leu | Pro | Leu | Ala |
| Thr | Ala | Ala | Pro | Thr | Arg | His | Pro | Ile | His | Ile | Lys | Asp | Gly | Asp |
| Trp | Asn | Glu | Phe | Arg | Arg | Lys | Leu | Thr | Phe | Tyr | Leu | Lys | Thr | Leu |
| Glu | Asn | Ala | Gln | Ala | Gln | Gln | [SEQ ID NO:75].- | | | | | | | |

14. A pharmaceutical composition comprising a therapeutically effective amount of a polypeptide selected from the group consisting of a polypeptide having an amino acid sequence corresponding to SEQ ID NO: 64; and a polypeptide having an amino acid sequence corresponding to SEQ ID NO: 75 and a pharmaceutically acceptable carrier.

15. A recombinant DNA sequence comprising vector DNA and a DNA selected from the group consisting of;

a DNA having a nucleotide sequence corresponding to SEQ ID NO: 78; and a DNA having a nucleotide sequence corresponding to SEQ ID NO: 91.

16. A host cell containing a recombinant DNA vector comprising vector DNA and a DNA having a nucleotide sequence corresponding to a DNA selected from the group consisting of;

a DNA having a nucleotide sequence corresponding to SEQ ID NO: 78; and a DNA having a nucleotide sequence corresponding to SEQ ID NO: 91 and capable of expressing the encoded polypeptide.

17. A method of producing a human/murine interleukin-3 hybrid polypeptide comprising the steps of:

(a) culturing a host cell containing a recombinant DNA sequence comprising vector DNA and a DNA sequence selected from the group consisting of;

a DNA having a nucleotide sequence corresponding to SEQ ID NO: 78; and a DNA having a nucleotide sequence corresponding to SEQ ID NO: 91 and capable of expressing the encoded polypeptide under conditions permitting expression of the recombinant DNA; and (b) recovering of the polypeptide from the culture.

\* \* \* \* \*